United States Patent
Govindan et al.

(10) Patent No.: US 11,020,489 B2
(45) Date of Patent: *Jun. 1, 2021

(54) IMMUNOCONJUGATES WITH AN INTRACELLULARLY-CLEAVABLE LINKAGE

(71) Applicant: Immunomedics, Inc., Morris Plains, NJ (US)

(72) Inventors: Serengulam V. Govindan, Summit, NJ (US); Sung-Ju Moon, New Providence, NJ (US); David M. Goldenberg, Mendham, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/841,345

(22) Filed: Apr. 6, 2020

(65) Prior Publication Data
US 2020/0276325 A1 Sep. 3, 2020

Related U.S. Application Data

(60) Division of application No. 16/733,816, filed on Jan. 3, 2020, which is a division of application No. 15/612,672, filed on Jun. 2, 2017, now Pat. No. 10,561,738, which is a division of application No. 14/956,769, filed on Dec. 2, 2015, now Pat. No. 9,700,634, which is a division of application No. 14/660,310, filed on Mar. 17, 2015, now Pat. No. 9,233,172, which is a division of application No. 14/258,228, filed on Apr. 22, 2014, now Pat. No. 9,138,485, which is a division of application No. 13/291,238, filed on Nov. 8, 2011, now Pat. No. 8,741,300, which is a division of application No. 13/164,275, filed on Jun. 20, 2011, now Pat. No. 8,080,250, which is a division of application No. 12/629,404, filed on Dec. 2, 2009, now Pat. No. 7,999,083, which is a continuation-in-part of application No. 12/026,811, filed on Feb. 6, 2008, now Pat. No. 7,591,994, which is a continuation-in-part of application No. 11/388,032, filed on Mar. 23, 2006, now Pat. No. 8,877,901, which is a continuation-in-part of application No. 10/734,589, filed on Dec. 15, 2003, now Pat. No. 7,585,491.

(Continued)

(51) Int. Cl.
| | |
|---|---|
| *A61K 31/4745* | (2006.01) |
| *A61K 47/68* | (2017.01) |
| *C07K 16/10* | (2006.01) |
| *C07K 16/28* | (2006.01) |
| *C07K 16/30* | (2006.01) |
| *C07D 491/22* | (2006.01) |
| *C07K 16/18* | (2006.01) |
| *A61K 45/06* | (2006.01) |
| *A61N 5/10* | (2006.01) |
| *A61K 39/00* | (2006.01) |

(52) U.S. Cl.
CPC ...... *A61K 47/6803* (2017.08); *A61K 31/4745* (2013.01); *A61K 45/06* (2013.01); *A61K 47/6841* (2017.08); *A61K 47/6849* (2017.08); *A61K 47/6851* (2017.08); *A61K 47/6853* (2017.08); *A61K 47/6855* (2017.08); *A61K 47/6857* (2017.08); *A61K 47/6861* (2017.08); *A61K 47/6889* (2017.08); *A61N 5/10* (2013.01); *C07D 491/22* (2013.01); *C07K 16/1063* (2013.01); *C07K 16/18* (2013.01); *C07K 16/2803* (2013.01); *C07K 16/2833* (2013.01); *C07K 16/2863* (2013.01); *C07K 16/2887* (2013.01); *C07K 16/30* (2013.01); *C07K 16/303* (2013.01); *C07K 16/3046* (2013.01); *C07K 16/3076* (2013.01); *C07K 16/3092* (2013.01); *A61K 2039/505* (2013.01); *C07K 2317/21* (2013.01); *C07K 2317/24* (2013.01); *C07K 2317/31* (2013.01); *C07K 2317/40* (2013.01); *C07K 2317/52* (2013.01); *C07K 2317/53* (2013.01); *C07K 2317/94* (2013.01); *Y02A 50/30* (2018.01)

(58) Field of Classification Search
CPC ........... A61K 47/6803; A61K 47/6889; A61K 47/6851; C07K 16/2803
USPC ..................................................... 424/178.1
See application file for complete search history.

(56) References Cited

U.S. PATENT DOCUMENTS

| | | |
|---|---|---|
| 4,359,457 A | 11/1982 | Neville et al. |
| 5,112,954 A | 5/1992 | Abrams et al. |

(Continued)

FOREIGN PATENT DOCUMENTS

| | | |
|---|---|---|
| EP | 0253202 | 1/1988 |
| EP | 0306943 | 3/1989 |

(Continued)

OTHER PUBLICATIONS

Bardia et al., "Safety and efficacy of anti-Trop-2 antibody drug conjugate, sacituzumab govitecan (IMMU-132), in heavily pretreated patients with TNBC", Poster presented at San Antonio Breast Cancer Symposium, Dec. 10, 2015, San Antonio, TX.

(Continued)

*Primary Examiner* — Yan Xiao
(74) *Attorney, Agent, or Firm* — Richard A. Nakashima

(57) ABSTRACT

The present invention relates to therapeutic conjugates with improved ability to target various diseased cells containing a targeting moiety (such as an antibody or antibody fragment), a linker and a therapeutic moiety, and further relates to processes for making and using the conjugates.

16 Claims, 3 Drawing Sheets

Specification includes a Sequence Listing.

Related U.S. Application Data

(60) Provisional application No. 61/207,890, filed on Feb. 13, 2009, provisional application No. 60/668,603, filed on Apr. 6, 2005, provisional application No. 60/728,292, filed on Oct. 19, 2005, provisional application No. 60/751,196, filed on Dec. 16, 2005, provisional application No. 60/433,017, filed on Dec. 13, 2002.

(56) References Cited

U.S. PATENT DOCUMENTS

| | | | |
|---|---|---|---|
| 5,708,146 | A | 1/1998 | Willner et al. |
| 5,824,701 | A | 10/1998 | Greenwald et al. |
| 6,156,754 | A | 12/2000 | Lerchen et al. |
| 6,214,345 | B1 | 4/2001 | Firestone et al. |
| 6,716,821 | B2 | 4/2004 | Zhao et al. |
| 7,122,636 | B1 | 10/2006 | Hsei et al. |
| 7,238,785 | B2 | 7/2007 | Govindan et al. |
| 7,312,318 | B2 | 12/2007 | Hansen et al. |
| 7,999,083 | B2 | 8/2011 | Govindan et al. |
| 8,741,300 | B2 | 6/2014 | Govindan et al. |
| 8,759,496 | B2 | 6/2014 | Govindan et al. |
| 9,138,485 | B2 | 9/2015 | Govindan et al. |
| 9,233,172 | B2 | 1/2016 | Govindan et al. |
| 9,345,783 | B2 | 5/2016 | Govindan et al. |
| 9,480,756 | B2 | 11/2016 | Govindan et al. |
| 9,493,573 | B2 | 11/2016 | Govindan et al. |
| 9,493,574 | B2 | 11/2016 | Govindan et al. |
| 9,499,631 | B2 | 11/2016 | Govindan et al. |
| 9,522,959 | B2 | 12/2016 | Govindan et al. |
| 9,629,926 | B2 | 4/2017 | Govindan et al. |
| 9,855,344 | B2 | 1/2018 | Govindan et al. |
| 9,931,417 | B2 | 4/2018 | Govindan et al. |
| 10,034,950 | B2 | 7/2018 | Govindan et al. |
| 10,064,957 | B2 | 9/2018 | Govindan et al. |
| 10,130,626 | B2 | 11/2018 | Govindan et al. |
| 10,137,196 | B2 | 11/2018 | Govindan et al. |
| 10,143,756 | B2 | 12/2018 | Govindan et al. |
| 10,206,918 | B2 | 2/2019 | Govindan et al. |
| 2001/0034363 | A1 | 10/2001 | Li et al. |
| 2003/0133972 | A1 | 7/2003 | Danthi et al. |
| 2004/0001838 | A1 | 1/2004 | Zhao et al. |
| 2006/0142506 | A1 | 6/2006 | Breitenkamp et al. |
| 2008/0166363 | A1 | 7/2008 | Govindan et al. |

FOREIGN PATENT DOCUMENTS

| | | |
|---|---|---|
| WO | 0076551 | 12/2000 |
| WO | 0100245 A2 | 1/2001 |
| WO | 0124763 | 4/2001 |
| WO | 0174402 A2 | 10/2001 |
| WO | 2004054622 | 7/2004 |

OTHER PUBLICATIONS

Bardia et al., "Safety and tumor responses of the anti-Trop-2 antibody drug conjugate, sacituzumab govitecan (IMMU-132), in refractory, metastatic, triple-negative breast cancer (TNBC): An ongoing Phase II trial", Poster presented at AACR-NCI-EORTC International Conference: Molecular Targets and Cancer Therapeutics, Nov. 8, 2015, Boston, MA.

Basu et al., "The epithelial/carcinoma antigen EGP-1, recognized by monoclonal antibody RS7-3G11, is phosphorylated on serine 303", Int J Cancer. Aug. 9, 1995;62(4):472-9.

Basu et al., "Epithelial glycoprotein EGP-1 recognized by MAb RS7-3G11 is phosphorylated on serine 303", Proc. Amer. Assoc. Cancer Res. 36: 439 (Abstr. #2621), 1995.

Camidge et al., "Therapy of Advanced Metastatic Lung Cancers with an Anti-Trop-2-SN-38 Antibody-Drug Conjugate, IMMU-132: Interim Phase II Clinical Results", Oral presentation at 16th World Conference on Lung Cancer (WCLC), Sep. 7, 2015, Denver, CO.

Cardillo et al., "A novel immunotoxin comprising quadruple RNase tethered to an internalizing anti-TROP-2 humanized MAb shows potent cytotoxicity against diverse solid tumors in vitro", Proc. Amer. Assoc. Cancer Res. Annual Meeting, 51:1296 (Abstr. #5346), 2010.

Cardillo et al., "Combining an anti-Trop-2 antibody-SN-38 conjugate (sacituzumab govitecan) with microtubule inhibitors (paclitaxel and eribulin mesylate) or PARP inhibitor (olaparib) significantly improves therapeutic outcome in experimental triple-negative breast cancer (TNBC)", Mol Cancer Ther 2015;14(12 Suppl 2):Abstract nr C166.

Cardillo et al., "Synthetic lethality in TNBC mediated by an anti-Trop-2 antibody-drug conjugate, sacituzumab govitecan (IMMU-132), when combined with paclitaxel or the PARP inhibitor, olaparib", Poster presented at San Antonio Breast Cancer Symposium, Dec. 10, 2015, San Antonio, TX.

Chang et al., "In vitro and in vivo evaluation of a novel recombinant immunotoxin of ranpirnase fused to a humanized anti-EGP-1 antobody, HRS7, for the potential treatment of prostate and lung cancers", Proc. Amer. Assoc. Cancer Res. Annual Meeting, 48: (Abstr. #4795), 2007.

Goldenberg et al., Tolerability in mice, monkeys, and rabbits of new antibody (MAb)-drug (SN-38) immunoconjugates. Proc. Amer. Assoc. Cancer Res. 102nd Annual Meeting, 52: 865 (Abstr. #3619), 2011.

Goldenberg et al., "SN-38 antibody-drug conjugates as a novel platform for solid cancer therapy: preclinical science", American Association for Cancer Research (AACR) 2014 Annual Meeting, Abstr. #2904, Apr. 7, 2014.

Goldenberg et al., "Characterization of an anti-Trop-2-SN-38 antibody-drug conjugate (IMMU-132) with potent activity against solid cancers", American Society of Clinical Oncology (ASCO) 50th Annual Meeting. J Clin Oncol 32:5s, 2014 (suppl; abstr #3107), 2014.

Goldenberg et al., "IMMU-132, a potential new antibody-drug conjugate (ADC) for the treatment of triple-negative breast cancer (TNBC): Preclinical and initial clinical results", Poster P5-19-08 presented at San Antonio Breast Cancer Symposium, Dec. 9-13, 2014.

Govindan et al., "Optimal cleavable linker for antibody-SN-38 conjugates for cancer therapy: Impact of linker's stability on efficacy", Proc. Amer. Assoc. Cancer Res. 103rd Annual Meeting, 53: 611 (Abstr. #2526), 2012.

Govindan et al., "Preclinical therapy of breast cancer with a radioiodinated humanized anti-EGP-1 monoclonal antibody: advantage of a residualizing iodine radiolabel", Breast Cancer Res Treat. Mar. 2004;84(2):173-82.

Govindan et al., "Conjugation of SN-38 to an anti-EGP-1 MAB, HRS7, via a cleavable linker shows selective therapeutic activity in a preclinical model of non-small cell lung cancer (NSCLC)", Proc. Eleventh Conf. on Cancer Therapy, Cancer Biotherapy & Radiopharmaceuticals, 21(4):401 (Abstr. #56), 2006.

Govindan et al., "Therapy of human colonic and lung cancer xenografts with SN-38 conjugates of anti-CEACAM5 and anti-EGP-1 humanized monoclonal antibodies", Proc. AACR Molecular Targets and Cancer Therapeutics, 347-348 (Abstr. #C287), 2007.

Govindan et al., "Efficacious therapies of two human pancreatic cancer xenografts and an aggressive human lymphoma xenograft with redesigned antibody-SN-38 conjugates", Proc. Amer. Assoc. Cancer Res. Annual Meeting, 51:591 (Abstr. #2438), 2010.

Liu et al., "Novel immunoRNases comprising multiple copies of ranpimase display potent cytotoxicity in human breast cancer cell lines expressing Trop-2", Proc. Amer. Assoc. Cancer Res. 103rd Annual Meeting, 53: 1124 (Abstr. #4636), 2012.

Ocean et al., "Interim results of IMMU-132 (sacituzumab govitecan), an anti-trop-2 antibody-drug conjugate (ADC) in patients with metastatic gastrointestinal (GI) cancers", Poster presented at ESMO's 17th World Congress on Gastrointestinal Cancer, Jul. 4, 2015.

Picozzi et al., "IMMU-132, a new antibody-drug conjugate (ADC), evaluated in patients with advanced, metastatic, pancreatic ductal adenocarcinoma (mPC): Results of a Phase I/II trial", Poster presented at American Association for Cancer Research (AACR)

(56) References Cited

OTHER PUBLICATIONS

Special Conference on Pancreatic Cancer:Innovations in Research and Treatment, Abstr. #B99, May 18-21, 2014.
Shih et al., "Radioimmunodetection and radioimmunotherapy of xenografted human breast cancer with monoclonal antibody RS7", J. Immunother. 16: 169 (Abstr. #85), 1994.
Starodub et al., "Advanced solid cancer therapy with a novel antibody-drug conjugate (ADC), sacituzumab govitecan (IMMU-132): key preclinical and clinical results", Abstract CT236. Presented at American Association for Cancer Research (AACR) 2015 Annual Meeting, Philadelphia, PA, Apr. 20, 2015.
Starodub et al., "Safety, efficacy, and pharmacokinetics of a new humanized anti-Trop-2 antibody-SN-38 conjugate (IMMU-132) for the treatment of diverse epithelial cancers: Phase I clinical experience", AACR-NCI-EORTC International Conference on Molecular Targets and Cancer Therapeutics Meeting. (Abstr. #C67), Oct. 22, 2013.
Starodub et al., "SN-38 antibody-drug conjugate (ADC) targeting Trop-2, IMMU-132, as a novel platform for the therapy of diverse metastatic solid cancers: Initial clinical results", American Association for Cancer Research (AACR) 2014 Annual Meeting, Abstr. #CT206, Apr. 7, 2014.
Starodub et al., "Therapy of gastrointestinal malignancies with an anti-Trop-2-SN-38 antibody drug conjugate (ADC) (sacituzumab govitecan): Phase I/II clinical experience", 2015 American Society of Clinical Oncology (ASCO) Annual Meeting, J Clin Oncol 33, 2015 (suppl; abstr 3546), Board 38, Jun. 1, 2015.
Stein et al., "Therapy of a breast cancer xenograft using humanized RS7 labeled with residualizing iodine", Proc. Amer. Assoc. Cancer Res. 43: 88 (Abstr. #443), 2002.
Stein et al., "Radioimmunotherapy of lung cancer with MAb RS7-3G11", Proc. Amer. Assoc. Cancer Res. 33: 318 (Abstr. #1897), 1992.
Stein et al., "Radioimmunotherapy with MAb RS7-3G11 in an animal model", Antib. Immunoconj. Radiopharm. 5: 358 (Abstr. #100), 1992.
Stein et al., "Specificity and properties of MAb RS7-3G11 and the antigen defined by this pancarcinoma monoclonal antibody", Int J Cancer. Dec. 2, 1993;55(6):938-46.
Stein et al., "Comparative biodistribution and radioimmunotherapy of monoclonal antibody RS7 and its F(ab')2 in nude mice bearing human tumor xenografts", Cancer. Feb. 1, 1994;73(3 Suppl):816-23.
Stein et al., "Murine monoclonal antibodies raised against human non-small cell carcinoma of the lung: specificity and tumor targeting", Cancer Res. Feb. 15, 1990;50(4):1330-6.
Stein et al., "Effects of radiolabeling monoclonal antibodies with a residualizing iodine radiolabel on the accretion of radioisotope in tumors", Cancer Res. Jul. 15, 1995;55(14):3132-9.
Stein et al., "Successful therapy of a human lung cancer xenograft using MAb RS7 labeled with residualizing radioiodine", Rev Oncol Hematol. Jul.-Aug. 2001;39(1-2):173-80.
Stein et al., "Assessment of combined radioimmunotherapy and chemotherapy for treatment of medullary thyroid cancer", Clin Cancer Res. 5(10 Suppl):3199s-206s, 1999.
Stein et al., Characterization of the epithelial/carcinoma antigen recognized by MAb RS7. Proc. Amer. Assoc. Cancer Res. 35: 501 (Abstr. #2986), 1994.
Stein et al., A novel tumor-associated antigen defined by MAb RS7-3G11: Characterization and internalization properties. Proc. Amer. Assoc. Cancer Res. 33: 341, 1992.
Stein et al., "Characterization of cluster 13: the epithelial/carcinoma antigen recognized by MAb RS7", Int J Cancer Suppl. 1994;8:98-102.
Stein et al., "Targeting and therapy of human non small cell carcinoma of the lung xenografts using 131 I labeled monoclonal antibody RS7 3G11", Proc. Amer. Assoc. Cancer Res. 32: 260, 1991.

Van Rij et al., "Imaging of prostate cancer with immuno-PET and immuno-SPECT using a radiolabeled anti-EGP-1 monoclonal antibody", J Nucl Med. 52(10):1601-7, 2011.
Van Rij et al., "Pretargeting of prostate cancer with an internalizing anti-EGP-1 x anti-HSG bispecific antibody", Annual Congress of the European Association of Nuclear Medicine, Birmingham, UK, Eur J Nucl Med Mol Imaging 38 (Suppl 2):S212 (Abstr. #OP582), 2011.
Vanama et al., Construction, characterization, and mammalian expression of an immunotoxin consisting of ranpimase (Rap) fused to a humanized anti-EGP-1 antibody, hRS7, as a potential therapeutic for prostate cancer. Proc. Amer. Assoc. Cancer Res., 96th Annual Meeting, 160 (Abstr. #679), 2005.
ADC Could Benefit Some with Breast Cancer, Cancer Discov. May 2019;9(5):570.
An ADC for Triple-Negative Breast Cancer, Cancer Discov. Jan. 2016;6(1):OF8.
Bardia et al., "Sacituzumab Govitecan-hziy in Triple-Negative Breast Cancer. Reply", N Engl J Med. Jun. 13, 2019;380(24):2382.
Bardia et al., "Sacituzumab Govitecan-hziy in Refractory Metastatic Triple-Negative Breast Cancer", N Engl J Med. Feb. 21, 2019;380(8):741-751.
Bardia et al., "Efficacy and Safety of Anti-Trop-2 Antibody Drug Conjugate Sacituzumab Govitecan (IMMU-132) in Heavily Pretreated Patients With Metastatic Triple-Negative Breast Cancer", J Clin Oncol. Jul. 1, 2017;35(19):2141-2148.
Burki, TK., "Sacituzumab govitecan activity in advanced breast cancer", Lancet Oncol. May 2017;18(5):e246.
Cardillo et al., "IMMU-140, a Novel SN-38 Antibody-Drug Conjugate Targeting HLA-DR, Mediates Dual Cytotoxic Effects in Hematologic Cancers and Malignant Melanoma", Mol Cancer Ther Jan. 2018;17(1):150-160.
Cardillo et al., "Synthetic Lethality Exploitation by an Anti-Trop-2-SN-38 Antibody-Drug Conjugate, IMMU-132, Plus PARP Inhibitors in BRCA1/2-wild-type Triple-Negative Breast Cancer", Clin Cancer Res. Jul. 1, 2017;23(13):3405-3415.
Cardillo et al., "Sacituzumab Govitecan (IMMU-132), an Anti-Trop-2/SN-38 Antibody-Drug Conjugate: Characterization and Efficacy in Pancreatic, Gastric, and Other Cancers", Bioconjug Chem. May 20, 2015;26(5):919-31.
Cardillo et al., "Humanized anti-Trop-2 IgG-SN-38 conjugate for effective treatment of diverse epithelial cancers: preclinical studies in human cancer xenograft models and monkeys", Clin Cancer Res. May 15, 2011;17(10):3157-69.
Chang et al., "Combining ABCG2 Inhibitors with IMMU-132, an Anti-Trop-2 Antibody Conjugate of SN-38, Overcomes Resistance to SN-38 in Breast and Gastric Cancers", Mol Cancer Ther. Aug. 2016;15(8):1910-9.
Dong et al., "Antibody-drug conjugates of 7-ethyl-10-hydroxycamptothecin: Sacituzumab govitecan and labetuzumab govitecan", Eur J Med Chem. Apr. 1, 2019;167:583-593.
Dotan et al., "Phase I/II Trial of Labetuzumab Govitecan (Anti-CEACAM5/SN-38 Antibody-Drug Conjugate) in Patients With Refractory or Relapsing Metastatic Colorectal Cancer", J Clin Oncol. Oct. 10, 2017;35(29):3338-3346.
Faltas et al., "Sacituzumab Govitecan, a Novel Antibody-Drug Conjugate, in Patients With Metastatic Platinum-Resistant Urothelial Carcinoma", Clin Genitourin Cancer. Feb. 2016;14(1):e75-9.
Goldenberg et al., "The emergence of trophoblast cell-surface antigen 2 (TROP-2) as a novel cancer target", Oncotarget. Jun. 22, 2018;9(48):28989-29006.
Goldenberg et al., "Antibody-drug conjugates targeting TROP-2 and incorporating SN-38: A case study of anti-TROP-2 sacituzumab govitecan", MAbs. Jul. 18, 2019:1-9.
Goldenberg et al., "Trop-2 is a novel target for solid cancer therapy with sacituzumab govitecan (IMMU-132), an antibody-drug conjugate (ADC)", Oncotarget. Sep. 8, 2015;6(26):22496-512.
Govindan et al., "Improving the therapeutic index in cancer therapy by using antibody-drug conjugates designed with a moderately cytotoxic drug", Mol Pharm. Jun. 1, 2015;12(6):1836-47.
Govindan et al., "Milatuzumab-SN-38 conjugates for the treatment of CD74+ cancers", Mol Cancer Ther. Jun. 2013;12(6):968-78.

(56) References Cited

OTHER PUBLICATIONS

Govindan et al., "CEACAM5-targeted therapy of human colonic and pancreatic cancer xenografts with potent labetuzumab-SN-38 immunoconjugates", Clin Cancer Res. Oct. 1, 2009;15(19):6052-61.
Gray et al., "Therapy of Small Cell Lung Cancer (SCLC) with a Topoisomerase-I-inhibiting Antibody-Drug Conjugate (ADC) Targeting Trop-2, Sacituzumab Govitecan", Clin Cancer Res. Oct. 1, 2017;23(19):5711-5719.
Han et al., "Sacituzumab Govitecan (IMMU-132) in treatment-resistant uterine serous carcinoma: A case report", Gynecol Oncol Rep. May 23, 2018;25:37-40.
Heist et al., "Therapy of Advanced Non-Small-Cell Lung Cancer With an SN-38-Anti-Trop-2 Drug Conjugate, Sacituzumab Govitecan", J Clin Oncol. Aug. 20, 2017;35(24):2790-2797.
Kaplon et al., "Antibodies to watch in 2019", MAbs. Feb./Mar. 2019;11(2):219-238.
Kaplon et al., "Antibodies to watch in 2018", MAbs. Feb./Mar. 2018;10(2):183-203.
Lu et al., "Advances in antibody therapeutics targeting small-cell lung cancer", Adv Clin Exp Med. Sep. 2018;27(9):1317-1323.
Nagayama et al., "Antibody-Drug Conjugates for the Treatment of Solid Tumors: Clinical Experience and Latest Developments", Target Oncol. Dec. 2017;12(6):719-739.
Ocean et al., "Sacituzumab govitecan (IMMU-132), an anti-Trop-2-SN-38 antibody-drug conjugate for the treatment of diverse epithelial cancers: Safety and pharmacokinetics", Cancer. Oct. 1, 2017;123(19):3843-3854.
Ozaki et al., "Sacituzumab Govitecan-hziy in Triple-Negative Breast Cancer", N Engl J Med. Jun. 13, 2019;380(24):2382.
Ponde et al., "Antibody-Drug Conjugates in Breast Cancer: a Comprehensive Review", Curr Treat Options Oncol. Apr. 1, 2019;20(5):37.
Sahota et al., "Sacituzumab govitecan: an antibody-drug conjugate", Expert Opin Biol Ther. Aug. 2017;17(8):1027-1031.
Sharkey et al., Selective and Concentrated Accretion of SN-38 with a CEACAM5-Targeting Antibody-Drug Conjugate (ADC), Labetuzumab Govitecan (IMMU-130), Mol Cancer Ther Jan. 2018;17(1):196-203.
Shvartsur et al., "Trop2 and its overexpression in cancers: regulation and clinical/therapeutic implications", Genes Cancer. Mar. 2015;6(3-4):84-105.
Stirrups, R., "Sacituzumab govitecan-hziy for triple-negative breast cancer", Lancet Oncol. Apr. 2019;20(4):e194.
Tray et al., "Antibody-drug conjugates in triple negative breast cancer", Future Oncol. Oct. 2018;14(25):2651-2661.
Vlachostergios et al., "Antibody-Drug Conjugates in Bladder Cancer", Bladder Cancer. Jul. 30, 2018;4(3):247-259.
Vranic et al., "Potential Novel Therapy Targets in Neuroendocrine Carcinomas of the Breast", Clin Breast Cancer. Apr. 2019;19(2):131-136.
Zangardi et al., "Sacituzumab for the treatment of triple-negative breast cancer: the poster child of future therapy?", Expert Opin Investig Drugs. Feb. 2019;28(2):107-112.
Bardia et al., "Therapy of refractory/relapsed metastatic triple-negative breast cancer (TNBC) with an anti-Trop-2-antibody-drug conjugate (ADC), sacituzumab govitecan (IMMU-132): Phase I/II clinical experience", J Clin Oncol 33, 2015 (suppl; abstr 1016), Retrieved from http://meetinglibrary.asco.org/content/150673-156.
Bennouna et al., "Therapeutic strategies for colorectal cancer in Europe and the United States: focus on chemotherapy for advanced colorectal cancer" Int. J. Clin. Oncol. (2002) 7:236-244.
Cao et al., "Bispecific Antibodies as Novel Bioconjugates" Bioconj. Chem. Nov.-Dec. 1998;9(6):635-44.
Cardillo et al., "Sacituzumab Govitecan (IMMU-132), an Anti-Trop-2/SN-38 Antibody-Drug Conjugate: Characterization and Efficacy in Pancreatic, Gastric, and Other Cancers", Bioconjug Chem. May 20, 2015;26(5):919-31, Epub May 8, 2015.
Carter et al., Chemotherapy of Cancer; 2nd Edition; John Wiley & Sons, New York, 1981; Appendix C.

Chari et al., "Immunoconjugates Containing Novel Maytansinoids: Promising Anticancer Drugs" Cancer Res. Jan. 1, 1992;52(1):127-31.
Dotan et al., "A new anti-CEA-SN-38 antibody-drug conjugate (ADC), IMMU-130, is active in controlling metastatic colorectal cancer (mCRC) in patients (pts) refractory or relapsing after irinotecan-containing chemotherapies: Initial results of a phase I/II study", J Clin Oncol 33, 2015 (suppl; abstr 2505), Retrieved from http://meetinglibrary.asco.org/content/148390-156.
Frolich et al., "The anti-CD74 humanized monoclonal antibody, milatuzumab, which targets the invariant chain of MHC II complexes, alters B-cell proliferation, migration, and adhesion molecule expression", Arthritis Res Ther. Mar. 9, 2012;14(2):R54.
Goldenberg et al., "Trop-2 is a novel target for solid cancer therapy with sacituzumab govitecan (IMMU-132), an antibody-drug conjugate (ADC)", Oncotarget. Jun. 18, 2015. [Epub ahead of print].
Govindan et al., "CEACAM5-targeted therapy of human colonic and pancreatic cancer xenografts with potent abetuzumab-SN-38 immunoconjugates", Clin Cancer Res. Oct. 1, 2009;15(19):6052-61.
Govindan et al., "IMMU-130, a unique antibody-drug conjugate (ADC) of SN-38 targeting CEACAM5 antigen: Preclinical basis for clinical activity in metastatic colorectal cancer (mCRC)", J Clin Oncol 33, 2015 (suppl 3; abstr 625), Retrieved from http://meetinglibrary.asco.org/content/139777-158.
Govindan et al., "Improving the therapeutic index in cancer therapy by using antibody-drug conjugates designed with a moderately cytotoxic drug", Mol Pharm. Jun. 1, 2015;12(6):1836-47. doi: 10.1021/mp5006195. Epub Nov. 25, 2014.
Guarino et al., "Therapy of advanced metastatic lung cancer with an anti-Trop-2-SN-38 antibody-drug conjugate (ADC), sacituzumab govitecan (IMMU-132): Phase I/II clinical experience", J Clin Oncol 33, 2015 (suppl; abstr 2504), Retrieved from http://meetinglibrary.asco.org/content/148373-156.
Gueritte-Voegelein et al., "Relationships between the Structure of Taxol Analogues and Their Antimitotic Activity" J. Med. Chem. 1991, 34, 992-998.
Guillemard et al., "Taxane-Antibody Conjugates Afford Potent Cytotoxicity, Enhanced Solubility, and Tumor Target Selectivity" Cancer Res. 61, 694-699, Jan. 15, 2001.
Hatzakis et al., "Synthesis and single enzyme activity of a clicked lipase-BSA hetero-dimer" Chem. Commun., 2006, 2012-2014.
Heindel et al., "A Novel Heterobifunctional Linker for Formyl to Thiol Coupling" Bioconjugate Chem. 1991, 2, 427-430.
Hohlfeld et al., "Genetic restriction of autoreactive acetylcholine receptor-specific T lymphocytes in myasthenia gravis", J Immunol. Oct. 1985;135(4):2393-9.
Huang et al., "The Rana catesbeiana rcr Gene Encoding a Cytotoxic Ribonuclease" J. Biol. Chem. 273 (11):6395-6401 (1998).
Jiang et al., "A novel peptide isolated from a phage display peptide library with trastuzumab can mimic antigen epitope of HER-2", J Biol Chem. Feb. 11, 2005;280(6):4656-62.
King et al., "Monoclonal Antibody Conjugates of Doxorubicin Prepared with Branched Linkers: A Novel Method for Increasing the Potency of Doxorubicin Immunoconjugates" Bioconjugate Chem. 1999, 10, 279-288.
Kreitman et al., "Pseudomonas Exotoxin-based Immunotoxins Containing the Antibody LL2 or LL2-Fab' Induce Regression of Subcutaneous Human B-Cell Lymphoma in Mice" Cancer Res. 53, 819-825, Feb. 15, 1993.
Krontiris and Capizzi, Internal Medicine, Chapters 71-72, pp. 699-729; 4th Edition, Jay Stein (Ed.), Elsevier Science, 1994.
Miller et al., "Development of Taxoids with Enhanced Toxicity and Solubility" Poster Presentation, 224th ACS Nat. Meeting, Aug. 18-22, 2002, Boston, MA.
Moon et al., "Antibody Conjugates of 7-Ethyl-10-hydroxycamptothecin (SN-38) for Targeted Cancer Chemotherapy" J. Med. Chem. 2008, 51, 6916-6926.
Newton et al., "Potent and specific antitumor effects of an anti-CD22-targeted cytotoxic ribonuclease: potential for the treatment of non-Hodgkin lymphoma" Blood, 97(2):528-35 (2001).

(56) References Cited

OTHER PUBLICATIONS

Perez et al., "Inhibition by the anti-mitotic drug doxorubicin of platelet-activating-factor-induced late eosinophil accumulation in rats" Eur. J. Pharmacol. Sep. 4, 1998;356(2-3):239-43.

Reddy et al., "Elimination of Fc Receptor-Dependent Effector Functions of a Modified IgG4 Monoclonal Antibody to Human CD4", J. Immunol. 164:1925-1933 (2000).

Rowlinson-Busza et al., "Targeted delivery of biologic and other antineoplastic agents" Curr. Opin. Oncol. Dec. 1992;4(6):1142-1148.

Sharkey et al., "Combination radioimmunotherapy and chemoimmunotherapy involving different or the same targets improves therapy of human pancreatic carcinoma xenograft models", Mol Cancer Ther. Jun. 2011;10(6):1072-81.

Sharkey et al., "Epratuzumab-SN-38: a new antibody-drug conjugate for the therapy of hematologic malignancies", Mol Cancer Ther. Jan. 2012;11(1):224-34.

Sharkey et al., "Enhanced Delivery of SN-38 to Human Tumor Xenografts with an Anti-Trop-2-SN-38 Antibody conjugate (Sacituzumab Govitecan)", Clin Cancer Res. Jun. 23, 2015. pii: clincanres.0670.2015. [Epub ahead of print].

Shih et al., "The Processing and Fate of Antibodies and Their Radiolabels Bound to the Surface of Tumor Cells In Vitro: A Comparison of Nine Radiolabels" J. Nucl. Med. 1994; 35:899-908.

Stancovski et al., "Mechanistic aspects of the opposing effects of monoclonal antibodies to the ERBB2 receptor on tumor growth", Proc Natl Acad Sci U S A. Oct. 1, 1991;88(19):8691-5.

Starodub et al., "Phase I/II trial of IMMU-132 (isactuzumab govitecan), an anti-Trop-2-SN-38 antibody drug conjugate (ADC): Results in patients with metastatic gastrointestinal (GI) cancers", J Clin Oncol 33, 2015 (suppl 3; abstr 703), Retrieved from http://meetinglibrary.asco.org/content/140198-158.

Starodub et al., "First-in-Human Trial of a Novel Anti-Trop-2 Antibody-SN-38 Conjugate, Sacituzumab Govitecan, or the Treatment of Diverse Metastatic Solid Tumors", Clin Cancer Res. May 5, 2015. [Epub ahead of print].

Steinfeld et al., "Epratuzumab (humanised anti-CD22 antibody) in autoimmune diseases", Expert Opin Biol Ther. Sep. 2006;6(9):943-9.

Suzawa et al., "Synthesis of a Novel Duocarmycin Derivative DU-257 and its Application to Immunoconjugate Using Poly(ethylene glycol)-dipeptidyl Linker Capable of Tumor Specific Activation" Bioorg. Med. Chem. 8(8):2175-84 (2000).

Suzawa et al., "Enhanced tumor cell selectivity of adriamycin-monoclonal antibody conjugate via a poly(ethylene glycol)-based cleavable linker" J. Control. Release 79:229-242 (2002).

Trail et al., "Carcinoma Reactive Doxorubicin (DOX) Conjugates: Comparison of BR64-DOX Conjugates Prepared With Disulfide or Thioether Linkers", Proc. Amer. Assoc. Cancer Res., vol. 34, Mar. 1993, #2858, p. 479.

Walker et al., "Synthesis of an Immunoconjugate of Camptothecin" Bioorg. Med. Chem. Lett. 12(2):217-219 (2002).

Yazawa et al., "Immunotherapy using unconjugated CD19 monoclonal antibodies in animal models for B lymphocyte malignancies and autoimmune disease", Proc Natl Acad Sci U S A. Oct. 18, 2005;102(42):15178-83.

SEQUENCE LISTING

<160> NUMBER OF SEQ ID NOS: 15

<210> SEQ ID NO 1
<211> LENGTH: 44
<212> TYPE: PRT
<213> ORGANISM: Homo sapiens

<400> SEQUENCE: 1

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 2
<211> LENGTH: 45
<212> TYPE: PRT
<213> ORGANISM: Homo sapiens

<400> SEQUENCE: 2

Cys Gly His Ile Gln Ile Pro Pro Gly Leu Thr Glu Leu Leu Gln Gly
1               5                   10                  15

Tyr Thr Val Glu Val Leu Arg Gln Gln Pro Pro Asp Leu Val Glu Phe
            20                  25                  30

Ala Val Glu Tyr Phe Thr Arg Leu Arg Glu Ala Arg Ala
        35                  40                  45

<210> SEQ ID NO 3
<211> LENGTH: 17
<212> TYPE: PRT
<213> ORGANISM: Homo sapiens

<400> SEQUENCE: 3

Gln Ile Glu Tyr Leu Ala Lys Gln Ile Val Asp Asn Ala Ile Gln Gln
1               5                   10                  15

Ala

<210> SEQ ID NO 4
<211> LENGTH: 21
<212> TYPE: PRT
<213> ORGANISM: Homo sapiens

<400> SEQUENCE: 4

Cys Gly Gln Ile Glu Tyr Leu Ala Lys Gln Ile Val Asp Asn Ala Ile
1               5                   10                  15

Gln Gln Ala Gly Cys
            20

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Ile Glu Tyr Val Ala Lys Gln Ile Val Asp Tyr Ala Ile His Gln
1               5                   10                  15

Ala

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

Gln Ile Glu Tyr Lys Ala Lys Gln Ile Val Asp His Ala Ile His Gln
1               5                   10                  15

Ala

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Ile Glu Tyr His Ala Lys Gln Ile Val Asp His Ala Ile His Gln
1               5                   10                  15

Ala

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Ile Glu Tyr Val Ala Lys Gln Ile Val Asp His Ala Ile His Gln
1               5                   10                  15

Ala

<210> SEQ ID NO 9
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asp Leu Ile Glu Glu Ala Ala Ser Arg Ile Val Asp Ala Val Ile Glu
1               5                   10                  15

Gln Val Lys Ala Ala Gly Ala Tyr
            20

<210> SEQ ID NO 10
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Glu Gln Tyr Ala Asn Gln Leu Ala Asp Gln Ile Ile Lys Glu Ala
1               5                   10                  15

Thr Glu

<210> SEQ ID NO 11
<211> LENGTH: 20
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 11

Phe Glu Glu Leu Ala Trp Lys Ile Ala Lys Met Ile Trp Ser Asp Val
1               5                   10                  15

Phe Gln Gln Cys
            20

<210> SEQ ID NO 12
<211> LENGTH: 25
<212> TYPE: PRT
<213> ORGANISM: Homo sapiens

<400> SEQUENCE: 12

Pro Glu Asp Ala Glu Leu Val Arg Leu Ser Lys Arg Leu Val Glu Asn
1               5                   10                  15

Ala Val Leu Lys Ala Val Gln Gln Tyr
            20                  25

<210> SEQ ID NO 13
<211> LENGTH: 25
<212> TYPE: PRT
<213> ORGANISM: Homo sapiens

<400> SEQUENCE: 13

Pro Glu Asp Ala Glu Leu Val Arg Thr Ser Lys Arg Leu Val Glu Asn
1               5                   10                  15

Ala Val Leu Lys Ala Val Gln Gln Tyr
            20                  25

<210> SEQ ID NO 14
<211> LENGTH: 25
<212> TYPE: PRT
<213> ORGANISM: Homo sapiens

<400> SEQUENCE: 14

Pro Glu Asp Ala Glu Leu Val Arg Leu Ser Lys Arg Asp Val Glu Asn
1               5                   10                  15

Ala Val Leu Lys Ala Val Gln Gln Tyr
            20                  25

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Leu Ala Leu
1
```

IMMUNOCONJUGATES WITH AN INTRACELLULARLY-CLEAVABLE LINKAGE

RELATED APPLICATIONS

This application is a divisional of U.S. patent application Ser. No. 16/733,816, filed Jan. 3, 2020, which was a divisional of U.S. patent application Ser. No. 15/612,672 (now issued U.S. Pat. No. 10,561,738), filed Jun. 2, 2017, which was a divisional of U.S. patent application Ser. No. 14/956,769 (now issued U.S. Pat. No. 9,700,634), filed Dec. 2, 2015, which was a divisional of U.S. patent application Ser. No. 14/660,310 (now issued U.S. Pat. No. 9,233,172), filed Mar. 17, 2015, which was a divisional of U.S. patent application Ser. No. 14/258,228 (now issued U.S. Pat. No. 9,138,485), filed Apr. 22, 2014, which was a divisional of U.S. patent Ser. No. 13/291,238 (now issued U.S. Pat. No. 8,741,300), filed Nov. 8, 2011, which was a divisional of U.S. patent application Ser. No. 13/164,275 (now issued U.S. Pat. No. 8,080,250), filed Jun. 20, 2011, which was a divisional of U.S. patent application Ser. No. 12/629,404 (now issued U.S. Pat. No. 7,999,083), filed Dec. 2, 2009, which claimed the benefit of U.S. Provisional Patent Application No. 61/207,890, filed Feb. 13, 2009; and which was a continuation-in-part of U.S. patent application Ser. No. 12/026,811 (now issued U.S. Pat. No. 7,591,994), filed Feb. 6, 2008, which was a continuation-in-part of U.S. patent application Ser. No. 11/388,032 (now issued U.S. Pat. No. 8,877,901), filed Mar. 23, 2006, which claimed the benefit of U.S. Provisional Patent Application Nos. 60/668,603, filed Apr. 6, 2005; 60/728,292, filed Oct. 19, 2005; and 60/751,196, filed Dec. 16, 2005; and which was a continuation-in-part of U.S. patent application Ser. No. 10/734,589 (now issued U.S. Pat. No. 7,585,491), filed Dec. 15, 2003, which claimed the benefit under 35 USC 119(e) of U.S. Provisional Patent Application No. 60/433,017, filed Dec. 13, 2002. The text of each of the priority applications is incorporated herein by reference in its entirety.

GOVERNMENT SUPPORT

This invention was made with government support under Grant Number CA114802 awarded by the National Institutes of Health. The government has certain rights in the invention.

FIELD OF THE INVENTION

The present invention relates to therapeutic conjugates with improved ability to target various cancer cells, infectious disease organisms and/or for treating autoimmune diseases, which conjugates contain a targeting (binding) moiety and a therapeutic moiety belonging to the camptothecin group of drugs. The targeting and therapeutic moieties are linked via an intracellularly cleavable linkage that increases therapeutic efficacy.

BACKGROUND OF THE INVENTION

For many years it has been an aim of scientists in the field of specifically targeted drug therapy to use monoclonal antibodies (MAbs) for the specific delivery of toxic agents to human cancers. Conjugates of tumor-associated MAbs and suitable toxic agents have been developed, but have had mixed success in the therapy of cancer, and virtually no application in other diseases, such as infectious and autoimmune diseases. The toxic agent is most commonly a chemotherapeutic drug, although particle-emitting radionuclides, or bacterial or plant toxins have also been conjugated to MAbs, especially for the therapy of cancer (Sharkey and Goldenberg, C A Cancer J Clin. 2006 July-August; 56(4): 226-243) and, more recently, with radioimmunoconjugates for the preclinical therapy of certain infectious diseases (Dadachova and Casadevall, Q J Nucl Med Mol Imaging 2006; 50(3):193-204; incorporated herein by reference).

The advantages of using MAb-chemotherapeutic drug conjugates are that (a) the chemotherapeutic drug itself is structurally well defined; (b) the chemotherapeutic drug is linked to the MAb protein using very well defined conjugation chemistries, often at specific sites remote from the MAbs antigen binding regions; (c) MAb-chemotherapeutic drug conjugates can be made more reproducibly than chemical conjugates involving MAbs and bacterial or plant toxins, and as such are more amenable to commercial development and regulatory approval; and (d) the MAb-chemotherapeutic drug conjugates are orders of magnitude less toxic systemically than radionuclide MAb conjugates.

Early work on protein-drug conjugates indicated that a drug preferably is released in its original form, once it has been internalized into a target cell, for the protein-chemotherapeutic drug conjugate to be a useful therapeutic. Trouet et al. (*Proc. Natl. Acad. Sci. USA* 79:626-629 (1982)) showed the advantage of using specific peptide linkers, between the drug and the targeting moiety, which are cleaved lysosomally to liberate the intact drug. Notably, MAb-chemotherapeutic drug conjugates prepared using mild acid-cleavable linkers, such as those containing a hydrazone, were developed, based on the observation that the pH inside tumors was often lower than normal physiological pH (Willner et al., U.S. Pat. No. 5,708,146; Trail et al. (*Science* 261:212-215 (1993)). The first approved MAb-drug conjugate, Gemtuzumab Ozogamicin, incorporates a similar acid-labile hydrazone bond between an anti-CD33 antibody, humanized P67.6, and a potent calicheamicin derivative. Sievers et al., *J Clin Oncol.* 19:3244-3254 (2001); Hamann et al., *Bioconjugate Chem.* 13: 47-58 (2002). In some cases, the MAb-chemotherapeutic drug conjugates were made with reductively labile hindered disulfide bonds between the chemotherapeutic drugs and the MAb (Liu et al., *Proc Natl Acad Sci USA* 93: 8618-8623 (1996)).

Yet another cleavable linker involves cathepsin B-labile dipeptide spacers, such as Phe-Lys or Val-Cit, similar to the lysosomally labile peptide spacers of Trouet et al. containing from one to four amino acids, which additionally incorporated a collapsible spacer between the drug and the dipeptide (Dubowchik, et al., *Bioconjugate Chem.* 13:855-869 (2002); Firestone et al., U.S. Pat. No. 6,214,345 B1; Doronina et al., *Nat Biotechnol.* 21: 778-784 (2003)). The latter approaches were also utilized in the preparation of an immunoconjugate of camptothecin (Walker et al., *Bioorg Med Chem Lett.* 12:217-219 (2002)). Another cleavable moiety that has been explored is an ester linkage incorporated into the linker between the antibody and the chemotherapeutic drug. Gillimard and Saragovi have found that when an ester of paclitaxel was conjugated to anti-rat p75 MAb, MC192, or anti-human TrkA MAb, 5C3, the conjugate was found to exhibit target-specific toxicity. Gillimard and Saragovi, *Cancer Res.* 61:694-699 (2001).

The conjugates of the instant invention possess greater efficacy, in many cases, than unconjugated or "naked" antibodies or antibody fragments, although such unconjugated targeting molecules have been of use in specific situations. In cancer, for example, naked antibodies have come to play a role in the treatment of lymphomas (CAMPATH® (alemtuzumab) and RITUXAN® (rituximab)), colorectal and other cancers (ERBITUX® (cetuximab) and AVASTIN® (bevacizumab)), breast cancer (HERECEPTIN® (trastuzumab)), as well as a large number now in clinical development (e.g., epratuzumab). In most of these cases, clinical use has involved combining these naked, or unconjugated, antibodies with other therapies, such as chemotherapy or radiation therapy.

A variety of antibodies are also in use for the treatment of autoimmune and other immune dysregulatory diseases, such as tumor necrosis factor (TNF) and B-cell (RITUXAN® (rituximab)) antibodies in arthritis, and are being investigated in other such diseases, such as the B-cell antibodies, RITUXAN® (rituximab) and epratuzumab, in systemic lupus erythematosus and Sjögren's syndrome, as well as juvenile diabetes and multiple sclerosis. Naked antibodies are also being studied in sepsis and septic shock, Alzheimer's disease, and infectious diseases. The development of anti-infective monoclonal antibodies has been reviewed recently by Reichert and Dewitz (Nat Rev Drug Discovery 2006; 5:191-195), incorporated herein by reference, which summarizes the priority pathogens against which naked antibody therapy has been pursued, resulting in only 2 pathogens against which antibodies are either in Phase III clinical trials or are being marketed (respiratory syncytial virus and methicillin-resistant *Staphylococcus aureus*), with 25 others in clinical studies and 20 discontinued during clinical study.

There is a need to develop more potent anti-pathogen or anti-cancer antibodies and other binding moieties. Such antibody-mediated therapeutics can be developed for the treatment of many different pathogens, including bacteria, fungi, viruses, and parasites, either as naked (unconjugated), radiolabeled, or drug/toxin conjugates. There is a further need to develop more effective antibody conjugates with intracellularly cleavable linkers, of use for the treatment of cancer, pathogens and other diseases. In the case of delivering drug/toxin or radionuclide conjugates, this can be accomplished by direct antibody conjugation or by indirect methods, referred to as pretargeting, where a bispecific antibody is used to target to the lesion, while the therapeutic agent is secondarily targeted by binding to one of the arms of the bispecific antibody that has localized at the site of the pathogen, the cancer or whatever lesion is being treated (Goldenberg et al., J Clin Oncol. 2006 Feb. 10; 24(5):823-34.; Goldenberg et al., J Nucl Med. 2008 January; 49(1): 158-63, each incorporated herein by reference in their entirety).

SUMMARY OF THE INVENTION

The present invention resolves an unfulfilled need in the art by providing improved methods and compositions for preparation of drug-binding moiety conjugates. The disclosed methods and compositions are of use for the treatment of a variety of diseases and conditions which are refractory or less responsive to other forms of therapy, and can include diseases against which suitable targeting (binding) moieties for selective targeting can be developed, or are available or known. Preferably, the targeting moiety is an antibody, antibody fragment, bispecific or other multivalent antibody, or other antibody-based molecule or compound. The antibody can be of various isotypes, preferably IgG1, IgG2a, IgG3, IgG4 or IgA, and can be a chimeric human-mouse, a chimeric human-primate, a humanized (human framework and murine hypervariable (CDR) regions), or fully human antibody, as well as variations thereof, such as half-IgG4 antibodies (referred to as "unibodies") as described by van der Neut Kolfschoten et al. (Science 2007; 317:1554-1557), incorporated herein by reference. However, other binding moieties known in the art, such as aptamers, avimers or targeting peptides, may be used. Preferred diseases or conditions against which such targeting moieties exist are, for example, cancer, immune dysregulatory conditions, including autoimmune diseases and inflammatory diseases, and diseases caused by infectious organisms.

The disclosed methods and compositions may thus be applied for treatment of diseases and conditions for which targeting moieties are of use to deliver cytotoxic agents. Such diseases or conditions may be characterized by the presence of a target molecule or target cell that is insufficiently affected when unconjugated, or naked, targeting moieties are used, such as in the immunotherapy of cancer or of infection with pathogenic organisms. (For methods of making immunoconjugates of antibodies with isotopes, drugs, and toxins for use in disease therapies, see, e.g., U.S. Pat. Nos. 4,699,784; 4,824,659; 5,525,338; 5,677,427; 5,697,902; 5,716,595; 6,071,490; 6,187,284; 6,306,393; 6,548,275; 6,653,104; 6,962,702; 7,033,572; 7,147,856; 7,259,240 and U.S. Patent Appln. Publ. Nos. 20050175582 (now abandoned); 20050136001; 20040166115 (now abandoned); 20040043030 (now abandoned); 20030068322 (now abandoned) and 20030026764 (now abandoned), the Examples section of each incorporated herein by reference.)

In a preferred embodiment, camptothecin (CPT) and its analogs and derivatives are preferred chemotherapeutic moieties, although the invention is not so limited. Other chemotherapeutic moieties that are within the scope of the invention are taxanes (e.g, baccatin III, taxol), epothilones, anthracycline drugs (e.g., doxorubicin (DOX), epirubicin, morpholinodoxorubicin (morpholino-DOX), cyanomorpholino-doxorubicin (cyanomorpholino-DOX), and 2-pyrrolinodoxorubicin (2-PDOX); see Priebe W (ed.), ACS symposium series 574, published by American Chemical Society, Washington D.C., 1995 (332 pp) and Nagy et al., Proc. Natl. Acad. Sci. USA 93:2464-2469, 1996), benzoquinoid ansamycins exemplified by geldanamycin (DeBoer et al., Journal of Antibiotics 23:442-447, 1970; Neckers et al., Invest. New Drugs 17:361-373, 1999), and the like. Preferably, in the immunoconjugates of the preferred embodiments of the present invention, the targeting moiety links to at least one chemotherapeutic moiety; preferably 1 to about 5 chemotherapeutic moieties; most preferably about 7 to about 12 chemotherapeutic moieties.

With regard to the CPT group of drugs, issues of insolubility in aqueous buffers and the lability of the δ-lactone moiety of the E-ring of their structures under physiological conditions are relevant. One approach has been to acylate the 20-hydroxyl group with an amino acid, and couple the α-amino group of the amino acid to poly-L-glutamic acid (Singer et al. in *The Camptothecins: Unfolding Their Anticancer Potential*, Liehr J. G., Giovanella, B. C. and Verschraegen (eds), NY Acad Sci., NY 922:136-150 (2000)). This approach relies on the passive diffusion of a polymeric molecule into tumor sites. This glycine conjugation has also been reported as a method of making a water-soluble derivative of CPT (Vishnuvajjala et al., U.S. Pat. No. 4,943,579) and in the preparation of a PEG-derivatized CPT (Greenwald, et al. *J. Med. Chem.* 39: 1938-1940 (1996)). In the latter case, the approach has been devised in the context of developing water-soluble and long acting forms of CPT, whereby CPT's in vivo half-life is enhanced, and the drug is gradually released from its conjugate while in circulation in vivo. An example of a water soluble CPT derivative is CPT-11. Extensive clinical data are available concerning CPT-11's pharmacology and its in vivo conversion to the active SN-38 (Iyer and Ratain, *Cancer Chemother Pharmacol.* 42:S31-43 (1998); Mathijssen et al., *Clin Cancer Res.* 7:2182-2194 (2002); Rivory, *Ann NY Acad Sci.* 922:205-215, 2000)). The active form SN-38 is about 2 to 3 orders of magnitude more potent than CPT-11.

In certain exemplary embodiments, drug conjugates of antibodies or antibody fragments may be used for targeting the therapeutic drug to pathogens, such as bacteria, viruses, fungi, and parasites. In preferred embodiments, such drug-conjugated targeting moieties can be used in combination with other therapeutic modalities, such as anti-fungal, antibiotics and anti-viral drugs and/or naked antibodies, immunomodulators (e.g., interferons, interleukins, and/or cytokines). The use of radioimmunotherapy for the treatment of infectious organisms is disclosed, for example, in U.S. Pat. Nos. 4,925,648; 5,332,567; 5,439,665; 5,601,825; 5,609,846; 5,612,016; 6,120,768; 6,319,500; 6,458,933; 6,548,275; and in U.S. Patent Application Publication Nos. 20020136690 and 20030103982, the Examples section of each of which is incorporated herein by reference.

In certain embodiments involving treatment of cancer, the drug conjugates may be used in combination with surgery, radiation therapy, chemotherapy, immunotherapy with naked antibodies, radioimmunotherapy, immunomodulators, vaccines, and the like. Similar combinations are preferred in the treatment of other diseases amenable to targeting moieties, such as autoimmune diseases. For example, camptothecin conjugates can be combined with TNF inhibitors, B-cell antibodies, interferons, interleukins, and other effective agents for the treatment of autoimmune diseases, such as rheumatoid arthritis, systemic lupus erythematosis, Sjögren's syndrome, multiple sclerosis, vasculitis, as well as type-I diabetes (juvenile diabetes). These combination therapies can allow lower doses of each therapeutic to be given in such combinations, thus reducing certain severe side effects, and potentially reducing the courses of therapy required. In viral diseases, the drug immunoconjugates can be combined with other therapeutic drugs, immunomodulators, naked MAbs, or vaccines (e.g., MAbs against hepatitis, HIV, or papilloma viruses, or vaccines based on immunogens of these viruses). Antibodies and antigen-based vaccines against these and other viral pathogens are known in the art and, in some cases, already in commercial use.

In one embodiment, the invention relates to a process of preparing conjugates, wherein a drug is first derivatized with a first linker, which first linker contains a reactive moiety that is capable of combining with a second linker that additionally contains a targeting-moiety-coupling group; wherein the first linker also possesses a defined polyethylene glycol (PEG) moiety for water-solubility, and optionally an intracellularly-cleavable moiety cleavable by intracellular peptidases or cleavable by the low pH environment of endosomal and lysosomal vescicles, and optionally an amino acid spacer between the drug and the first linker; wherein the second linker contains a reactive group capable of reacting with drug-(first linker) conjugate by the copper (+1) ion-catalyzed acetylene-azide cycloaddition reaction, referred to as 'click chemistry'. Preferably, the defined PEG moiety is a low molecular weight PEG with a defined number of monomeric subunits, as discussed below.

Another embodiment relates to a process of preparing conjugates as discussed in the paragraph above, wherein the second linker has a single targeting-moiety-coupling group, but multiples of the reactive group capable of reacting with drug-(first linker) conjugate, thereby amplifying the number of drug molecules conjugated to the targeting moiety.

A further embodiment relates to a process of preparing conjugates, wherein the linker is first conjugated to a drug, thereby producing a drug-linker conjugate; wherein said drug-linker conjugate preparation involves the selective protection and deprotection of a more reactive group in a drug containing multiple functional groups; wherein said drug-linker conjugate is optionally not purified; and wherein said drug-linker conjugate is subsequently conjugated to a monoclonal antibody or fragment.

Yet another embodiment is a method of treating cancer (malignancy), an autoimmune disease, an infection, or an infectious lesion with the conjugates described herein. Alternative embodiments concern the drug-targeting moiety conjugates made by the claimed processes and/or kits for performing the claimed processes.

In one embodiment, the invention relates to an immunoconjugate comprising:
  (a) a targeting moiety;
  (b) a chemotherapeutic moiety; and
  (c) a linker covalently attached to the targeting moiety via a targeting moiety-binding group and to the chemotherapeutic moiety via an intracellularly-cleavable moiety. In another embodiment, the invention relates to an immunoconjugate comprising:
  (a) targeting moiety;
  (b) a chemotherapeutic moiety; and
  (c) a linker covalently attached to the targeting moiety via a targeting moiety-binding group and to the chemotherapeutic moiety via an intracellularly-cleavable moiety; wherein said linker attachment to therapeutic moiety further comprises an L-amino acid or a polypeptide made up of up to four L-amino acids.

In one embodiment, the intracellularly-cleavable moiety is a carbonate comprising an activated hydroxyl group of the chemotherapeutic moiety and a substituted ethanolamine moiety or a 4-aminobenzyl alcohol, and the latter is attached, via its amino group, to a cross-linker terminating in the targeting moiety-binding group; and wherein the substituted ethanolamine moiety is derived from a natural L amino acid, with the carboxylic acid group of the latter replaced with a hydroxymethyl moiety; and wherein the 4-aminobenzyl alcohol is optionally substituted with a $C_1$-$C_{10}$ alkyl group at the benzylic position.

In a preferred embodiment, the intracellularly-cleavable moiety is a carbonate comprising an activated hydroxyl group of the chemotherapeutic moiety and a substituted ethanolamine moiety, and the latter, via its amino group, is attached to an L-amino acid or a polypeptide comprising up to four L-amino acid moieties; wherein the N-terminus is attached to a cross-linker terminating in the targeting moiety-binding group; and wherein the substituted ethanolamine moiety is optionally derived from an L amino acid, with the carboxylic acid group of the latter replaced with a hydroxymethyl moiety.

In another preferred embodiment, the intracellularly-cleavable moiety is a carbonate comprising an activated hydroxyl group of the chemotherapeutic moiety and a 4-aminobenzyl alcohol or substituted 4-aminobenzyl alcohol substituted with a C1-$C_{10}$ alkyl group at the benzylic position, and the latter, via its amino group, is attached to an L-amino acid or a polypeptide comprising up to four L-amino acid moieties; wherein the N-terminus is attached to a cross-linker terminating in the targeting moiety-binding group.

In certain embodiments, an amino group of a chemotherapeutic moiety is coupled to the activated hydroxyl group of a substituted, and amine-protected, ethanolamine moiety or a 4-aminobenzyl alcohol, and the latter is attached, via its amino group, to an L-amino acid or a polypeptide comprising up to four L-amino acid moieties; wherein the N-terminus is attached to a cross-linker terminating in the targeting moiety-binding group; wherein said substituted ethanolamine moiety is optionally derived from an L amino acid, with the carboxylic acid group of the latter replaced with a hydroxymethyl moiety; and wherein the 4-aminobenzyl alcohol is optionally substituted with a $C1-C_{10}$ alkyl group at the benzylic position. The bifunctional drug derivative is then conjugated to a targeting moiety to obtain an immunoconjugate as discussed above. Upon targeting the disease site with the immunoconjugate, the immunoconjugate is endocytosed and catabolized to release the drug-linker moiety; wherein the free amino group of the substituted ethanolamine moiety assists in the liberation of free drug by nucleophilic attack at the carbonyl group of the carbamate moiety.

DETAILED DESCRIPTION OF THE INVENTION

Definitions

Figure 1:
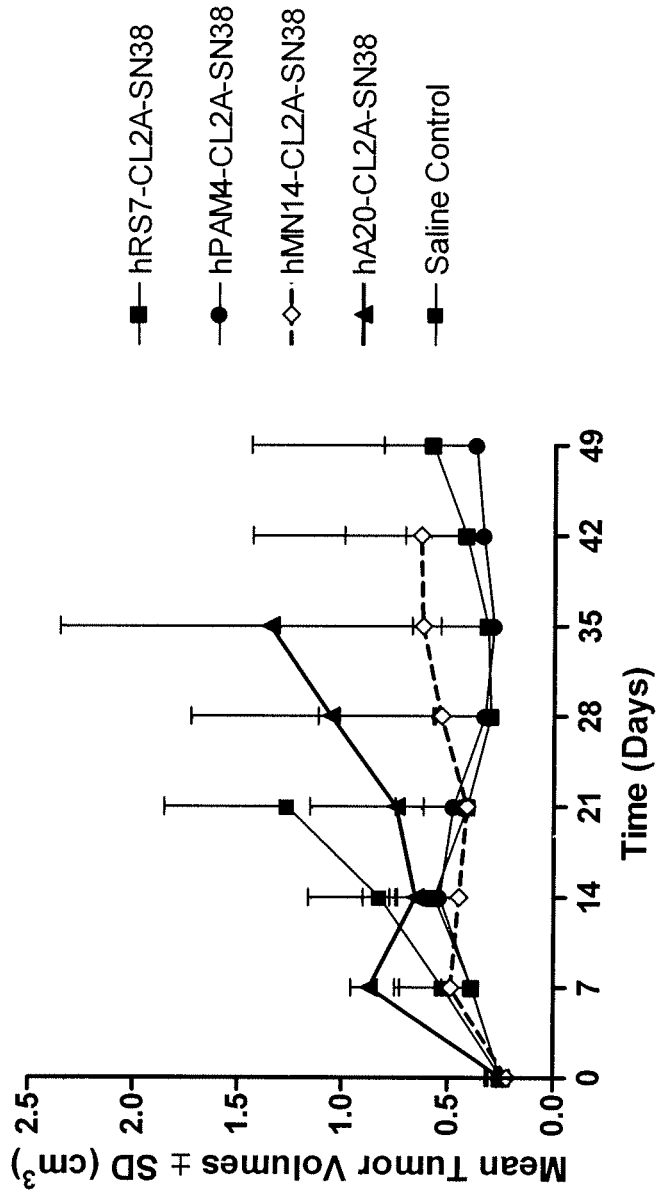
FIG. 1. Preclinical in vivo therapy of athymic nude mice, bearing Capan 1 human pancreatic carcinoma, with MAb-CL2A-SN-38 conjugates.

In the description that follows, a number of terms are used and the following definitions are provided to facilitate understanding of the claimed subject matter. Terms that are not expressly defined herein are used in accordance with their plain and ordinary meanings.

Unless otherwise specified, a or an means "one or more."

The term about is used herein to mean plus or minus ten percent (10%) of a value. For example, "about 100" refers to any number between 90 and 110.

The term targeting moiety as used herein refers to a molecule, complex or aggregate, that binds specifically or selectively to a target molecule, cell, particle, tissue or aggregate. The skilled artisan will understand that specific binding refers to binding to a particular target without cross-reactivity to other targets, while selective binding refers to preferential binding to a particular target. In preferred embodiments, a targeting moiety is an antibody, antibody fragment, bispecific antibody or other antibody-based molecule or compound. However, other examples of targeting moieties are known in the art and may be used, such as aptamers, avimers, receptor-binding ligands, nucleic acids, biotin-avidin binding pairs, binding peptides or proteins, etc. The terms "targeting moiety" and "binding moiety" are used synonymously herein.

An antibody, as used herein, refers to a full-length (i.e., naturally occurring or formed by normal immunoglobulin gene fragment recombinatorial processes) immunoglobulin molecule (e.g., an IgG antibody) or an antigen-binding portion of an immunoglobulin molecule, such as an antibody fragment. An antibody or antibody fragment may be conjugated or otherwise derivatized within the scope of the claimed subject matter. Such antibodies include but are not limited to IgG1, IgG2a, IgG3, IgG4 (and IgG4 subforms), as well as IgA isotypes.

An antibody fragment is a portion of an antibody such as F(ab')$_2$, F(ab)$_2$, Fab', Fab, Fv, scFv (single chain Fv), single domain antibodies (DABs or VHHs) and the like, including the half-molecules of IgG4 cited above (van der Neut Kolfschoten et al. (Science 2007; 317(14 September): 1554-1557). Regardless of structure, an antibody fragment of use binds with the same antigen that is recognized by the intact antibody. The term "antibody fragment" also includes synthetic or genetically engineered proteins that act like an antibody by binding to a specific antigen to form a complex. For example, antibody fragments include isolated fragments consisting of the variable regions, such as the "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region, such as CDRs. The Fv fragments may be constructed in different ways to yield multivalent and/or multispecific binding forms. In the case of multivalent, they have more than one binding site against the specific epitope, whereas with multispecific forms, more than one epitope (either of the same antigen or against one antigen and a different antigen) is bound. As used herein, the term antibody component includes an entire antibody, a fusion protein, and fragments thereof.

A naked antibody is generally an entire antibody that is not conjugated to a therapeutic agent. This is so because the Fc portion of the antibody molecule provides effector or immunological functions, such as complement fixation and ADCC (antibody-dependent cell cytotoxicity), which set mechanisms into action that may result in cell lysis. However, the Fc portion may not be required for therapeutic function of the antibody, but rather other mechanisms, such as apoptosis, anti-angiogenesis, anti-metastatic activity, anti-adhesion activity, such as inhibition of heterotypic or homotypic adhesion, and interference in signaling pathways, may come into play and interfere with disease progression. Naked antibodies include both polyclonal and monoclonal antibodies, and fragments thereof, that include murine antibodies, as well as certain recombinant antibodies, such as chimeric, humanized or human antibodies and fragments thereof. Therefore, in some cases a "naked antibody" may also refer to a "naked" antibody fragment. As defined herein, "naked" is synonymous with "unconjugated," and means not linked or conjugated to a therapeutic agent.

Autoimmune Diseases are disorders that are caused by the body producing an immune response against its own tissues. Examples include Class III autoimmune diseases such as immune-mediated thrombocytopenias, acute idiopathic thrombocytopenic purpura and chronic idiopathic thrombocytopenic purpura, dermatomyositis, Sjögren's syndrome, multiple sclerosis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, sarcoidosis, ulcerative colitis, erythema multiforme, IgA nephropathy, polyarteritis *nodosa*, ankylosing spondylitis, Goodpasture's syndrome, thromboangitis obliterans, Sjögren's syndrome, primary biliary cirrhosis, Hashimoto's thyroiditis, thyrotoxicosis, scleroderma, chronic active hepatitis, rheumatoid arthritis, polymyositis/dermatomyositis, polychondritis, pemphigus vulgaris, Wegener's granulomatosis, membranous nephropathy, amyotrophic lateral sclerosis, tabes *dorsalis*, giant cell arteritis/polymyalgia, pernicious anemia, rapidly progressive glomerulonephritis and fibrosing alveolitis, as disclosed in U.S. Provisional Application Ser. No. 60/360,259, filed Mar. 1, 2002, the Examples section of which is incorporated herein by reference.

A chimeric antibody is a recombinant protein that contains the variable domains of both the heavy and light antibody chains, including the complementarity determining regions (CDRs) of an antibody derived from one species, preferably a rodent antibody, more preferably a murine antibody, while the constant domains of the antibody molecule are derived from those of a human antibody. For veterinary applications, the constant domains of the chimeric antibody may be derived from that of other species, such as a primate, cat or dog.

A humanized antibody is a recombinant protein in which the CDRs from an antibody from one species; e.g., a murine antibody, are transferred from the heavy and light variable chains of the murine antibody into human heavy and light variable domains (framework regions). The constant domains of the antibody molecule are derived from those of a human antibody. In some cases, specific residues of the framework region of the humanized antibody, particularly those that are touching or close to the CDR sequences, may be modified, for example replaced with the corresponding residues from the original murine, rodent, subhuman primate, or other antibody.

A human antibody is an antibody obtained, for example, from transgenic mice that have been "engineered" to produce human antibodies in response to antigenic challenge. In this technique, elements of the human heavy and light chain loci are introduced into strains of mice derived from embryonic stem cell lines that contain targeted disruptions of the endogenous heavy chain and light chain loci. The transgenic mice can synthesize human antibodies specific for various antigens, and the mice can be used to produce human antibody-secreting hybridomas. Methods for obtaining human antibodies from transgenic mice are described by Green et al., *Nature Genet.* 7:13 (1994), Lonberg et al., *Nature* 368:856 (1994), and Taylor et al., *Int. Immun.* 6:579 (1994). A fully human antibody also can be constructed by genetic or chromosomal transfection methods, as well as phage display technology, all of which are known in the art. See for example, McCafferty et al., *Nature* 348:552-553 (1990) for the production of human antibodies and fragments thereof in vitro, from immunoglobulin variable domain gene repertoires from unimmunized donors. In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see e.g. Johnson and Chiswell, *Current Opinion in Structural Biology* 3:5564-571 (1993). Human antibodies may also be generated by in vitro activated B cells. See U.S. Pat. Nos. 5,567,610 and 5,229,275, the Examples section of each of which is incorporated herein by reference.

Infectious Diseases as used herein are diseases involving infection by pathogens such as bacteria, *rickettsia*, *mycoplasma*, protozoa, fungi, viruses, parasites, or other microbial agents. Examples include human immunodeficiency virus (HIV) causing AIDS, *Mycobacterium* of tuberculosis, *Streptococcus agalactiae*, methicillin-resistant *Staphylococcus aureus*, *Legionella pneumophilia*, *Streptococcus pyogenes*, *Escherichia coli*, *Neisseria gonorrhosae*, *Neisseria meningitidis*, Pneumococcus, *Cryptococcus neoformans*, *Histoplasma capsulatum*, *Hemophilis influenzae* B, *Treponema pallidum*, Lyme disease spirochetes, West Nile virus, *Pseudomonas aeruginosa*, *Mycobacterium leprae*, *Brucella abortus*, rabies virus, influenza virus, cytomegalovirus, herpes simplex virus I, herpes simplex virus II, human serum parvo-like virus, respiratory syncytial virus, varicella-zoster virus, hepatitis B virus, hepatitis C virus, measles virus, adenovirus, human T-cell leukemia viruses, Epstein-Barr virus, murine leukemia virus, mumps virus, vesicular stomatitis virus, sindbis virus, lymphocytic choriomeningitis virus, wart virus, blue tongue virus, Sendai virus, feline leukemia virus, reo virus, polio virus, simian virus 40, mouse mammary tumor virus, dengue virus, rubella virus, *Plasmodium falciparum*, *Plasmodium vivax*, *Toxoplasma gondii*, *Trypanosoma rangeli*, *Trypanosoma cruzi*, *Trypanosoma rhodesiensei*, *Trypanosoma brucei*, *Schistosoma mansoni*, *Schistosoma japanicum*, *Babesia bovis*, *Elmeria tenella*, *Onchocerca volvulus*, *Leishmania tropica*, *Trichinella spiralis*, *Theileria parva*, *Taenia hydatigena*, *Taenia ovis*, *Taenia saginata*, *Echinococcus granulosus*, *Mesocestoides corti*, *Mycoplasma arthritidis*, *M. hyorhinis*, *M. orale*, *M. arginini*, *Acholeplasma laidlawii*, *M. salivarium* and *M. pneumoniae*. A review listing antibodies against infectious organisms (antitoxin and antiviral antibodies), as well as other targets, is contained in Casadevall, Clin Immunol 1999; 93(1):5-15, incorporated herein by reference.

A therapeutic agent is a molecule or atom that is administered separately, concurrently or sequentially with a binding moiety, e.g., an antibody or antibody fragment, or a subfragment thereof, and is useful in the treatment of a disease. Examples of therapeutic agents include, but are not limited to, antibodies, antibody fragments, conjugates, drugs, cytotoxic agents, proapopoptotic agents, toxins, nucleases (including DNAses and RNAses), hormones, immunomodulators, chelators, boron compounds, photoactive agents or dyes, radioisotopes or radionuclides, oligonucleotides, interference RNA, peptides, anti-angiogenic agents, chemotherapeutic agents, cyokines, chemokines, prodrugs, enzymes, binding proteins or peptides or combinations thereof.

A conjugate is an antibody component or other targeting moiety conjugated to a therapeutic agent, such as those described above. As used herein, the terms "conjugate" and "immunoconjugate" are used interchangeably.

As used herein, the term antibody fusion protein is a recombinantly-produced antigen-binding molecule in which one or more natural antibodies, single-chain antibodies or antibody fragments are linked (fused) to another moiety, such as a protein or peptide toxin, cytokine, hormone, etc. In certain preferred embodiments, the fusion protein may comprise two or more of the same or different antibodies, antibody fragments or single-chain antibodies fused together, which may bind to the same epitope, different epitopes on the same antigen, or different antigens. An antibody fusion protein comprises at least one antigen binding site. The valency of the fusion protein indicates the total number of binding arms or sites the fusion protein has to antigen(s) or epitope(s); i.e., monovalent, bivalent, trivalent or multivalent. The multivalency of the antibody fusion protein means that it can take advantage of multiple interactions in binding to an antigen, thus increasing the avidity of binding to the antigen, or to different antigens. Specificity indicates how many different types of antigen or epitope an antibody fusion protein is able to bind; i.e., monospecific, bispecific, trispecific, multispecific. Using these definitions, a natural antibody, e.g., an IgG, is bivalent because it has two binding arms but is monospecific because it binds to one type of antigen or epitope. A monospecific, multivalent fusion protein has more than one binding site for the same antigen or epitope. For example, a monospecific diabody is a fusion protein with two binding sites reactive with the same antigen. The fusion protein may comprise a multivalent or multispecific combination of different antibody components or multiple copies of the same antibody component. The fusion protein may additionally comprise a therapeutic agent.

An immunomodulator is a therapeutic agent that when present, alters, suppresses or stimulates the body's immune system. Typically, an immunomodulator of use stimulates immune cells to proliferate or become activated in an immune response cascade, such as macrophages, dendritic cells, B-cells, and/or T-cells. However, in some cases an immunomodulator may suppress proliferation or activation of immune cells, as in therapeutic treatment of autoimmune disease. An example of an immunomodulator as described herein is a cytokine, which is a soluble small protein of approximately 5-20 kDa that is released by one cell population (e.g., primed T-lymphocytes) on contact with specific antigens, and which acts as an intercellular mediator between cells. As the skilled artisan will understand, examples of cytokines include lymphokines, monokines, interleukins, and several related signaling molecules, such as tumor necrosis factor (TNF) and interferons. Chemokines are a subset of cytokines. Certain interleukins and interferons are examples of cytokines that stimulate T cell or other immune cell proliferation.

CPT is abbreviation for camptothecin, and as used in the present application CPT represents camptothecin itself or an analog or derivative of camptothecin. The structures of camptothecin and some of its analogs, with the numbering indicated and the rings labeled with letters A-E, are given in formula 1 in Chart 1 below.

Chart 1

(1)

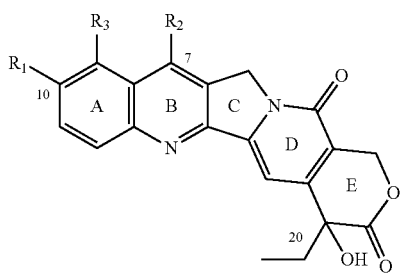

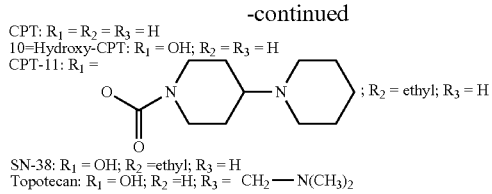

CPT: $R_1 = R_2 = R_3 = H$
10=Hydroxy-CPT: $R_1 = OH; R_2 = R_3 = H$
CPT-11: $R_1 = $ ; $R_2 = $ ethyl; $R_3 = H$
SN-38: $R_1 = OH; R_2 = $ ethyl; $R_3 = H$
Topotecan: $R_1 = OH; R_2 = H; R_3 = CH_2-N(CH_3)_2$ Camptothecin Conjugates Methods are devised in the following ways for the preparation of conjugates of chemotherapeutic drugs with targeting moieties (TM), such as an antibody (MAb). The disclosed methods represent a preferred embodiment of the invention. (1) Solubility of the drug is enhanced by placing a defined polyethyleneglycol (PEG) moiety (i.e., a PEG containing a defined number of monomeric units) between the drug and the targeting vector, wherein the defined PEG is a low molecular weight PEG, preferably containing 1-30 monomeric units, more preferably containing 1-12 monomeric units; (2) a first linker connects the drug at one end and terminates with an acetylene or an azide group at the other end; this first linker comprises a defined PEG moiety with an azide or acetylene group at one end and a different reactive group, such as carboxylic acid or hydroxyl group, at the other end and said bifunctional defined PEG is attached to the amine group of an amino alcohol, and the hydroxyl group of the latter is attached to the hydroxyl group on the drug in the form of a carbonate; alternatively, the non-azide (or acetylene) moiety of said defined bifunctional PEG is optionally attached to the N-terminus of a L-amino acid or a polypeptide, with the C-terminus attached to the amino group of amino alcohol, and the hydroxy group of the latter is attached to the hydroxyl group of the drug in the form of carbonate or carbamate, respectively; (3) a second linker, comprising a targeting moiety-coupling group and a reactive group complementary to the azide (or acetylene) group of the first linker, namely acetylene (or azide), reacts with the drug-(first linker) conjugate via acetylene-azide cycloaddition reaction to furnish the final bifunctional drug product that is useful for conjugating to the disease targeting moieties such as disease-targeting antibodies; (4) the antibody-coupling group is designed to be either a thiol or a thiol-reactive group; (5) methods are devised for selective regeneration of the 10-hydroxyl group in the presence of the C-20 carbonate in preparations of drug-linker precursor involving CPT analogs such as SN-38; (6) other protecting groups for reactive hydroxyl groups in drugs such as the phenolic hydroxyl in SN-38, for example, such as t-butyldimethylsilyl or t-butyldiphenylsilyl are also used, and these are deprotected by tetrabutylammonium fluoride prior to linking of the derivatized drug to a targeting-vector-coupling moiety; and (6) the 10-hydroxyl group of CPT analogs is alternatively protected as an ester or carbonate, other than 'BOC', such that the bifunctional CPT is conjugated to a targeting moiety without prior deprotection of this protecting group, and the protecting group is readily deprotected under physiological pH conditions after the bioconjugate is administered. In the acetylene-azide coupling, referred to as 'click chemistry', the azide part may be on L2 with the acetylene part on L3. Alternatively, L2 may contain acetylene, with L3 containing azide. 'Click chemistry' is a copper (+1)-catalyzed cycloaddition reaction between an acetylene moiety and an azide moiety, and is a relatively recent technique in bioconjugations (Kolb H C and Sharpless K B, *Drug Discov Today* 2003; 8: 1128-37). Click chemistry takes place in aqueous solution at near-neutral pH conditions, and is thus amenable for drug conjugation. The advantage of click chemistry is that it is chemoselective, and complements other well-known conjugation chemistries such as the thiol-maleimide reaction. In the following discussion, where a conjugate comprises an antibody or antibody fragment, another type of binding moiety, such as an aptamer, avimer or targeting peptide, may be substituted.

An exemplary preferred embodiment is directed to a conjugate of a drug derivative and an antibody of the general formula 2, MAb-[L2]-[L1]-[AA]$_m$-[A']-Drug  (2)

where MAb is a disease-targeting antibody; L2 is a component of the cross-linker comprising an antibody-coupling moiety and one or more of acetylene (or azide) groups; L1 comprises a defined PEG with azide (or acetylene) at one end, complementary to the acetylene (or azide) moiety in L2, and a reactive group such as carboxylic acid or hydroxyl group at the other end; AA is an L-amino acid; m is an integer with values of 0, 1, 2, 3, or 4; and A' is an additional spacer, selected from the group of ethanolamine, 4-hydroxybenzyl alcohol, 4-aminobenzyl alcohol, or substituted or unsubstituted ethylenediamine. The L amino acids of 'AA' are selected from alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. If the A' group contains hydroxyl, it is linked to the hydroxyl group or amino group of the drug in the form of a carbonate or carbamate, respectively.

In a preferred embodiment of formula 2, A' is a substituted ethanolamine derived from an L-amino acid, wherein the carboxylic acid group of the amino acid is replaced by a hydroxymethyl moiety. A' may be derived from any one of the following L-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine.

In an example of the conjugate of the preferred embodiment of formula 2, m is 0, A' is L-valinol, and the drug is exemplified by SN-38. The resultant structure is shown in formula 3.

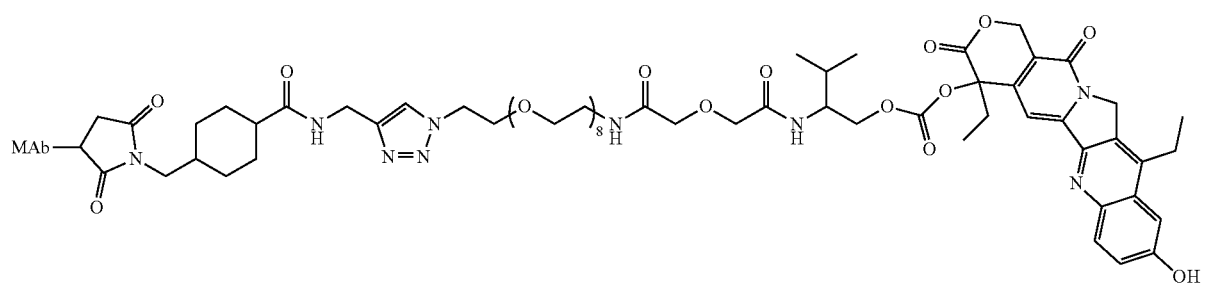

(3)

In another example of the conjugate of the preferred embodiment of formula 2, m is 1 and represented by a derivatized L-lysine, A' is L-valinol, and the drug is exemplified by SN-38. The structure is shown in formula 4.

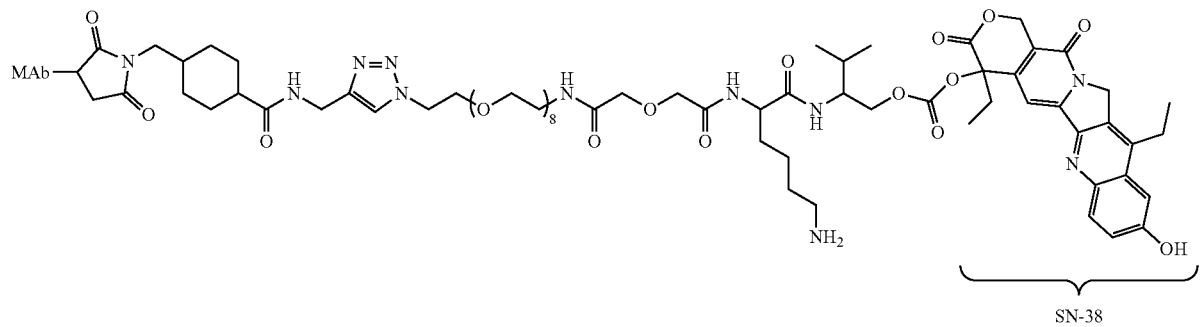

(4)

In this embodiment, an amide bond is first formed between the carboxylic acid of an amino acid such as lysine and the amino group of valinol, using orthogonal protecting groups for the lysine amino groups. The protecting group on the N-terminus of lysine is removed, keeping the protecting group on the side chain of lysine intact, and the N-terminus is coupled to the carboxyl group on the defined PEG with azide (or acetylene) at the other end. The hydroxyl group of valinol is then attached to the 20-chloroformate derivative of 10-hydroxy-protected SN-38, and this intermediate is coupled to an L2 component carrying the targeting vector-binding moiety as well as the complementary acetylene (or azide) group involved in the click cycloaddition chemistry. Finally, removal of protecting groups at both lysine side chain and SN-38 gives the product of this example, shown in formula 3.

While not wishing to be bound by theory, the small MW SN-38 product, namely valinol-SN-38 carbonate, generated after intracellular proteolysis, has the additional pathway of liberation of intact SN-38 through intramolecular cyclization involving the amino group of valinol and the carbonyl of the carbonate.

In another preferred embodiment, A' of the general formula 2 is A-OH, whereby A-OH is a collapsible moiety such as 4-aminobenzyl alcohol or a substituted 4-aminobenzyl alcohol substituted with a $C_1$-$C_{10}$ alkyl group at the benzylic position, and the latter, via its amino group, is attached to an L-amino acid or a polypeptide comprising up to four L-amino acid moieties; wherein the N-terminus is attached to a cross-linker terminating in the targeting moiety-binding group.

An example of a preferred embodiment is given below, wherein the A-OH embodiment of A' of general formula (2) is derived from substituted 4-aminobenzyl alcohol, and 'AA' is comprised of a single L-amino acid with m=1 in the general formula (2), and the drug is exemplified with SN-38. The structure is represented below (formula 5, referred to as MAb-CLX-SN-38). Single amino acid of AA is selected from any one of the following L-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. The substituent R on 4-aminobenzyl alcohol moiety (A-OH embodiment of A') is hydrogen or an alkyl group selected from C1-C10 alkyl groups.

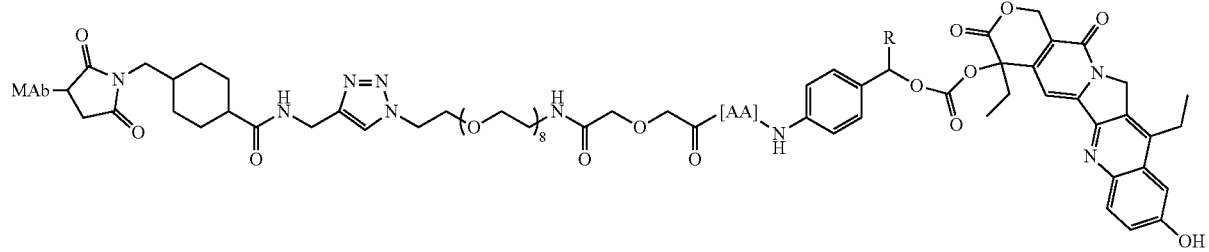

(5)

MAb-CLX-SN-38

An embodiment of MAb-CLX-SN-38 of formula 5, wherein the single amino acid AA is L-lysine and R═H, and the drug is exemplified by SN-38 (formula 6; referred to as MAb-CL2A-SN-38).

(6)

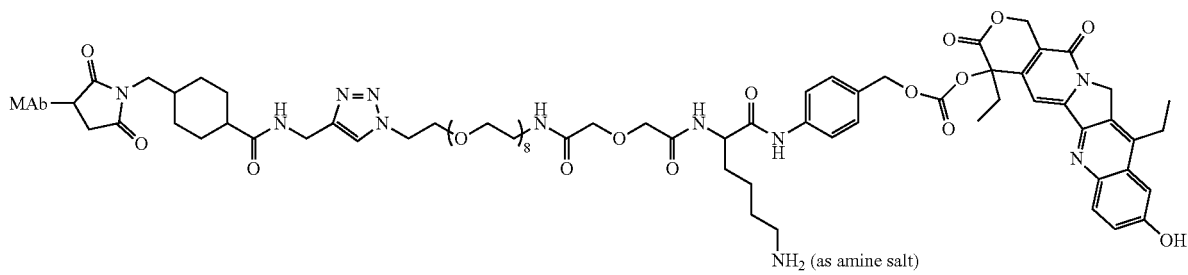

Other embodiments are possible within the context of 10-hydroxy-containing camptothecins, such as SN-38. In the example of SN-38 as the drug, the more reactive 10-hydroxy group of the drug is derivatized leaving the 20-hydroxyl group unaffected. Within the general formula 2, A' is a substituted ethylenediamine. An example of this embodiment is represented by the formula '7' below, wherein the phenolic hydroxyl group of SN-38 is derivatized as a carbamate with a substituted ethylenediamine, with the other amine of the diamine derivatized as a carbamate with a 4-aminobenzyl alcohol, and the latter's amino group is attached to Phe-Lys dipeptide. In this structure (formula 7), R and R' are independently hydrogen or methyl. It is referred to as MAb-CL17-SN-38 or MAb-CL2E-SN-38, when R═R'═methyl.

(7)

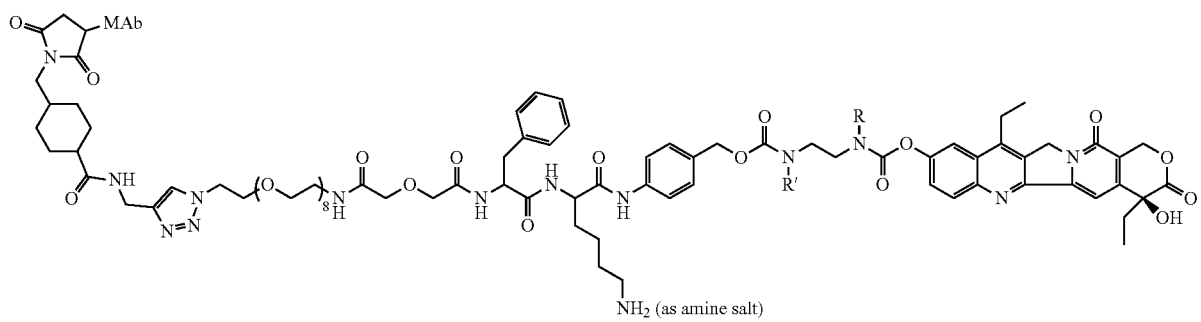

In a preferred embodiment, AA comprises a polypeptide moiety, preferably a di, tri or tetrapeptide, that is cleavable by intracellular peptidase. Examples are: Ala-Leu, Leu-Ala-Leu, and Ala-Leu-Ala-Leu (SEQ ID NO:15) (Trouet et al., 1982).

In another preferred embodiment, the L1 component of the conjugate contains a defined polyethyleneglycol (PEG) spacer with 1-30 repeating monomeric units. In a further preferred embodiment, PEG is a defined PEG with 1-12 repeating monomeric units. The introduction of PEG may involve using heterobifunctionalized PEG derivatives which are available commercially. The heterobifunctional PEG may contain an azide or acetylene group. An example of a heterobifunctional defined PEG containing 8 repeating monomeric units, with 'NETS' being succinimidyl, is given below in formula 8:

(8)

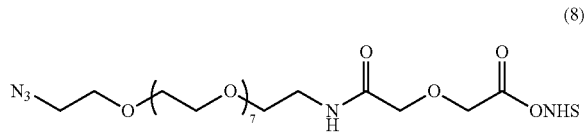

In a preferred embodiment, L2 has a plurality of acetylene (or azide) groups, ranging from 2-40, but preferably 2-20, and more preferably 2-5, and a single targeting vector-binding moiety.

A representative SN-38 conjugate of an antibody containing multiple drug molecules and a single targeting vector-binding moiety is shown below. The 12' component of this structure is appended to 2 acetylenic groups, resulting in the attachment of two azide-appended SN-38 molecules. The bonding to MAb is represented as a succinimide.

(cyanomorpholino-DOX), 2-pyrrolino-doxorubicin (2-PDOX), CPT, 10-hydroxy camptothecin, SN-38, topotecan, lurtotecan, 9-aminocamptothecin, 9-nitrocamptothecin, taxanes, geldanamycin, ansamycins, and epothilones. In a more preferred embodiment, the chemotherapeutic moiety is SN-38. Preferably, in the conjugates of the preferred embodiments, the targeting moiety links to at least one chemotherapeutic moiety; preferably 1 to about 12 chemotherapeutic moieties; most preferably about 6 to about 12 chemotherapeutic moieties.

Furthermore, in a preferred embodiment, the linker component 12' comprises a thiol group that reacts with a thiol-reactive residue introduced at one or more lysine side chain amino groups of said targeting moiety. In such cases, the antibody is pre-derivatized with a thiol-reactive group such as a maleimide, vinylsulfone, bromoacetamide, or iodoacetamide by procedures well described in the art.

(9)

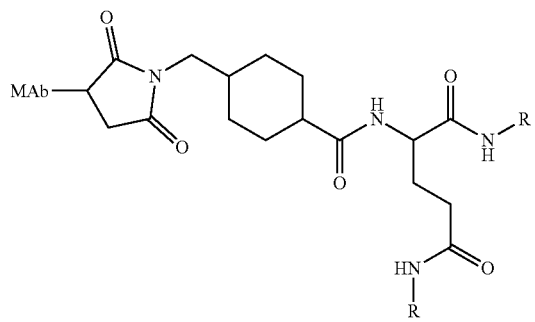

Where R residue is:

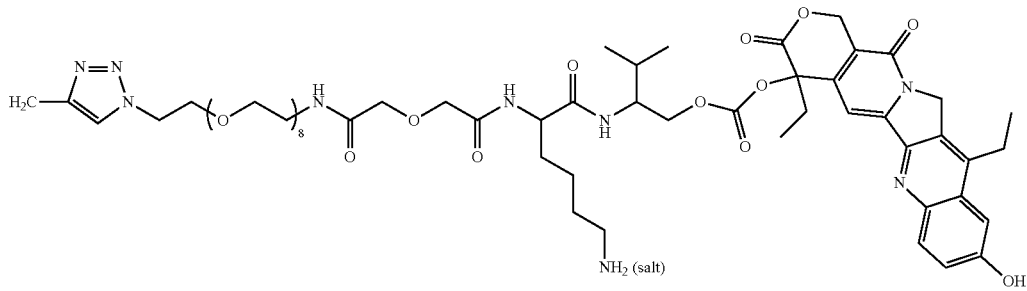

In preferred embodiments, when the bifunctional drug contains a thiol-reactive moiety as the antibody-binding group, the thiols on the antibody are generated on the lysine groups of the antibody using a thiolating reagent. Methods for introducing thiol groups onto antibodies by modifications of MAb's lysine groups are well known in the art (Wong in Chemistry of protein conjugation and cross-linking, CRC Press, Inc., Boca Raton, Fla. (1991), pp 20-22). Alternatively, mild reduction of interchain disulfide bonds on the antibody (Willner et al., *Bioconjugate Chem.* 4:521-527 (1993)) using reducing agents such as dithiothreitol (DTT) can generate 7-to-10 thiols on the antibody; which has the advantage of incorporating multiple drug moieties in the interchain region of the MAb away from the antigen-binding region.

In a preferred embodiment, the preferred chemotherapeutic moiety is selected from the group consisting of doxorubicin (DOX), epirubicin, morpholinodoxorubicin (morpholino-DOX), cyanomorpholino-doxorubicin In the context of these embodiments, a process was surprisingly discovered by which CPT drug-linkers can be prepared wherein CPT additionally has a 10-hydroxyl group. This process involves, but is not limited to, the protection of the 10-hydroxyl group as a t-butyloxycarbonyl (BOC) derivative, followed by the preparation of the penultimate intermediate of the drug-linker conjugate. Usually, removal of BOC group requires treatment with strong acid such as trifluoroacetic acid (TFA). Under these conditions, the CPT 20-O-linker carbonate, containing protecting groups to be removed, is also susceptible to cleavage, thereby giving rise to unmodified CPT. In fact, the rationale for using a mildly removable methoxytrityl (MMT) protecting group for the lysine side chain of the linker molecule, as enunciated in the art, was precisely to avoid this possibility (Walker et al., 2002). It was discovered that selective removal of phenolic BOC protecting group is possible by carrying out reactions for short durations, optimally 3-to-5 minutes. Under these conditions, the predominant product was that in which the 'BOC' at 10-hydroxyl position was removed, while the carbonate at '20' position was intact.

An alternative approach involves protecting the CPT analog's 10-hydroxy position with a group other than 'BOC', such that the final product is ready for conjugation to antibodies without a need for deprotecting the 10-OH protecting group. The 10-hydroxy protecting group, which converts the 10-OH into a phenolic carbonate or a phenolic ester, is readily deprotected by physiological pH conditions or by esterases after in vivo administration of the conjugate. The faster removal of a phenolic carbonate at the 10 position vs. a tertiary carbonate at the 20 position of 10-hydroxycamptothecin under physiological condition has been described by He et al. (He et al., Bioorganic & Medicinal Chemistry 12: 4003-4008 (2004)). A 10-hydroxy protecting group on SN-38 can be 'COR' where R can be a substituted alkyl such as "$N(CH_3)_2$—$(CH_2)_n$—" where n is 1-10 and wherein the terminal amino group is optionally in the form of a quaternary salt for enhanced aqueous solubility, or a simple alkyl residue such as "$CH_3$—$(CH_2)_n$—" where n is 0-10, or it can be an alkoxy moiety such as "$CH_3$—$(CH_2)_n$—O—" where n is 0-10, or "$N(CH_3)_2$—$(CH_2)_n$—O—" where n is 2-10, or "$R_1O$—$(CH_2$—$CH_2$—$O)_n$—$CH_2$—$CH_2$—O—" where $R_1$ is ethyl or methyl and n is an integer with values of 0-10. These 10-hydroxy derivatives are readily prepared by treatment with the chloroformate of the chosen reagent, if the final derivative is to be a carbonate. Typically, the 10-hydroxy-containing camptothecin such as SN-38 is treated with a molar equivalent of the chloroformate in dimethylformamide using triethylamine as the base. Under these conditions, the 20-OH position is unaffected. For forming 10-O-esters, the acid chloride of the chosen reagent is used.

In a preferred process of the preparation of a conjugate of a drug derivative and an antibody of the general formula 2, wherein the descriptors L2, L1, AA and A-X are as described in earlier sections, the bifunctional drug moiety, [L2]-[L1]-[AA]$_m$-[A-X]-Drug is first prepared, followed by the conjugation of the bifunctional drug moiety to the targeting moiety, TM.

In a preferred process of the preparation of a conjugate of a drug derivative and an antibody of the general formula 2, wherein the descriptors L2, L1, AA and A-OH are as described in earlier sections, the bifunctional drug moiety is prepared by first linking A-OH to the C-terminus of AA via an amide bond, followed by coupling the amine end of AA to a carboxylic acid group of L1. If AA is absent (i.e. m=0), A-OH is directly attached to L1 via an amide bond. The cross-linker, [L1]-[AA]$_m$-[A-OH], is attached to drug's hydroxyl or amino group, and this is followed by attachment to the L1 moiety, by taking recourse to the reaction between azide (or acetylene) and acetylene (or azide) groups in L1 and L2 via click chemistry.

In one embodiment, the targeting moiety, TM, is a monoclonal antibody (MAb). In a further embodiment, the targeting moiety may be a multivalent and/or multispecific MAb. The targeting moiety may be a murine, chimeric, humanized, or human monoclonal antibody, and said antibody may be in intact, fragment (Fab, Fab', F(ab)$_2$, F(ab')$_2$), or sub-fragment (single-chain constructs) form, or of an IgG1, IgG2a, IgG3, IgG4, IgA isotype, or submolecules therefrom.

In a preferred embodiment, the targeting moiety is a monoclonal antibody that is reactive with an antigen or epitope of an antigen expressed on a cancer or malignant cell. The cancer cell is preferably a cell from a hematopoietic tumor, carcinoma, sarcoma, melanoma or a glial tumor. A preferred malignancy to be treated according to the present invention is a malignant solid tumor or hematopoietic neoplasm.

In a preferred embodiment, the intracellularly-cleavable moiety may be cleaved after it is internalized into the cell upon binding by the MAb-drug conjugate to a receptor thereof, and particularly cleaved by esterases and peptidases.

The targeting moiety is preferably an antibody (including fully human, non-human, humanized, or chimeric antibodies) or an antibody fragment (including enzymatically or recombinantly produced fragments) or binding proteins incorporating sequences from antibodies or antibody fragments. The antibodies, fragments, and binding proteins may be multivalent and multispecific or multivalent and monospecific as defined above.

General Antibody Techniques

Techniques for preparing monoclonal antibodies against virtually any target antigen are well known in the art. See, for example, Kohler and Milstein, Nature 256: 495 (1975), and Coligan et al. (eds.), CURRENT PROTOCOLS IN IMMUNOLOGY, VOL. 1, pages 2.5.1-2.6.7 (John Wiley & Sons 1991). Briefly, monoclonal antibodies can be obtained by injecting mice with a composition comprising an antigen, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A or Protein-G Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992).

After the initial raising of antibodies to the immunogen, the antibodies can be sequenced and subsequently prepared by recombinant techniques. Humanization and chimerization of murine antibodies and antibody fragments are well known to those skilled in the art, as discussed below.

The skilled artisan will realize that the claimed methods and compositions may utilize any of a wide variety of antibodies known in the art. Antibodies of use may be commercially obtained from a wide variety of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and/or have published variable region sequences and are available for use in the claimed methods and compositions. See, e.g., U.S. Pat. Nos. 7,312,318; 7,282,567; 7,151,164; 7,074,403; 7,060,802; 7,056,509; 7,049,060; 7,045,132; 7,041,803; 7,041,802; 7,041,293; 7,038,018; 7,037,498; 7,012,133; 7,001,598; 6,998,468; 6,994,976; 6,994,852; 6,989,241; 6,974,863; 6,965,018; 6,964,854; 6,962,981; 6,962,813; 6,956,107; 6,951,924; 6,949,244; 6,946,129; 6,943,020; 6,939,547; 6,921,645; 6,921,645; 6,921,533; 6,919,433; 6,919,078; 6,916,475; 6,905,681; 6,899,879; 6,893,625; 6,887,468; 6,887,466; 6,884,594; 6,881,405; 6,878,812; 6,875,580; 6,872,568; 6,867,006; 6,864,062; 6,861,511; 6,861,227; 6,861,226; 6,838,282; 6,835,549; 6,835,370; 6,824,780; 6,824,778; 6,812,206; 6,793,924; 6,783,758; 6,770,450; 6,767,711;

6,764,688; 6,764,681; 6,764,679; 6,743,898; 6,733,981; 6,730,307; 6,720,155; 6,716,966; 6,709,653; 6,693,176; 6,692,908; 6,689,607; 6,689,362; 6,689,355; 6,682,737; 6,682,736; 6,682,734; 6,673,344; 6,653,104; 6,652,852; 6,635,482; 6,630,144; 6,610,833; 6,610,294; 6,605,441; 6,605,279; 6,596,852; 6,592,868; 6,576,745; 6,572; 856; 6,566,076; 6,562,618; 6,545,130; 6,544,749; 6,534,058; 6,528,625; 6,528,269; 6,521,227; 6,518,404; 6,511,665; 6,491,915; 6,488,930; 6,482,598; 6,482,408; 6,479,247; 6,468,531; 6,468,529; 6,465,173; 6,461,823; 6,458,356; 6,455,044; 6,455,040; 6,451,310; 6,444,206; 6,441,143; 6,432,404; 6,432,402; 6,419,928; 6,413,726; 6,406,694; 6,403,770; 6,403,091; 6,395,276; 6,395,274; 6,387,350; 6,383,759; 6,383,484; 6,376,654; 6,372,215; 6,359,126; 6,355,481; 6,355,444; 6,355,245; 6,355,244; 6,346,246; 6,344,198; 6,340,571; 6,340,459; 6,331,175; 6,306,393; 6,254,868; 6,187,287; 6,183,744; 6,129,914; 6,120,767; 6,096,289; 6,077,499; 5,922,302; 5,874,540; 5,814,440; 5,798,229; 5,789,554; 5,776,456; 5,736,119; 5,716,595; 5,677,136; 5,587,459; 5,443,953, 5,525,338, the Examples section of each of which is incorporated herein by reference. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art. Isolated antibodies may be conjugated to therapeutic agents, such as camptothecins, using the techniques disclosed herein.

Chimeric and Humanized Antibodies

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. Methods for constructing chimeric antibodies are well known in the art (e.g., Leung et al., 1994, Hybridoma 13:469).

A chimeric monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. To preserve the stability and antigen specificity of the humanized monoclonal, one or more human FR residues may be replaced by the mouse counterpart residues. Humanized monoclonal antibodies may be used for therapeutic treatment of subjects. Techniques for production of humanized monoclonal antibodies are well known in the art. (See, e.g., Jones et al., 1986, Nature, 321:522; Riechmann et al., Nature, 1988, 332:323; Verhoeyen et al., 1988, Science, 239:1534; Carter et al., 1992, Proc. Nat'l Acad. Sci. USA, 89:4285; Sandhu, Crit. Rev. Biotech., 1992, 12:437; Tempest et al., 1991, Biotechnology 9:266; Singer et al., J. Immun., 1993, 150:2844.)

Other embodiments may concern non-human primate antibodies. General techniques for raising therapeutically useful antibodies in baboons may be found, for example, in Goldenberg et al., WO 91/11465 (1991), and in Losman et al., Int. J. Cancer 46: 310 (1990). In another embodiment, an antibody may be a human monoclonal antibody. Such antibodies may be obtained from transgenic mice that have been engineered to produce specific human antibodies in response to antigenic challenge, as discussed below.

Human Antibodies

Methods for producing fully human antibodies using either combinatorial approaches or transgenic animals transformed with human immunoglobulin loci are known in the art (e.g., Mancini et al., 2004, *New Microbiol.* 27:315-28; Conrad and Scheller, 2005, *Comb. Chem. High Throughput Screen.* 8:117-26; Brekke and Loset, 2003, *Curr. Opin. Phamacol.* 3:544-50; each incorporated herein by reference). Such fully human antibodies are expected to exhibit even fewer side effects than chimeric or humanized antibodies and to function in vivo as essentially endogenous human antibodies. In certain embodiments, the claimed methods and procedures may utilize human antibodies produced by such techniques.

In one alternative, the phage display technique may be used to generate human antibodies (e.g., Dantas-Barbosa et al., 2005, *Genet. Mol. Res.* 4:126-40, incorporated herein by reference). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.) Recombinant Fab were cloned from the µ, γ and κ chain antibody repertoires and inserted into a phage display library (Id.) RNAs were converted to cDNAs and used to make Fab cDNA libraries using specific primers against the heavy and light chain immunoglobulin sequences (Marks et al., 1991, *J. Mol. Biol.* 222:581-97, incorporated herein by reference). Library construction was performed according to Andris-Widhopf et al. (2000, In: *Phage Display Laboratory Manual*, Barbas et al. (eds), $1^{st}$ edition, Cold Spring Harbor Laboratory Press, Cold Spring Harbor, N.Y. pp. 9.1 to 9.22, incorporated herein by reference). The final Fab fragments were digested with restriction endonucleases and inserted into the bacteriophage genome to make the phage display library. Such libraries may be screened by standard phage display methods. The skilled artisan will realize that this technique is exemplary only and any known method for making and screening human antibodies or antibody fragments by phage display may be utilized.

In another alternative, transgenic animals that have been genetically engineered to produce human antibodies may be used to generate antibodies against essentially any immunogenic target, using standard immunization protocols as discussed above. Methods for obtaining human antibodies from transgenic mice are described by Green et al., Nature Genet. 7:13 (1994), Lonberg et al., Nature 368:856 (1994), and Taylor et al., Int. Immun. 6:579 (1994). A non-limiting example of such a system is the XenoMouse® (e.g., Green et al., 1999, *J. Immunol. Methods* 231:11-23, incorporated herein by reference) from Abgenix (Fremont, Calif.). In the XenoMouse® and similar animals, the mouse antibody genes have been inactivated and replaced by functional human antibody genes, while the remainder of the mouse immune system remains intact.

The XenoMouse® was transformed with germline-configured YACs (yeast artificial chromosomes) that contained portions of the human IgH and Ig kappa loci, including the majority of the variable region sequences, along accessory genes and regulatory sequences. The human variable region repertoire may be used to generate antibody producing B cells, which may be processed into hybridomas by known techniques. A XenoMouse® immunized with a target antigen will produce human antibodies by the normal immune response, which may be harvested and/or produced by standard techniques discussed above. A variety of strains of XenoMouse® are available, each of which is capable of producing a different class of antibody. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XenoMouse® system but may utilize any transgenic animal that has been genetically engineered to produce human antibodies.

Production of Antibody Fragments

Some embodiments of the claimed methods and/or compositions may concern antibody fragments. Such antibody fragments may be obtained, for example, by pepsin or papain digestion of whole antibodies by conventional methods. For example, antibody fragments may be produced by enzymatic cleavage of antibodies with pepsin to provide a 5S fragment denoted F(ab')$_2$. This fragment may be further cleaved using a thiol reducing agent and, optionally, a blocking group for the sulfhydryl groups resulting from cleavage of disulfide linkages, to produce 3.5S Fab' monovalent fragments. Alternatively, an enzymatic cleavage using pepsin produces two monovalent Fab fragments and an Fc fragment. Exemplary methods for producing antibody fragments are disclosed in U.S. Pat. Nos. 4,036,945; 4,331,647; Nisonoff et al., 1960, Arch. Biochem. Biophys., 89:230; Porter, 1959, Biochem. J., 73:119; Edelman et al., 1967, METHODS IN ENZYMOLOGY, page 422 (Academic Press), and Coligan et al. (eds.), 1991, CURRENT PROTOCOLS IN IMMUNOLOGY, (John Wiley & Sons).

Other methods of cleaving antibodies, such as separation of heavy chains to form monovalent light-heavy chain fragments, further cleavage of fragments or other enzymatic, chemical or genetic techniques also may be used, so long as the fragments bind to the antigen that is recognized by the intact antibody. For example, Fv fragments comprise an association of $V_H$ and $V_L$ chains. This association can be noncovalent, as described in Inbar et al., 1972, Proc. Nat'l. Acad. Sci. USA, 69:2659. Alternatively, the variable chains may be linked by an intermolecular disulfide bond or cross-linked by chemicals such as glutaraldehyde. See Sandhu, 1992, Crit. Rev. Biotech., 12:437.

Preferably, the Fv fragments comprise $V_H$ and $V_L$ chains connected by a peptide linker. These single-chain antigen binding proteins (scFv) are prepared by constructing a structural gene comprising DNA sequences encoding the $V_H$ and $V_L$ domains, connected by an oligonucleotides linker sequence. The structural gene is inserted into an expression vector that is subsequently introduced into a host cell, such as E. coli. The recombinant host cells synthesize a single polypeptide chain with a linker peptide bridging the two V domains. Methods for producing scFvs are well-known in the art. See Whitlow et al., 1991, Methods: A Companion to Methods in Enzymology 2:97; Bird et al., 1988, Science, 242:423; U.S. Pat. No. 4,946,778; Pack et al., 1993, Bio/Technology, 11:1271, and Sandhu, 1992, Crit. Rev. Biotech., 12:437.

Another form of an antibody fragment is a single-domain antibody (dAb), sometimes referred to as a single chain antibody. Techniques for producing single-domain antibodies are well known in the art (see, e.g., Cossins et al., Protein Expression and Purification, 2007, 51:253-59; Shuntao et al., Molec Immunol 2006, 43:1912-19; Tanha et al., J. Biol. Chem. 2001, 276:24774-780). Other types of antibody fragments may comprise one or more complementarity-determining regions (CDRs). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See Larrick et al., 1991, Methods: A Companion to Methods in Enzymology 2:106; Ritter et al. (eds.), 1995, MONOCLONAL ANTIBODIES: PRODUCTION, ENGINEERING AND CLINICAL APPLICATION, pages 166-179 (Cambridge University Press); Birch et al., (eds.), 1995, MONOCLONAL ANTIBODIES: PRINCIPLES AND APPLICATIONS, pages 137-185 (Wiley-Liss, Inc.)

Antibody Variations

In certain embodiments, the sequences of antibodies, such as the Fc portions of antibodies, may be varied to optimize the physiological characteristics of the conjugates, such as the half-life in serum. Methods of substituting amino acid sequences in proteins are widely known in the art, such as by site-directed mutagenesis (e.g. Sambrook et al., Molecular Cloning, A laboratory manual, 2nd Ed, 1989). In preferred embodiments, the variation may involve the addition or removal of one or more glycosylation sites in the Fc sequence (e.g., U.S. Pat. No. 6,254,868, the Examples section of which is incorporated herein by reference). In other preferred embodiments, specific amino acid substitutions in the Fc sequence may be made (e.g., Hornick et al., 2000, J Nucl Med 41:355-62; Hinton et al., 2006, J Immunol 176:346-56; Petkova et al. 2006, Int Immunol 18:1759-69; U.S. Pat. No. 7,217,797; each incorporated herein by reference).

Bispecific and Multispecific Antibodies

Bispecific antibodies are useful in a number of biomedical applications. For instance, a bispecific antibody with binding sites for a tumor cell surface antigen and for a T-cell surface receptor can direct the lysis of specific tumor cells by T cells. Bispecific antibodies recognizing gliomas and the CD3 epitope on T cells have been successfully used in treating brain tumors in human patients (Nitta, et al. Lancet. 1990; 355:368-371). In certain embodiments, the techniques and compositions for therapeutic agent conjugation disclosed herein may be used with bispecific or multispecific antibodies as the targeting moieties.

Numerous methods to produce bispecific or multispecific antibodies are known, as disclosed, for example, in U.S. Pat. No. 7,405,320, the Examples section of which is incorporated herein by reference. Bispecific antibodies can be produced by the quadroma method, which involves the fusion of two different hybridomas, each producing a monoclonal antibody recognizing a different antigenic site (Milstein and Cuello, Nature, 1983; 305:537-540).

Another method for producing bispecific antibodies uses heterobifunctional cross-linkers to chemically tether two different monoclonal antibodies (Staerz, et al. Nature. 1985; 314:628-631; Perez, et al. Nature. 1985; 316:354-356). Bispecific antibodies can also be produced by reduction of each of two parental monoclonal antibodies to the respective half molecules, which are then mixed and allowed to reoxidize to obtain the hybrid structure (Staerz and Bevan. Proc Natl Acad Sci USA. 1986; 83:1453-1457). Another alternative involves chemically cross-linking two or three separately purified Fab' fragments using appropriate linkers. (See, e.g., European Patent Application 0453082).

Other methods include improving the efficiency of generating hybrid hybridomas by gene transfer of distinct selectable markers via retrovirus-derived shuttle vectors into respective parental hybridomas, which are fused subsequently (DeMonte, et al. Proc Natl Acad Sci USA. 1990, 87:2941-2945); or transfection of a hybridoma cell line with expression plasmids containing the heavy and light chain genes of a different antibody.

Cognate $V_H$ and $V_L$ domains can be joined with a peptide linker of appropriate composition and length (usually consisting of more than 12 amino acid residues) to form a single-chain Fv (scFv) with binding activity. Methods of manufacturing scFvs are disclosed in U.S. Pat. Nos. 4,946,778 and 5,132,405, the Examples section of each of which is incorporated herein by reference. Reduction of the peptide linker length to less than 12 amino acid residues prevents pairing of $V_H$ and $V_L$ domains on the same chain and forces pairing of $V_H$ and $V_L$ domains with complementary domains on other chains, resulting in the formation of functional multimers. Polypeptide chains of $V_H$ and $V_L$ domains that are joined with linkers between 3 and 12 amino acid residues form predominantly dimers (termed diabodies). With linkers between 0 and 2 amino acid residues, trimers (termed triabody) and tetramers (termed tetrabody) are favored, but the exact patterns of oligomerization appear to depend on the composition as well as the orientation of V-domains ($V_H$-linker-$V_L$ or $V_L$-linker-$V_H$), in addition to the linker length.

These techniques for producing multispecific or bispecific antibodies exhibit various difficulties in terms of low yield, necessity for purification, low stability or the labor-intensiveness of the technique. More recently, a technique known as "dock and lock" (DNL) has been utilized to produce combinations of virtually any desired antibodies, antibody fragments and other effector molecules (see, e.g., U.S. Pat. Nos. 7,550,143; 7,521,056; 7,534,866; 7,527,787 and U.S. Ser. No. 11/925,408, the Examples section of each of which incorporated herein by reference). The technique utilizes complementary protein binding domains, referred to as anchoring domains (AD) and dimerization and docking domains (DDD), which bind to each other and allow the assembly of complex structures, ranging from dimers, trimers, tetramers, quintamers and hexamers. These form stable complexes in high yield without requirement for extensive purification. The DNL technique allows the assembly of monospecific, bispecific or multispecific antibodies. Any of the techniques known in the art for making bispecific or multispecific antibodies may be utilized in the practice of the presently claimed methods.

In various embodiments, a conjugate as disclosed herein may be part of a composite, multispecific antibody. Such antibodies may contain two or more different antigen binding sites, with differing specificities. The multispecific composite may bind to different epitopes of the same antigen, or alternatively may bind to two different antigens. Some of the more preferred target combinations include those listed in Table 1. This is a list of examples of preferred combinations, but is not intended to be exhaustive.

TABLE 1

Some Examples of multispecific antibodies.

| First target | Second target |
|---|---|
| MIF | A second proinflammatory effector cytokine, especially HMGB-1, TNF-α, IL-1, or IL-6 |
| MIF | Proinflammatory effector chemokine, especially MCP-1, RANTES, MIP-1A, or MIP-1B |
| MIF | Proinflammatory effector receptor, especially IL-6R, IL-13R, and IL-15R |
| MIF | Coagulation factor, especially TF or thrombin |
| MIF | Complement factor, especially C3, C5, C3a, or C5a |
| MIF | Complement regulatory protein, especially CD46, CD55, CD59, and mCRP |
| MIF | Cancer associated antigen or receptor |
| HMGB-1 | A second proinflammatory effector cytokine, especially MIF, TNF-α, IL-1, or IL-6 |
| HMGB-1 | Proinflammatory effector chemokine, especially MCP-1, RANTES, MIP-1A, or MIP-1B |
| HMGB-1 | Proinflammatory effector receptor especially MCP-1, RANTES, MIP-1A, or MIP-1B |
| HMGB-1 | Coagulation factor, especially TF or thrombin |
| HMGB-1 | Complement factor, especially C3, C5, C3a, or C5a |
| HMGB-1 | Complement regulatory protein, especially CD46, CD55, CD59, and mCRP |
| HMGB-1 | Cancer associated antigen or receptor |
| TNF-α | A second proinflammatory effector cytokine, especially MIF, HMGB-1, TNF-α, IL-1, or IL-6 |
| TNF-α | Proinflammatory effector chemokine, especially MCP-1, RANTES, MIP-1A, or MIP-1B |
| TNF-α | Proinflammatory effector receptor, especially IL-6R IL-13R, and IL-15R |
| TNF-α | Coagulation factor, especially TF or thrombin |
| TNF-α | Complement factor, especially C3, C5, C3a, or C5a |
| TNF-α | Complement regulatory protein, especially CD46, CD55, CD59, and mCRP |
| TNF-α | Cancer associated antigen or receptor |
| LPS | Proinflammatory effector cytokine, especially MIF, HMGB-1, TNF-α, IL-1, or IL-6 |
| LPS | Proinflammatory effector chemokine, especially MCP-1, RANTES, MIP-1A, or MIP-1B |
| LPS | Proinflammatory effector receptor, especially IL-6R IL-13R, and IL-15R |
| LPS | Coagulation factor, especially TF or thrombin |

TABLE 1-continued

Some Examples of multispecific antibodies.

| First target | Second target |
| --- | --- |
| LPS | Complement factor, especially C3, C5, C3a, or C5a |
| LPS | Complement regulatory protein, especially CD46, CD55, CD59, and mCRP |
| TF or thrombin | Proinflammatory effector cytokine, especially MIF, HMGB-1, TNF-α, IL-1, or IL-6 |
| TF or thrombin | Proinflammatory effector chemokine, especially MCP-1, RANTES, MIP-1A, or MIP-1B |
| TF or thrombin | Proinflammatory effector receptor, especially IL-6R IL-13R, and IL-15R |
| TF or thrombin | Complement factor, especially C3, C5, C3a, or C5a |
| TF or thrombin | Complement regulatory protein, especially CD46, CD55, CD59, and mCRP |
| TF or thrombin | Cancer associated antigen or receptor |

Still other combinations, such as are preferred for cancer therapies, include CD20+CD22 antibodies, CD74+CD20 antibodies, CD74+CD22 antibodies, CEACAM5 (CEA)+CEACAM6 (NCA) antibodies, insulin-like growth factor (ILGF)+CEACAM5 antibodies, EGP-1 (e.g., RS-7)+ILGF antibodies, CEACAM5+EGFR antibodies. Such antibodies need not only be used in combination, but can be combined as fusion proteins of various forms, such as IgG, Fab, scFv, and the like, as described in U.S. Pat. Nos. 6,083,477; 6,183,744 and 6,962,702 and U.S. Patent Application Publication Nos. 20030124058; 20030219433; 20040001825; 20040202666; 20040219156; 20040219203; 20040235065; 20050002945; 20050014207; 20050025709; 20050079184; 20050169926; 20050175582; 20050249738; 20060014245 and 20060034759, the Examples section of each incorporated herein by reference.

Target Antigens and Exemplary Antibodies

In a preferred embodiment, antibodies are used that recognize or bind to markers or tumor-associated antigens that are expressed at high levels on target cells and that are expressed predominantly or only on diseased cells versus normal tissues, and antibodies that internalize rapidly. Antibodies useful within the scope of the present invention include MAbs with properties as described above (and show distinguishing properties of different levels of internalization into cells and microorganisms), and contemplate the use of, but are not limited to, in cancer, the following MAbs: LL1 (anti-CD74), LL2 and RFB4 (anti-CD22), RS7 (anti-epithelial glycoprotein-1 (EGP-1)), PAM4 and KC4 (both anti-mucin), MN-14 (anti-carcinoembryonic antigen (CEA, also known as CD66e), Mu-9 (anti-colon-specific antigen-p), Immu 31 (an anti-alpha-fetoprotein), TAG-72 (e.g., CC49), Tn, J591 or HuJ591 (anti-PSMA (prostate-specific membrane antigen)), AB-PG1-XG1-026 (anti-PSMA dimer), D2/B (anti-PSMA), G250 (an anti-carbonic anhydrase IX MAb) and hL243 (anti-HLA-DR). Such antibodies are known in the art (e.g., U.S. Pat. Nos. 5,686,072; 5,874,540; 6,107,090; 6,183,744; 6,306,393; 6,653,104; 6,730.300; 6,899,864; 6,926,893; 6,962,702; 7,074,403; 7,230,084; 7,238,785; 7,238,786; 7,256,004; 7,282,567; 7,300,655; 7,312,318; and U.S. Patent Application Publ. No. 20040185053; 20040202666; 20050271671; 20060193865; 20060210475; 20070087001; the Examples section of each incorporated herein by reference.) Specific known antibodies of use include hPAM4 (U.S. Pat. No. 7,282,567), hA20 (U.S. Pat. No. 7,251,164), hA19 (U.S. Pat. No. 7,109,304), hIMMU31 (U.S. Pat. No. 7,300,655), hLL1 (U.S. Pat. No. 7,312,318,), hLL2 (U.S. Pat. No. 7,074,403), hMu-9 (U.S. Pat. No. 7,387,773), hL243 (U.S. Pat. No. 7,612,180), hMN-14 (U.S. Pat. No. 6,676,924), hMN-15 (U.S. Pat. No. 7,541,440), hR1 (U.S. Provisional Patent Application 61/145,896), hRS7 (U.S. Pat. No. 7,238,785), hMN-3 (U.S. Pat. No. 7,541,440), AB-PG1-XG1-026 (U.S. patent application Ser. No. 11/983,372, deposited as ATCC PTA-4405 and PTA-4406) and D2/B (WO 2009/130575) the text of each recited patent or application is incorporated herein by reference with respect to the Figures and Examples sections.

Other useful antigens that may be targeted using the described conjugates include carbonic anhydrase IX, B7, CCCL19, CCCL21, CSAp, HER-2/neu, BrE3, CD1, CD1a, CD2, CD3, CD4, CD5, CD8, CD11A, CD14, CD15, CD16, CD18, CD19, CD20 (e.g., C2B8, hA20, 1F5 MAbs), CD21, CD22, CD23, CD25, CD29, CD30, CD32b, CD33, CD37, CD38, CD40, CD40L, CD44, CD45, CD46, CD52, CD54, CD55, CD59, CD64, CD67, CD70, CD74, CD79a, CD80, CD83, CD95, CD126, CD133, CD138, CD147, CD154, CEACAM5, CEACAM-6, alpha-fetoprotein (AFP), VEGF (e.g. AVASTIN® (bevacizumab), fibronectin splice variant), ED-B fibronectin (e.g., L19), EGP-1, EGP-2 (e.g., 17-1A), EGF receptor (ErbB1) (e.g., ERBITUX® (cetuximab)), ErbB2, ErbB3, Factor H, FHL-1, Flt-3, folate receptor, Ga 733, GROB, HMGB-1, hypoxia inducible factor (HIF), HM1.24, HER-2/neu, insulin-like growth factor (ILGF), IFN-γ, IFN-α, IFN-β, IL-2R, IL-4R, IL-6R, IL-13R, IL-15R, IL-17R, IL-18R, IL-2, IL-6, IL-8, IL-12, IL-15, IL-17, IL-18, IL-25, IP-10, IGF-1R, Ia, HM1.24, gangliosides, HCG, the HLA-DR antigen to which L243 binds, CD66 antigens, i.e., CD66a-d or a combination thereof, MAGE, mCRP, MCP-1, MIP-1A, MIP-1B, macrophage migration-inhibitory factor (MIF), MUC1, MUC2, MUC3, MUC4, MUC5, placental growth factor (P1GF), PSA (prostate-specific antigen), PSMA, PAM4 antigen, NCA-95, NCA-90, A3, A33, Ep-CAM, KS-1, Le(y), mesothelin, S100, tenascin, TAC, Tn antigen, Thomas-Friedenreich antigens, tumor necrosis antigens, tumor angiogenesis antigens, TNF-α, TRAIL receptor (R1 and R2), VEGFR, RANTES, T101, as well as cancer stem cell antigens, complement factors C3, C3a, C3b, C5a, C5, and an oncogene product.

The CD66 antigens consist of five different glycoproteins with similar structures, CD66a-e, encoded by the carcinoembryonic antigen (CEA) gene family members, BCG, CGM6, NCA, CGM1 and CEA, respectively. These CD66 antigens (e.g., CEACAM6) are expressed mainly in granulocytes, normal epithelial cells of the digestive tract and tumor cells of various tissues. Also included as suitable targets for cancers are cancer testis antigens, such as NY-ESO-1 (Theurillat et al., Int. J. Cancer 2007; 120(11):2411-7), as well as CD79a in myeloid leukemia (Kozlov et al., Cancer Genet. Cytogenet. 2005; 163(1):62-7) and also B-cell diseases, and CD79b for non-Hodgkin's lymphoma (Poison et al., Blood 110(2):616-623), all incorporated in their entirety by reference. A number of the aforementioned antigens are disclosed in U.S. Provisional Application Ser. No. 60/426, 379, entitled "Use of Multi-specific, Non-covalent Complexes for Targeted Delivery of Therapeutics," filed Nov. 15, 2002, incorporated herein by reference. Cancer stem cells, which are ascribed to be more therapy-resistant precursor malignant cells populations (Gan, J Cell Mol. Med. 2007 Dec. 5 [Epub ahead of print]; Hill and Perris, J. Natl. Cancer Inst. 2007; 99(19:1435-40), have antigens that can be targeted in certain cancer types, such as CD133 in prostate cancer (Maitland et al., Ernst Schering Found. Sympos. Proc. 2006; 5:155-79), non-small-cell lung cancer (Donnenberg et al., J. Control Release 2007; 122(3):385-91), and glioblastoma (Beier et al., Cancer Res. 2007; 67(9):4010-5), and CD44 in colorectal cancer (Dalerba et al., Proc. Natl. Acad. Sci. USA 2007; 104(24)$_{10158}$-63), pancreatic cancer (Li et al., Cancer Res. 2007; 67(3):1030-7), and in head and neck squamous cell carcinoma (Prince et al., Proc. Natl. Acad. Sci. USA 2007; 104(3)$_{973}$-8).

In multiple myeloma therapy, suitable targeting antibodies have been described against, for example, CD38 and CD138 (Stevenson, Mol Med 2006; 12(11-12):345-346; Tassone et al., Blood 2004; 104(12):3688-96), CD74 (Stein et al., ibid.), CS1 (Tai et al., Blood 2007; October 9 (epub ahead of print), and CD40 (Tai et al., 2005; Cancer Res. 65(13):5898-5906).

A recent comprehensive analysis of suitable antigen (Cluster Designation, or CD) targets on hematopoietic malignant cells, as shown by flow cytometry and which can be a guide to selecting suitable antibodies for drug-conjugated immunotherapy, is Craig and Foon, Blood prepublished online Jan. 15, 2008; DOL 10.1182/blood-2007-11-120535, incorporated herein by reference.

In another preferred embodiment, antibodies are used that internalize rapidly and are then re-expressed, processed and presented on cell surfaces, enabling continual uptake and accretion of circulating conjugate by the cell. An example of a most-preferred antibody/antigen pair is LL1, an anti-CD74 MAb (invariant chain, class II-specific chaperone, Ii) (see, e.g., U.S. Pat. Nos. 6,653,104; 7,312,318; the Examples section of each incorporated herein by reference). The CD74 antigen is highly expressed on B-cell lymphomas (including multiple myeloma) and leukemias, certain T-cell lymphomas, melanomas, colonic, lung, and renal cancers, glioblastomas, and certain other cancers (Ong et al., Immunology 98:296-302 (1999)), as well as certain autoimmune diseases. A review of the use of CD74 antibodies in cancer is contained in Stein et al., Clin Cancer Res. 2007 Sep. 15; 13(18 Pt 2):55565-5563s, incorporated herein by reference.

The diseases that are preferably treated with anti-CD74 antibodies include, but are not limited to, non-Hodgkin's lymphoma, Hodgkin's disease, melanoma, lung, renal, colonic cancers, glioblastome multiforme, histiocytomas, myeloid leukemias, and multiple myeloma. Continual expression of the CD74 antigen for short periods of time on the surface of target cells, followed by internalization of the antigen, and re-expression of the antigen, enables the targeting LL1 antibody to be internalized along with any chemotherapeutic moiety it carries. This allows a high, and therapeutic, concentration of LL1-chemotherapeutic drug conjugate to be accumulated inside such cells. Internalized LL1-chemotherapeutic drug conjugates are cycled through lysosomes and endosomes, and the chemotherapeutic moiety is released in an active form within the target cells.

Dock-and-Lock (DNL)

In certain preferred embodiments, bispecific or multispecific antibodies may be produced using the dock-and-lock technology (see, e.g., U.S. Pat. Nos. 7,521,056; 7,550,143; 7,534,866; 7,527,787 and U.S. patent application Ser. No. 11/925,408; the Examples section of each of which is incorporated herein by reference). The DNL method exploits specific protein/protein interactions that occur between the regulatory (R) subunits of cAMP-dependent protein kinase (PKA) and the anchoring domain (AD) of A-kinase anchoring proteins (AKAPs) (Baillie et al., FEBS Letters. 2005; 579: 3264. Wong and Scott, Nat. Rev. Mol. Cell Biol. 2004; 5: 959). PKA, which plays a central role in one of the best studied signal transduction pathways triggered by the binding of the second messenger cAMP to the R subunits, was first isolated from rabbit skeletal muscle in 1968 (Walsh et al., J. Biol. Chem. 1968; 243:3763). The structure of the holoenzyme consists of two catalytic subunits held in an inactive form by the R subunits (Taylor, J. Biol. Chem. 1989; 264:8443). Isozymes of PKA are found with two types of R subunits (RI and RII), and each type has α and β isoforms (Scott, Pharmacol. Ther. 1991; 50:123). The R subunits have been isolated only as stable dimers and the dimerization domain has been shown to consist of the first 44 amino-terminal residues (Newlon et al., Nat. Struct. Biol. 1999; 6:222). Binding of cAMP to the R subunits leads to the release of active catalytic subunits for a broad spectrum of serine/threonine kinase activities, which are oriented toward selected substrates through the compartmentalization of PKA via its docking with AKAPs (Scott et al., J. Biol. Chem. 1990; 265; 21561)

Since the first AKAP, microtubule-associated protein-2, was characterized in 1984 (Lohmann et al., Proc. Natl. Acad. Sci USA. 1984; 81:6723), more than 50 AKAPs that localize to various sub-cellular sites, including plasma membrane, actin cytoskeleton, nucleus, mitochondria, and endoplasmic reticulum, have been identified with diverse structures in species ranging from yeast to humans (Wong and Scott, Nat. Rev. Mol. Cell Biol. 2004; 5:959). The AD of AKAPs for PKA is an amphipathic helix of 14-18 residues (Carr et al., J. Biol. Chem. 1991; 266:14188). The amino acid sequences of the AD are quite varied among individual AKAPs, with the binding affinities reported for RH dimers ranging from 2 to 90 nM (Alto et al., Proc. Natl. Acad. Sci. USA. 2003; 100:4445). Interestingly, AKAPs will only bind to dimeric R subunits. For human RIIα, the AD binds to a hydrophobic surface formed by the 23 amino-terminal residues (Colledge and Scott, Trends Cell Biol. 1999; 6:216). Thus, the dimerization domain and AKAP binding domain of human RIIα are both located within the same N-terminal 44 amino acid sequence (Newlon et al., Nat. Struct. Biol. 1999; 6:222; Newlon et al., EMBO J. 2001; 20:1651), which is termed the DDD herein.

We have developed a platform technology to utilize the DDD of human RIIα and the AD of a certain amino acid sequence as an excellent pair of linker modules for docking any two entities, referred to hereafter as A and B, into a noncovalent complex, which could be further locked into a stably tethered structure through the introduction of cysteine residues into both the DDD and AD at strategic positions to facilitate the formation of disulfide bonds. The general methodology of the "dock-and-lock" approach is as follows. Entity A is constructed by linking a DDD sequence to a precursor of A, resulting in a first component hereafter referred to as a. Because the DDD sequence would effect the spontaneous formation of a dimer, A would thus be composed of $a_2$. Entity B is constructed by linking an AD sequence to a precursor of B, resulting in a second component hereafter referred to as b. The dimeric motif of DDD contained in $a_2$ will create a docking site for binding to the AD sequence contained in b, thus facilitating a ready association of $a_2$ and b to form a binary, trimeric complex composed of $a_2b$. This binding event is made irreversible with a subsequent reaction to covalently secure the two entities via disulfide bridges, which occurs very efficiently based on the principle of effective local concentration because the initial binding interactions should bring the reactive thiol groups placed onto both the DDD and AD into proximity (Chmura et al., Proc. Natl. Acad. Sci. USA. 2001; 98:8480) to ligate site-specifically.

By attaching the DDD and AD away from the functional groups of the two precursors, such site-specific ligations are also expected to preserve the original activities of the two precursors. This approach is modular in nature and potentially can be applied to link, site-specifically and covalently, a wide range of substances, including peptides, proteins, antibodies, antibody fragments, and other effector moieties with a wide range of activities. Utilizing the fusion protein method of constructing AD and DDD conjugated effectors, virtually any protein or peptide may be incorporated into a DNL construct. However, the technique is not limiting and other methods of conjugation may be utilized.

A variety of methods are known for making fusion proteins, including nucleic acid synthesis, hybridization and/or amplification to produce a synthetic double-stranded nucleic acid encoding a fusion protein of interest. Such double-stranded nucleic acids may be inserted into expression vectors for fusion protein production by standard molecular biology techniques (see, e.g. Sambrook et al., Molecular Cloning, A laboratory manual, $2^{nd}$ Ed, 1989). In such preferred embodiments, the AD and/or DDD moiety may be attached to either the N-terminal or C-terminal end of an effector protein or peptide, such as an antibody or fragment. However, the skilled artisan will realize that the site of attachment of an AD or DDD moiety to an effector moiety may vary, depending on the chemical nature of the effector moiety and the part(s) of the effector moiety involved in its physiological activity. Site-specific attachment of a variety of effector moieties may be performed using techniques known in the art, such as the use of bivalent cross-linking reagents and/or other chemical conjugation techniques.

In a preferred embodiment, the fusion proteins are assembled by the dock and lock (DNL) techniques disclosed in, e.g., Rossi E A, et al., Proc Natl Acad Sci USA 2006; 103:6841-6846; U.S. Pat. Nos. 7,521,056; 7,550,143; 7,534,866; 7,527,787 and U.S. patent application Ser. No. 11/925,408; the Examples section of each of which is incorporated herein by reference. Exemplary DDD and AD sequences that may be utilized in the DNL method to form synthetic complexes are disclosed below.

DDD1

(SEQ ID NO: 1)
SHIQIPPGLTELLQGYTVEVLRQQPPDLVEFAVEYFTRLREARA

DDD2

(SEQ ID NO: 2)
CGHIQIPPGLTELLQGYTVEVLRQQPPDLVEFAVEYFTRLREARA

AD1

(SEQ ID NO: 3)
QIEYLAKQIVDNAIQQA

AD2

(SEQ ID NO: 4)
CGQIEYLAKQIVDNAIQQAGC

DNL Sequence Variants

In alternative embodiments, sequence variants of the AD and/or DDD moieties may be utilized in construction of the DNL complexes. The structure-function relationships of the AD and DDD domains have been the subject of investigation. (See, e.g., Burns-Hamuro et al., 2005, Protein Sci 14:2982-92; Carr et al., 2001, J Biol Chem 276:17332-38; Alto et al., 2003, Proc Natl Acad Sci USA 100:4445-50; Hundsrucker et al., 2006, Biochem J 396:297-306; Stokka et al., 2006, Biochem J 400:493-99; Gold et al., 2006, Mol Cell 24:383-95; Kinderman et al., 2006, Mol Cell 24:397-408.)

For example, Kinderman et al. (2006) examined the crystal structure of the AD-DDD binding interaction and concluded that the human DDD sequence contained a number of conserved amino acid residues that were important in either dimer formation or AKAP binding, underlined in SEQ ID NO:1 below. (See FIG. 1 of Kinderman et al., 2006, incorporated herein by reference.) The skilled artisan will realize that in designing sequence variants of the DDD sequence, one would desirably avoid changing any of the underlined residues, while conservative amino acid substitutions might be made for residues that are less critical for dimerization and AKAP binding.

Human DDD Sequence from Protein Kinase a (SEQ ID NO: 1)
SHIQIPPGLTELLQGYTVEVLRQQPPDLVEFAVEYFTRLREARA Alto et al. (2003) performed a bioinformatic analysis of the AD sequence of various AKAP proteins to design an RII selective AD sequence called AKAP-IS (SEQ ID NO:5), with a binding constant for DDD of 0.4 nM. The AKAP-IS sequence was designed as a peptide antagonist of AKAP binding to PKA. Residues in the AKAP-IS sequence where substitutions tended to decrease binding to DDD are underlined in SEQ ID NO:3.

AKAP-IS SEQUENCE (SEQ ID NO: 3)
QIEYLAKQIVDNAIQQA

Similarly, Gold (2006) utilized crystallography and peptide screening to develop a SuperAKAP-IS sequence (SEQ ID NO:5), exhibiting a five order of magnitude higher selectivity for the RII isoform of PKA compared with the RI isoform. Underlined residues indicate the positions of amino acid substitutions, relative to the AKAP-IS sequence, that increased binding to the DDD moiety of RIIα. In this sequence, the N-terminal Q residue is numbered as residue number 4 and the C-terminal A residue is residue number 20. Residues where substitutions could be made to affect the affinity for RIIα were residues 8, 11, 15, 16, 18, 19 and 20 (Gold et al., 2006). It is contemplated that in certain alternative embodiments, the SuperAKAP-IS sequence may be substituted for the AKAP-IS AD moiety sequence to prepare DNL constructs. Other alternative sequences that might be substituted for the AKAP-IS AD sequence are shown in SEQ ID NO:6-8. Substitutions relative to the AKAP-IS sequence are underlined. It is anticipated that, as with the AKAP-IS sequence (SEQ ID NO:3), the AD moiety may also include the additional N-terminal residues cysteine and glycine and C-terminal residues glycine and cysteine, as shown in SEQ ID NO:4.

SuperAKAP-IS (SEQ ID NO: 5)
QIEY<u>V</u>AKQIVD<u>Y</u>AI<u>H</u>QA

Alternative AKAP Sequences (SEQ ID NO: 6)
QIEY<u>K</u>AKQIVD<u>H</u>AI<u>H</u>QA (SEQ ID NO: 7)
QIEY<u>H</u>AKQIVD<u>H</u>AI<u>H</u>QA (SEQ ID NO: 8)
QIEY<u>V</u>AKQIVD<u>H</u>AI<u>H</u>QA Stokka et al. (2006) also developed peptide competitors of AKAP binding to PKA, shown in SEQ ID NO:9-11. The peptide antagonists were designated as Ht31 (SEQ ID NO:9), RIAD (SEQ ID NO:10) and PV-38 (SEQ ID NO:11). The Ht-31 peptide exhibited a greater affinity for the RII isoform of PKA, while the RIAD and PV-38 showed higher affinity for RI.

Ht31

(SEQ ID NO: 9)
DLIEEAASRIVDAVIEQVKAAGAY

MAD (SEQ ID NO: 10)
LEQYANQLADQIIKEATE

PV-38

(SEQ ID NO: 11)
FEELAWKIAKMIWSDVFQQC

Hundsrucker et al. (2006) developed still other peptide competitors for AKAP binding to PKA, with a binding constant as low as 0.4 nM to the DDD of the RII form of PKA. The sequences of various AKAP antagonistic peptides is provided in Table 1 of Hundsrucker et al. (incorporated herein by reference). Residues that were highly conserved among the AD domains of different AKAP proteins are indicated below by underlining with reference to the AKAP IS sequence. The residues are the same as observed by Alto et al. (2003), with the addition of the C-terminal alanine residue. (See FIG. 4 of Hundsrucker et al. (2006), incorporated herein by reference.) The sequences of peptide antagonists with particularly high affinities for the MI DDD sequence are shown in SEQ ID NO:12-14.

AKAP-IS (SEQ ID NO: 3)
QIEY<u>L</u>AKQIVDN<u>AI</u>QQA

AKAP7δ-wt-pep (SEQ ID NO: 12)
PEDAELVRLSKRLVENAVLKAVQQY

AKAP7δ-L304T-Pep (SEQ ID NO: 13)
PEDAELVRTSKRLVENAVLKAVQQY

AKAP7δ-L308D-Pep (SEQ ID NO: 14)
PEDAELVRLSKRDVENAVLKAVQQY

Carr et al. (2001) examined the degree of sequence homology between different AKAP-binding DDD sequences from human and non-human proteins and identified residues in the DDD sequences that appeared to be the most highly conserved among different DDD moieties. These are indicated below by underlining with reference to the human PKA RIIα DDD sequence of SEQ ID NO:1. Residues that were particularly conserved are further indicated by italics. The residues overlap with, but are not identical to those suggested by Kinderman et al. (2006) to be important for binding to AKAP proteins.

(SEQ ID NO: 1)
SH<u>I*Q*I*PP*GLT*ELL*QGYT*V*EVLR*QQ*PP*DLVE*F*AVE*YF*TR<u>L</u>REA*RA*</u>

The skilled artisan will realize that in general, those amino acid residues that are highly conserved in the DDD and AD sequences from different proteins are ones that it may be preferred to remain constant in making amino acid substitutions, while residues that are less highly conserved may be more easily varied to produce sequence variants of the AD and/or DDD sequences described herein.

Amino Acid Substitutions

In alternative embodiments, the disclosed methods and compositions may involve production and use of proteins or peptides with one or more substituted amino acid residues. For example, the DDD and/or AD sequences used to make DNL constructs may be modified as discussed above.

The skilled artisan will be aware that, in general, amino acid substitutions typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art.

For example, the hydropathic index of amino acids may be considered (Kyte & Doolittle, 1982, J. Mol. Biol., 157: 105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within ±2 is preferred, within ±1 are more preferred, and within ±0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2);

glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, Biochemistry, 13:222-245; 1978, Ann. Rev. Biochem., 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (Q) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL website at rockefeller.edu) For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. (Id.) Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded protein sequence are well known and a matter of routine experimentation for the skilled artisan, for example by the technique of site-directed mutagenesis or by synthesis and assembly of oligonucleotides encoding an amino acid substitution and splicing into an expression vector construct.

Avimers

In certain embodiments, the binding moieties described herein may comprise one or more avimer sequences. Avimers are a class of binding proteins somewhat similar to antibodies in their affinities and specificities for various target molecules. They were developed from human extracellular receptor domains by in vitro exon shuffling and phage display. (Silverman et al., 2005, Nat. Biotechnol. 23:1493-94; Silverman et al., 2006, Nat. Biotechnol. 24:220.) The resulting multidomain proteins may comprise multiple independent binding domains, that may exhibit improved affinity (in some cases sub-nanomolar) and specificity compared with single-epitope binding proteins. (Id.) In various embodiments, avimers may be attached to, for example, DDD and/or AD sequences for use in the claimed methods and compositions. Additional details concerning methods of construction and use of avimers are disclosed, for example, in U.S. Patent Application Publication Nos. 20040175756, 20050048512, 20050053973, 20050089932 and 20050221384, the Examples section of each of which is incorporated herein by reference.

Phage Display

Certain embodiments of the claimed compositions and/or methods may concern binding peptides and/or peptide mimetics of various target molecules, cells or tissues. Binding peptides may be identified by any method known in the art, including but not limiting to the phage display technique. Various methods of phage display and techniques for producing diverse populations of peptides are well known in the art. For example, U.S. Pat. Nos. 5,223,409; 5,622,699 and 6,068,829 disclose methods for preparing a phage library. The phage display technique involves genetically manipulating bacteriophage so that small peptides can be expressed on their surface (Smith and Scott, 1985, Science 228:1315-1317; Smith and Scott, 1993, Meth. Enzymol. 21:228-257). In addition to peptides, larger protein domains such as single-chain antibodies may also be displayed on the surface of phage particles (Arap et al., 1998, Science 279: 377-380).

Targeting amino acid sequences selective for a given organ, tissue, cell type or target molecule may be isolated by panning (Pasqualini and Ruoslahti, 1996, Nature 380:364-366; Pasqualini, 1999, The Quart. J. Nucl. Med. 43:159-162). In brief, a library of phage containing putative targeting peptides is administered to an intact organism or to isolated organs, tissues, cell types or target molecules and samples containing bound phage are collected. Phage that bind to a target may be eluted from a target organ, tissue, cell type or target molecule and then amplified by growing them in host bacteria.

In certain embodiments, the phage may be propagated in host bacteria between rounds of panning. Rather than being lysed by the phage, the bacteria may instead secrete multiple copies of phage that display a particular insert. If desired, the amplified phage may be exposed to the target organs, tissues, cell types or target molecule again and collected for additional rounds of panning. Multiple rounds of panning may be performed until a population of selective or specific binders is obtained. The amino acid sequence of the peptides may be determined by sequencing the DNA corresponding to the targeting peptide insert in the phage genome. The identified targeting peptide may then be produced as a synthetic peptide by standard protein chemistry techniques (Arap et al., 1998, Smith et al., 1985).

In some embodiments, a subtraction protocol may be used to further reduce background phage binding. The purpose of subtraction is to remove phage from the library that bind to targets other than the target of interest. In alternative embodiments, the phage library may be prescreened against a control cell, tissue or organ. For example, tumor-binding peptides may be identified after prescreening a library against a control normal cell line. After subtraction the library may be screened against the molecule, cell, tissue or organ of interest. Other methods of subtraction protocols are known and may be used in the practice of the claimed methods, for example as disclosed in U.S. Pat. Nos. 5,840,841, 5,705,610, 5,670,312 and 5,492,807.

Aptamers

In certain embodiments, a targeting moiety of use may be an aptamer. Methods of constructing and determining the binding characteristics of aptamers are well known in the art. For example, such techniques are described in U.S. Pat. Nos. 5,582,981, 5,595,877 and 5,637,459, the Examples section of each incorporated herein by reference. Methods for preparation and screening of aptamers that bind to particular targets of interest are well known, for example U.S. Pat. Nos. 5,475,096 and 5,270,163, the Examples section of each incorporated herein by reference.

Aptamers may be prepared by any known method, including synthetic, recombinant, and purification methods, and may be used alone or in combination with other ligands specific for the same target. In general, a minimum of approximately 3 nucleotides, preferably at least 5 nucleotides, are necessary to effect specific binding. Aptamers of sequences shorter than 10 bases may be feasible, although aptamers of 10, 20, 30 or 40 nucleotides may be preferred.

Aptamers may be isolated, sequenced, and/or amplified or synthesized as conventional DNA or RNA molecules. Alternatively, aptamers of interest may comprise modified oligomers. Any of the hydroxyl groups ordinarily present in aptamers may be replaced by phosphonate groups, phosphate groups, protected by a standard protecting group, or activated to prepare additional linkages to other nucleotides, or may be conjugated to solid supports. One or more phosphodiester linkages may be replaced by alternative linking groups, such as P(O)O replaced by P(O)S, P(O)NR$_2$, P(O)R, P(O)OR', CO, or CNR$_2$, wherein R is H or alkyl (1-20C) and R' is alkyl (1-20C); in addition, this group may be attached to adjacent nucleotides through O or S. Not all linkages in an oligomer need to be identical.

Conjugation Protocols

The preferred conjugation protocol is based on a thiol-maleimide, a thiol-vinylsulfone, a thiol-bromoacetamide, or a thiol-iodoacetamide reaction that are facile at neutral or acidic pH. This obviates the need for higher pH conditions for conjugations as, for instance, would be necessitated when using active esters. Further details of exemplary conjugation protocols are described below in the Examples section.

Therapeutic Treatment

In another aspect, the invention relates to a method of treating a subject, comprising administering a therapeutically effective amount of a therapeutic conjugate as described herein to a subject. Diseases that may be treated with the therapeutic conjugates described herein include, but are not limited to B-cell malignancies (e.g., non-Hodgkin's lymphoma and chronic lymphocytic leukemia using, for example LL2 MAb; see U.S. Pat. No. 6,183,744), adenocarcinomas of endodermally-derived digestive system epithelia, cancers such as breast cancer and non-small cell lung cancer, and other carcinomas, sarcomas, glial tumors, myeloid leukemias, etc. In particular, antibodies against an antigen, e.g., an oncofetal antigen, produced by or associated with a malignant solid tumor or hematopoietic neoplasm, e.g., a gastrointestinal, lung, breast, prostate, ovarian, testicular, brain or lymphatic tumor, a sarcoma or a melanoma, are advantageously used. Such therapeutics can be given once or repeatedly, depending on the disease state and tolerability of the conjugate, and can also be used optimally in combination with other therapeutic modalities, such as surgery, external radiation, radioimmunotherapy, immunotherapy, chemotherapy, antisense therapy, interference RNA therapy, gene therapy, and the like. Each combination will be adapted to the tumor type, stage, patient condition and prior therapy, and other factors considered by the managing physician.

As used herein, the term "subject" refers to any animal (i.e., vertebrates and invertebrates) including, but not limited to mammals, including humans. It is not intended that the term be limited to a particular age or sex. Thus, adult and newborn subjects, as well as fetuses, whether male or female, are encompassed by the term.

In a preferred embodiment, therapeutic conjugates comprising the Mu-9 MAb can be used to treat colorectal, as well as pancreatic and ovarian cancers as disclosed in U.S. Pat. Nos. 6,962,702 and 7,387,772, the Examples section of each incorporated herein by reference. In addition, therapeutic conjugates comprising the PAM4 MAb can be used to treat pancreatic cancer, as disclosed in U.S. Pat. Nos. 7,238,786 and 7,282,567, the Examples section of each incorporated herein by reference.

In another preferred embodiment, therapeutic conjugates comprising the RS7 MAb (binding to epithelial glycoprotein-1 [EGP-1] antigen) can be used to treat carcinomas such as carcinomas of the lung, stomach, urinary bladder, breast, ovary, uterus, and prostate, as disclosed in U.S. Pat. No. 7,238,785, the Examples section of which is incorporated herein by reference.

In another preferred embodiment, therapeutic conjugates comprising the anti-AFP MAb can be used to treat hepatocellular carcinoma, germ cell tumors, and other AFP-producing tumors using humanized, chimeric and human antibody forms, as disclosed in U.S. Pat. No. 7,300,655, the Examples section of which is incorporated herein by reference.

In another preferred embodiment, therapeutic conjugates comprising anti-tenascin antibodies can be used to treat hematopoietic and solid tumors and conjugates comprising antibodies to tenascin can be used to treat solid tumors, preferably brain cancers like glioblastomas.

In a preferred embodiment, the antibodies that are used in the treatment of human disease are human or humanized (CDR-grafted) versions of antibodies; although murine and chimeric versions of antibodies can be used. Same species IgG molecules as delivery agents are mostly preferred to minimize immune responses. This is particularly important when considering repeat treatments. For humans, a human or humanized IgG antibody is less likely to generate an anti-IgG immune response from patients. Antibodies such as hLL1 and hLL2 rapidly internalize after binding to internalizing antigen on target cells, which means that the chemotherapeutic drug being carried is rapidly internalized into cells as well. However, antibodies that have slower rates of internalization can also be used to effect selective therapy.

In another preferred embodiment, the therapeutic conjugates can be used against pathogens, since antibodies against pathogens are known. For example, antibodies and antibody fragments which specifically bind markers produced by or associated with infectious lesions, including viral, bacterial, fungal and parasitic infections, for example caused by pathogens such as bacteria, rickettsia, mycoplasma, protozoa, fungi, and viruses, and antigens and products associated with such microorganisms have been disclosed, inter alia, in Hansen et al., U.S. Pat. No. 3,927,193 and Goldenberg U.S. Pat. Nos. 4,331,647, 4,348,376, 4,361,544, 4,468,457, 4,444,744, 4,818,709 and 4,624,846, the Examples section of each incorporated herein by reference, and in Reichert and Dewitz, cited above. In a preferred embodiment, the pathogens are selected from the group consisting of HIV virus, *Mycobacterium tuberculosis, Streptococcus agalactiae*, methicillin-resistant *Staphylococcus aureus, Legionella pneumophilia, Streptococcus pyogenes, Escherichia coli, Neisseria gonorrhosae, Neisseria meningitidis, Pneumococcus, Cryptococcus neoformans, Histoplasma capsulatum, Hemophilis influenzae* B, *Treponema pallidum*, Lyme disease spirochetes, *Pseudomonas aeruginosa, Mycobacterium leprae, Brucella abortus*, rabies virus, influenza virus, cytomegalovirus, herpes simplex virus I, herpes simplex virus II, human serum parvo-like virus, respiratory syncytial virus, varicella-zoster virus, hepatitis B virus, hepatitis C virus, measles virus, adenovirus, human T-cell leukemia viruses, Epstein-Barr virus, murine leukemia virus, mumps virus, vesicular stomatitis virus, sindbis virus, lymphocytic choriomeningitis virus, wart virus, blue tongue virus, Sendai virus, feline leukemia virus, reovirus, polio virus, simian virus 40, mouse mammary tumor virus, dengue virus, rubella virus, West Nile virus, *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japanicum, Babesia bovis, Elmeria tenella, Onchocerca volvulus, Leishmania tropica, Trichinella spiralis, Theileria parva, Taenia hydatigena, Taenia ovis, Taenia saginata, Echinococcus granulosus, Mesocestoides corti, Mycoplasma arthritidis, M. hyorhinis, M. orale, M. arginini, Acholeplasma laidlawii, M. salivarium* and *M. pneumoniae*, as disclosed in U.S. Pat. No. 6,440,416, the Examples section of which is incorporated herein by reference.

In a more preferred embodiment, drug conjugates of the present invention comprising anti-gp120 and other such anti-HIV antibodies can be used as therapeutics for HIV in AIDS patients; and drug conjugates of antibodies to *Mycobacterium tuberculosis* are suitable as therapeutics for drug-refractive tuberculosis. Fusion proteins of anti-gp120 MAb (anti HIV MAb) and a toxin, such as *Pseudomonas* exotoxin, have been examined for antiviral properties (Van Oigen et al., *J Drug Target*, 5:75-91, 1998). Attempts at treating HIV infection in AIDS patients failed, possibly due to insufficient efficacy or unacceptable host toxicity. The drug conjugates of the present invention advantageously lack such toxic side effects of protein toxins, and are therefore advantageously used in treating HIV infection in AIDS patients. These drug conjugates can be given alone or in combination with other antibiotics or therapeutic agents that are effective in such patients when given alone. Candidate anti-HIV antibodies include the anti-envelope antibody described by Johansson et al. (AIDS. 2006 Oct. 3; 20(15):1911-5), as well as the anti-HIV antibodies described and sold by Polymun (Vienna, Austria), also described in U.S. Pat. Nos. 5,831,034, 5,911,989, and Vcelar et al., AIDS 2007; 21(16):2161-2170 and Joos et al., Antimicrob. Agens Chemother. 2006; 50(5): 1773-9, all incorporated herein by reference. A preferred targeting agent for HIV is various combinations of these antibodies in order to overcome resistance.

In another preferred embodiment, diseases that may be treated using the therapeutic conjugates of the preferred embodiments of the present invention include, but are not limited to immune dysregulation disease and related autoimmune diseases, including Class III autoimmune diseases such as immune-mediated thrombocytopenias, such as acute idiopathic thrombocytopenic purpura and chronic idiopathic thrombocytopenic purpura, dermatomyositis, Sjögren's syndrome, multiple sclerosis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, sarcoidosis, ulcerative colitis, erythema multiforme, IgA nephropathy, polyarteritis *nodosa*, ankylosing spondylitis, Goodpasture's syndrome, thromboangitis obliterans, Sjögren's syndrome, primary biliary cirrhosis, Hashimoto's thyroiditis, thyrotoxicosis, scleroderma, chronic active hepatitis, rheumatoid arthritis, polymyositis/dermatomyositis, polychondritis, pemphigus vulgaris, Wegener's granulomatosis, membranous nephropathy, amyotrophic lateral sclerosis, tabes *dorsalis*, giant cell arteritis/polymyalgia, pernicious anemia, rapidly progressive glomerulonephritis and fibrosing alveolitis, and also juvenile diabetes, as disclosed in U.S. Provisional Application Ser. No. 60/360,259, filed Mar. 1, 2002 (now expired). Typical antibodies useful in these diseases include, but are not limited to, those reactive with HLA-DR antigens, B-cell and plasma-cell antigens (e.g., CD19, CD20, CD21, CD22, CD23, CD4, CD5, CD8, CD14, CD15, CD19, CD20, CD21, CD22, CD23, CD25, CD33, CD37, CD38, CD40, CD40L, CD46, CD52, CD54, CD74, CD80, CD126, CD138, B7, MUC1, Ia, HM1.24, and HLA-DR), IL-6, IL-17. Since many of these autoimmune diseases are affected by autoantibodies made by aberrant B-cell populations, depletion of these B-cells by therapeutic conjugates involving such antibodies-therapeutic agent conjugates described herein is a preferred method of autoimmune disease therapy, especially when B-cell antibodies are combined, in certain circumstances, with HLA-DR antibodies and/or T-cell antibodies (including those which target IL-2 as an antigen, such as anti-TAC antibody). In a preferred embodiment, the anti-B-cell, anti-T-cell, or anti-macrophage or other such antibodies of use in the treatment of patients with autoimmune diseases also can be conjugated to result in more effective therapeutics to control the host responses involved in said autoimmune diseases, and can be given alone or in combination with other therapeutic agents, such as TNF inhibitors or TNF antibodies, unconjugated B- or T-cell antibodies, and the like.

In a preferred embodiment, a more effective incorporation into cells and pathogens can be accomplished by using multivalent, multispecific or multivalent, monospecific antibodies. Examples of such bivalent and bispecific antibodies are found in U.S. Pat. Nos. 7,387,772; 7,300,655; 7,238,785; and 7,282,567, the Examples section of each of which is incorporated herein by reference. These multivalent or multispecific antibodies are particularly preferred in the targeting of cancers and infectious organisms (pathogens), which express multiple antigen targets and even multiple epitopes of the same antigen target, but which often evade antibody targeting and sufficient binding for immunotherapy because of insufficient expression or availability of a single antigen target on the cell or pathogen. By targeting multiple antigens or epitopes, said antibodies show a higher binding and residence time on the target, thus affording a higher saturation with the drug being targeted in this invention.

In another preferred embodiment, a therapeutic agent used in combination with the camptothecin conjugate of this invention may comprise one or more isotopes. Radioactive isotopes useful for treating diseased tissue include, but are not limited to—$^{111}$In, $^{177}$Lu, $^{212}$Bi, $^{213}$Bi, $^{211}$At, $^{62}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, and $^{211}$Pb. The therapeutic radionuclide preferably has a decay-energy in the range of 20 to 6,000 keV, preferably in the ranges 60 to 200 keV for an Auger emitter, 100-2,500 keV for a beta emitter, and 4,000-6,000 keV for an alpha emitter. Maximum decay energies of useful beta-particle-emitting nuclides are preferably 20-5,000 keV, more preferably 100-4,000 keV, and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119, 1-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213 and Fm-255. Decay energies of useful alpha-particle-emitting radionuclides are preferably 2,000-10,000 keV, more preferably 3,000-8,000 keV, and most preferably 4,000-7,000 keV. Additional potential radioisotopes of use include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, 167Tm, 168Tm, $^{197}$Pt, $^{109}$Pd, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb, and the like.

Radionuclides and other metals may be delivered, for example, using chelating groups attached to an antibody or conjugate. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates, such as macrocyclic polyethers for complexing $^{223}$Ra, may be used.

Therapeutic agents of use in combination with the camptothecin conjugates described herein also include, for example, chemotherapeutic drugs such as *vinca* alkaloids, anthracyclines, epidophyllotoxins, taxanes, antimetabolites, alkylating agents, antibiotics, Cox-2 inhibitors, antimitotics, antiangiogenic and proapoptotic agents, particularly doxorubicin, methotrexate, taxol, other camptothecins, and others from these and other classes of anticancer agents, and the like. Other cancer chemotherapeutic drugs include nitrogen mustards, alkyl sulfonates, nitrosoureas, triazenes, folic acid analogs, pyrimidine analogs, purine analogs, platinum coordination complexes, hormones, and the like. Suitable chemotherapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications. Other suitable chemotherapeutic agents, such as experimental drugs, are known to those of skill in the art.

Exemplary drugs of use include, but are not limited to, 5-fluorouracil, aplidin, azaribine, anastrozole, anthracyclines, bendamustine, bleomycin, bortezomib, bryostatin-1, busulfan, calicheamycin, camptothecin, carboplatin, 10-hydroxycamptothecin, carmustine, celebrex, chlorambucil, cisplatin (CDDP), Cox-2 inhibitors, irinotecan (CPT-11), SN-38, carboplatin, cladribine, camptothecans, cyclophosphamide, cytarabine, dacarbazine, docetaxel, dactinomycin, daunorubicin, doxorubicin, 2-pyrrolinodoxorubicine (2P-DOX), cyano-morpholino doxorubicin, doxorubicin glucuronide, epirubicin glucuronide, estramustine, epidophyllotoxin, estrogen receptor binding agents, etoposide (VP16), etoposide glucuronide, etoposide phosphate, floxuridine (FUdR), 3',5'-O-dioleoyl-FudR (FUdR-dO), fludarabine, flutamide, farnesyl-protein transferase inhibitors, gemcitabine, hydroxyurea, idarubicin, ifosfamide, L-asparaginase, lenolidamide, leucovorin, lomustine, mechlorethamine, melphalan, mercaptopurine, 6-mercaptopurine, methotrexate, mitoxantrone, mithramycin, mitomycin, mitotane, navelbine, nitrosurea, plicomycin, procarbazine, paclitaxel, pentostatin, PSI-341, raloxifene, semustine, streptozocin, tamoxifen, taxol, temazolomide (an aqueous form of DTIC), transplatinum, thalidomide, thioguanine, thiotepa, teniposide, topotecan, uracil mustard, vinorelbine, vinblastine, vincristine and vinca alkaloids. Such agents may part of the conjugates described herein or may alternatively be administered in combination with the described conjugates, either prior to, simultaneously with or after the conjugate. Alternatively, one or more therapeutic naked antibodies as are known in the art may be used in combination with the described conjugates. Exemplary therapeutic naked antibodies are described in the preceding section.

Therapeutic agents that may be used in concert with the camptothecin conjugates also may comprise toxins conjugated to targeting moieties. Toxins that may be used in this regard include ricin, abrin, ribonuclease (RNase), DNase I, Staphylococcal enterotoxin-A, pokeweed antiviral protein, gelonin, diphtherin toxin, Pseudomonas exotoxin, and Pseudomonas endotoxin. (See, e.g., Pastan. et al., Cell (1986), 47:641, and Sharkey and Goldenberg, C A Cancer J Clin. 2006 July-August; 56(4):226-43.) Additional toxins suitable for use herein are known to those of skill in the art and are disclosed in U.S. Pat. No. 6,077,499.

Yet another class of therapeutic agent may comprise one or more immunomodulators. Immunomodulators of use may be selected from a cytokine, a stem cell growth factor, a lymphotoxin, a hematopoietic factor, a colony stimulating factor (CSF), an interferon (IFN), erythropoietin, thrombopoietin and a combination thereof. Specifically useful are lymphotoxins such as tumor necrosis factor (TNF), hematopoietic factors, such as interleukin (IL), colony stimulating factor, such as granulocyte-colony stimulating factor (G-CSF) or granulocyte macrophage-colony stimulating factor (GM-CSF), interferon, such as interferons-α, -β, or -γ, and stem cell growth factor, such as that designated "S1 factor". Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-α and -ß; mullerian-inhibiting substance; mouse gonadotropin-associated peptide; inhibin; activin; vascular endothelial growth factor; integrin; thrombopoietin (TPO); nerve growth factors such as NGF-ß; platelet-growth factor; transforming growth factors (TGFs) such as TGF-α and TGF-ß; insulin-like growth factor-I and —II; erythropoietin (EPO); osteoinductive factors; interferons such as interferon-α, -β, and -γ; colony stimulating factors (CSFs) such as macrophage-CSF (M-CSF); interleukins (ILs) such as IL-1, IL-1α, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21, IL-25, LIF, kit-ligand or FLT-3, angiostatin, thrombospondin, endostatin, tumor necrosis factor and LT. As used herein, the term cytokine includes proteins from natural sources or from recombinant cell culture and biologically active equivalents of the native sequence cytokines.

Chemokines of use include RANTES, MCAF, MIP1-alpha, MIP1-Beta and IP-10.

Formulation and Administration

Suitable routes of administration of the conjugates include, without limitation, oral, parenteral, rectal, transmucosal, intestinal administration, intramuscular, subcutaneous, intramedullary, intrathecal, direct intraventricular, intravenous, intravitreal, intraperitoneal, intranasal, or intraocular injections. The preferred routes of administration are parenteral. Alternatively, one may administer the compound in a local rather than systemic manner, for example, via injection of the compound directly into a solid tumor.

Immunoconjugates can be formulated according to known methods to prepare pharmaceutically useful compositions, whereby the immunoconjugate is combined in a mixture with a pharmaceutically suitable excipient. Sterile phosphate-buffered saline is one example of a pharmaceutically suitable excipient. Other suitable excipients are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The immunoconjugate can be formulated for intravenous administration via, for example, bolus injection or continuous infusion. Preferably, the antibody of the present invention is infused over a period of less than about 4 hours, and more preferably, over a period of less than about 3 hours. For example, the first 25-50 mg could be infused within 30 minutes, preferably even 15 min, and the remainder infused over the next 2-3 hrs. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Additional pharmaceutical methods may be employed to control the duration of action of the therapeutic conjugate. Control release preparations can be prepared through the use of polymers to complex or adsorb the immunoconjugate. For example, biocompatible polymers include matrices of poly (ethylene-co-vinyl acetate) and matrices of a polyanhydride copolymer of a stearic acid dimer and sebacic acid. Sherwood et al., Bio/Technology 10: 1446 (1992). The rate of release of an immunoconjugate from such a matrix depends upon the molecular weight of the immunoconjugate, the amount of immunoconjugate within the matrix, and the size of dispersed particles. Saltzman et al., Biophys. J. 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

Generally, the dosage of an administered immunoconjugate for humans will vary depending upon such factors as the patient's age, weight, height, sex, general medical condition and previous medical history. It may be desirable to provide the recipient with a dosage of immunoconjugate that is in the range of from about 1 mg/kg to 25 mg/kg as a single intravenous infusion, although a lower or higher dosage also may be administered as circumstances dictate. A dosage of 1-20 mg/kg for a 70 kg patient, for example, is 70-1,400 mg, or 41-824 mg/m$^2$ for a 1.7-m patient. The dosage may be repeated as needed, for example, once per week for 4-10 weeks, once per week for 8 weeks, or once per week for 4 weeks. It may also be given less frequently, such as every other week for several months, or monthly or quarterly for many months, as needed in a maintenance therapy.

Alternatively, an immunoconjugate may be administered as one dosage every 2 or 3 weeks, repeated for a total of at least 3 dosages. Or, twice per week for 4-6 weeks. If the dosage is lowered to approximately 200-300 mg/m$^2$ (340 mg per dosage for a 1.7-m patient, or 4.9 mg/kg for a 70 kg patient), it may be administered once or even twice weekly for 4 to 10 weeks. Alternatively, the dosage schedule may be decreased, namely every 2 or 3 weeks for 2-3 months. It has been determined, however, that even higher doses, such as 20 mg/kg once weekly or once every 2-3 weeks can be administered by slow i.v. infusion, for repeated dosing cycles. The dosing schedule can optionally be repeated at other intervals and dosage may be given through various parenteral routes, with appropriate adjustment of the dose and schedule.

In preferred embodiments, the immunoconjugates are of use for therapy of cancer. Examples of cancers include, but are not limited to, carcinoma, lymphoma, glioblastoma, melanoma, sarcoma, and leukemia, myeloma, or lymphoid malignancies. More particular examples of such cancers are noted below and include: squamous cell cancer (e.g., epithelial squamous cell cancer), Ewing sarcoma, Wilms tumor, astrocytomas, lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma multiforme, cervical cancer, ovarian cancer, liver cancer, bladder cancer, hepatoma, hepatocellular carcinoma, neuroendocrine tumors, medullary thyroid cancer, differentiated thyroid carcinoma, breast cancer, ovarian cancer, colon cancer, rectal cancer, endometrial cancer or uterine carcinoma, salivary gland carcinoma, kidney or renal cancer, prostate cancer, vulvar cancer, anal carcinoma, penile carcinoma, as well as head-and-neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

Other examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Polycythemia vera, Parathyroid Cancer, Penile Cancer, Pheochromocytoma, Pituitary Tumor, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumor, and any other hyperproliferative disease, besides neoplasia, located in an organ system listed above.

The methods and compositions described and claimed herein may be used to treat malignant or premalignant conditions and to prevent progression to a neoplastic or malignant state, including but not limited to those disorders described above. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, Basic Pathology, 2d Ed., W. B. Saunders Co., Philadelphia, pp. 68-79 (1976)).

Dysplasia is frequently a forerunner of cancer, and is found mainly in the epithelia. It is the most disorderly form of non-neoplastic cell growth, involving a loss in individual cell uniformity and in the architectural orientation of cells. Dysplasia characteristically occurs where there exists chronic irritation or inflammation. Dysplastic disorders which can be treated include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, opthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders which can be treated include, but are not limited to, benign dysproliferative disorders (e.g., benign tumors, fibrocystic conditions, tissue hypertrophy, intestinal polyps or adenomas, and esophageal dysplasia), leukoplakia, keratoses, Bowen's disease, Farmer's Skin, solar cheilitis, and solar keratosis.

In preferred embodiments, the method of the invention is used to inhibit growth, progression, and/or metastasis of cancers, in particular those listed above.

Additional hyperproliferative diseases, disorders, and/or conditions include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendroglioma, meningioma, melanoma, neuroblastoma, and retinoblastoma.

Kits

Various embodiments may concern kits containing components suitable for treating diseased tissue in a patient. Exemplary kits may contain at least one conjugated antibody or other targeting moiety as described herein. If the composition containing components for administration is not formulated for delivery via the alimentary canal, such as by oral delivery, a device capable of delivering the kit components through some other route may be included. One type of device, for applications such as parenteral delivery, is a syringe that is used to inject the composition into the body of a subject. Inhalation devices may also be used.

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions to a person using a kit for its use.

EXAMPLES

Various embodiments of the present invention are illustrated by the following examples, without limiting the scope thereof.

General

Abbreviations used below are: DCC, dicyclohexylcarbodiimide; NHS, N-hydroxysuccinimide, DMAP, 4-dimethylaminopyridine; EEDQ, 2-ethoxy-1-ethoxycarbonyl-1,2-dihydroquinoline; MMT, monomethoxytrityl; PABOH, p-aminobenzyl alcohol; PEG, polyethylene glycol; SMCC, succinimidyl 4-(N-maleimidomethyl)cyclohexane-1-carboxylate; TBAF, tetrabutylammonium fluoride; TBDMS, tert-butyldimethylsilyl chloride.

Chloroformates of hydroxy compounds in the following examples were prepared using triphosgene and DMAP according to the procedure described in Moon et al. (J. Medicinal Chem. 51:6916-6926, 2008), which is incorporated by reference. Extractive work-up refers to extraction with chloroform, dichloromethane or ethyl acetate, and washing optionally with saturated bicarbonate, water, and with saturated sodium chloride. Flash chromatography was done using 230-400 mesh silica gel and methanol-dichloromethane gradient, using up to 15% v/v methanol-dichloromethane, unless otherwise stated. Reverse phase HPLC was performed by Method A using a 7.8×300 mm C18 HPLC column, fitted with a precolumn filter, and using a solvent gradient of 100% solvent A to 100% solvent B in 10 minutes at a flow rate of 3 mL per minute and maintaining at 100% solvent B at a flow rate of 4.5 mL per minute for 5 or 10 minutes; or by Method B using a 4.6×30 mm Xbridge C18, 2.5 µm, column, fitted with a precolumn filter, using the solvent gradient of 100% solvent A to 100% of solvent B at a flow rate of 1.5 mL per minutes for 4 min and 100% of solvent B at a flow rate of 2 mL per minutes for 1 minutes. Solvent A was 0.3% aqueous ammonium acetate, pH 4.46 while solvent B was 9:1 acetonitrile-aqueous ammonium acetate (0.3%), pH 4.46. HPLC was monitored by a dual in-line absorbance detector set at 360 nm and 254 nm.

Example 1: Preparation of CL6-SN-38

CL6-SN-38 is represented in Scheme-1. Commercially available O-(2-azidoethyl)-O'—(N-diglycolyl-2-aminoethyl)heptaethyleneglycol ('PEG-$N_3$'; 227 mg) was activated with DCC (100 mg), NHS (56 mg), and a catalytic amount of DMAP in 10 mL of dichloromethane for 10 min. To this mixture was added L-valinol (46.3 mg), and the reaction mixture was stirred for 1 h at ambient temperature. Filtration, followed by solvent removal and flash chromatography yielded 214 mg of clear oily material. This intermediate (160 mg) was reacted with 10-O—BOC—SN-38-20-O-chloroformate, the latter generated from 10-O—BOC—SN-38 (123 mg) using triphosgene and DMAP. The coupling reaction was done in 4 mL of dichloromethane for 10 min, and the reaction mixture was purified by flash chromatography to obtain 130 mg (45% yield) of product as foamy material. HPLC: $t_R$ 11.80 min; electrospray mass spectrum: M+Na: m/z 1181.

The maleimide-containing acetylenic reagent, namely 4-(N-maleimidomethyl)-N-(2-propynyl)cyclohexane-1-carboxamide, required for click cycloaddition, was prepared by reacting 0.107 g of SMCC and 0.021 mL of propargylamine (0.018 g; 1.01 equiv.) in dichloromethane using 1.1 equiv. of diisopropylethylamine. After 1 h, the solvent was removed and the product was purified by flash chromatography to obtain 83 mg of the product (colorless powder). Electrospray mass spectrum showed peaks at m/e 275 (M+H) and a base peak at m/e 192 in the positive ion mode, consistent with the structure calculated for $C_{15}H_{18}N_2O_3$: 275.1390 (M+H), found: 275.1394 (exact mass).

The azido intermediate (126 mg) described above was dissolved in DMSO (1.5 mL) and water (0.4 mL), and reacted with 60 mg of 4-(N-maleimidomethyl)-N-(2-propynyl)cyclohexane-1-carboxamide and 15 mg of cuprous bromide and stirred for 30 min at ambient temperature. Flash chromatography, after work up of the reaction mixture, furnished 116 mg (75% yield) of the cycloaddition product. HPLC: $t_R$ 11.20 min; electrospray mass spectrum: M+H and M+Na at m/z 1433 and 1456, respectively. Finally, deprotection with a mixture of TFA (5 mL), dichloromethane (1 mL), anisole (0.1 mL) and water (0.05 mL), followed by precipitation with ether and subsequent flash chromatography yielded the product, CL6-SN-38, as a gummy material. HPLC: $t_R$ 9.98 min; electrospray mass spectrum: M+H and M−H (negative ion mode) at m/z 1333 and 1356, respectively.

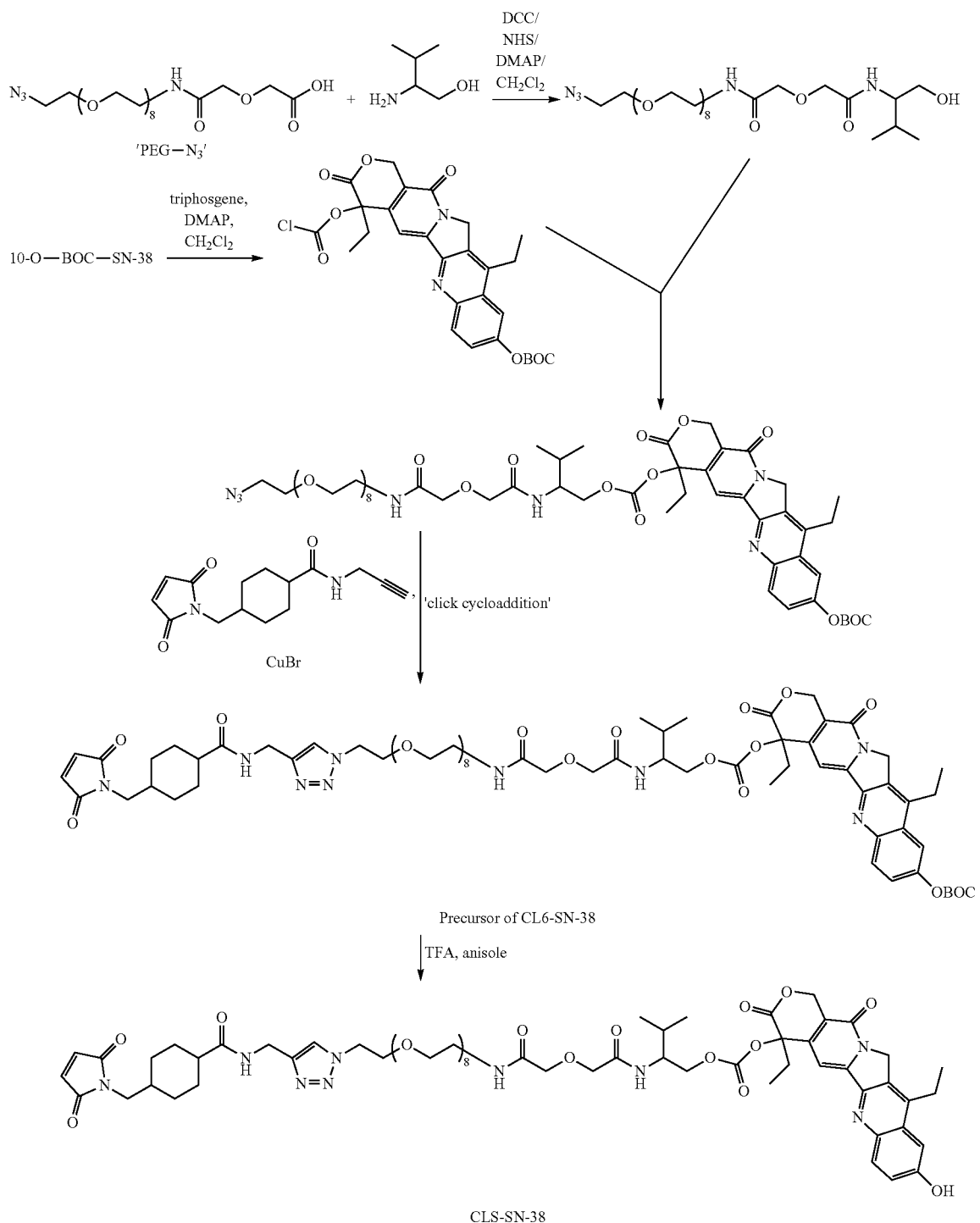

Scheme-1

Example 2: Preparation of CL7-SN-38

The synthesis is schematically shown in Scheme-2. L-Valinol (40 mg) was reacted with commercially available Fmoc-Lys(MMT)-OH (253 mg) and EEDQ (107 mg) in 10 mL of anhydrous dichloromethane at ambient temperature, under argon, for 3 h. Extractive work up followed by flash chromatography furnished the product Fmoc-Lys(MMT)-valinol as a pale yellow liquid (200 mg; ~70% yield). HPLC: $t_R$ 14.38 min; electrospray mass spectrum: M+H: m/z 727. This intermediate (200 mg) was deprotected with diethylamine (10 mL), and the product (135 mg) was obtained in ~90% purity after flash chromatography. HPLC: $t_R$ 10.91 min; electrospray mass spectrum: M+Na at m/z 527. This product (135 mg) was coupled with the commercially available O-(2-azidoethyl)-O'—(N-diglycolyl-2-aminoethyl) heptaethyleneglycol ('PEG-$N_3$'; 150 mg, 1.1 equiv.) in presence of EEDQ (72 mg, 1.1 equiv.) in 10 mL of dichloromethane, and stirred overnight at ambient temperature. The crude material was purified by flash chromatography to obtain 240 mg of the purified product as a light yellow oil (~87% yield). HPLC: $t_R$ 11.55 min; electrospray mass spectrum: M+H and M+Na at m/z 1041 and 1063, respectively.

This intermediate (240 mg) was reacted with 10-O-TBDMS-SN-38-20-O-chloroformate, the latter generated from 10-O-TBDMS-SN-38 (122 mg) using triphosgene and DMAP. The coupling reaction was done in 5 mL of dichloromethane for 10 min, and the reaction mixture was purified by flash chromatography to obtain 327 mg of product as pale yellow foam. Electrospray mass spectrum: M+H at m/z 1574. The entire product was reacted with 0.25 mmol of TBAF in 10 mL of dichloromethane for 5 min, and the reaction mixture was diluted to 100 mL and washed with brine. Crude product (250 mg) was dissolved in DMSO (2 mL) and water (0.4 mL), and reacted with 114 mg of 4-(N-maleimidomethyl)-N-(2-propynyl)cyclohexane-1-carboxamide (prepared as described in Example 1) and 30 mg of cuprous bromide and stirred for 1 h at ambient temperature. Flash chromatography furnished 150 mg of the penultimate intermediate. Finally, deprotection of the MMT group with a mixture of TFA (0.5 mL) and anisole (0.05 mL) in dichloromethane (5 mL) for 3 min, followed by purification by flash chromatography yielded 69 mg of CL7-SN-38 as a gummy material. HPLC: $t_R$ 9.60 min; electrospray mass spectrum: M+H and M−H (negative ion mode) at m/z 1461 and 1459, respectively.

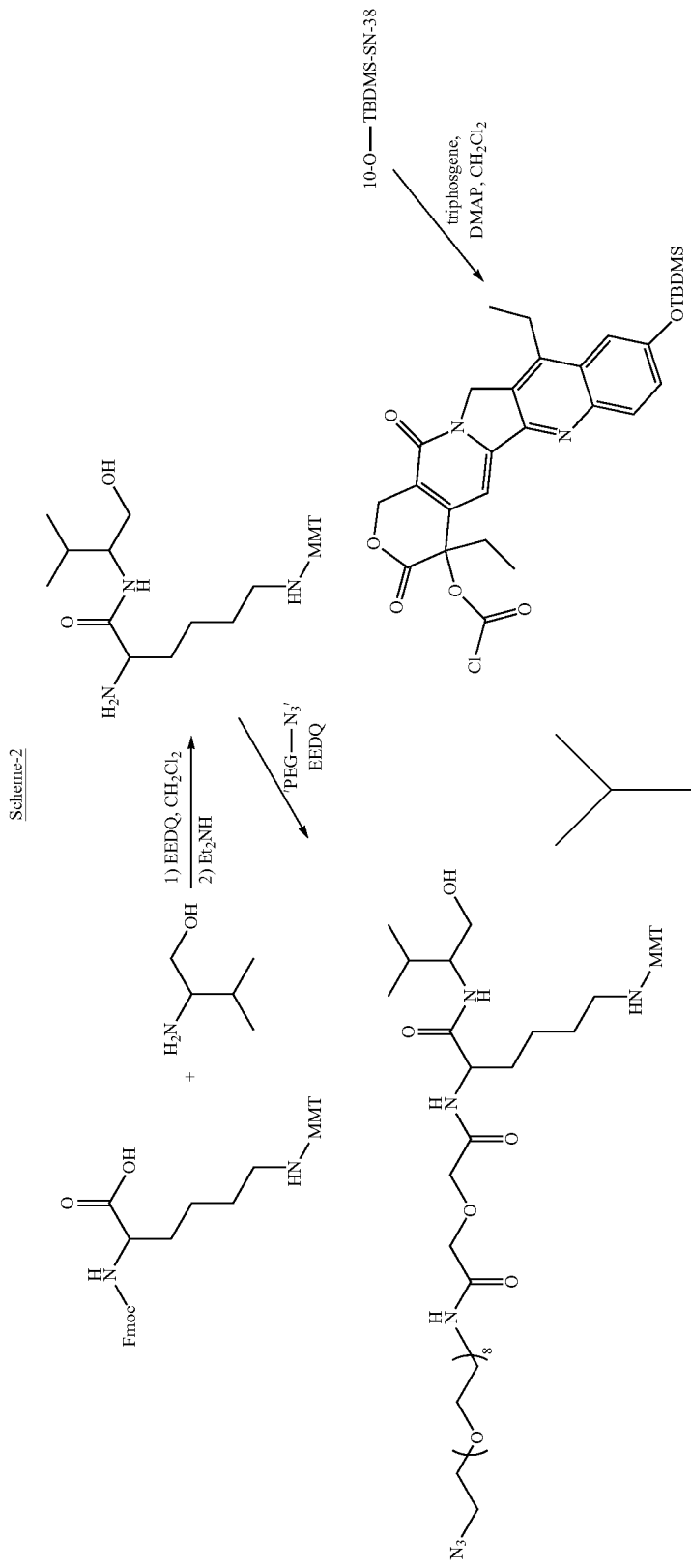

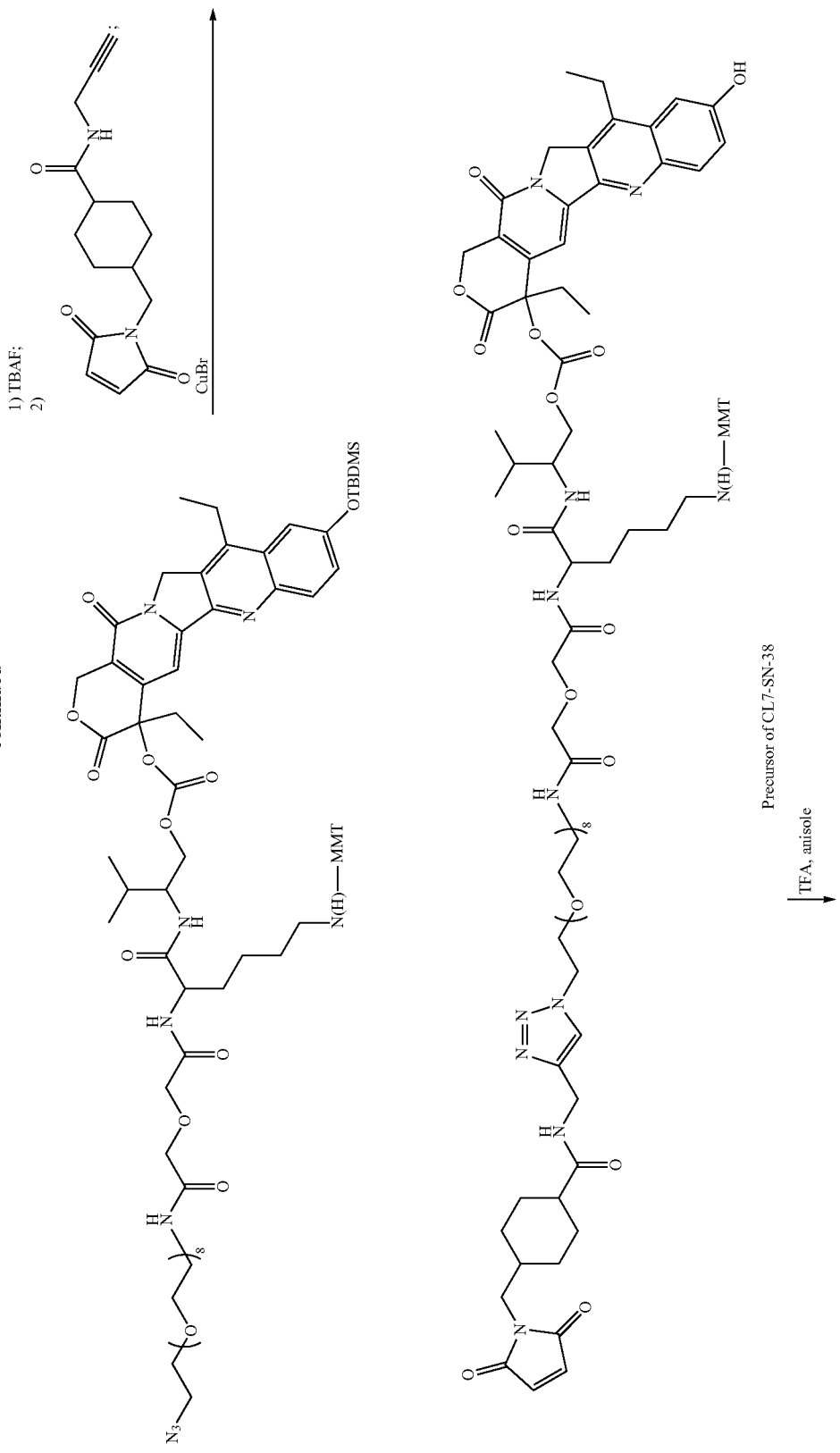
Precursor of CL7-SN-38

-continued
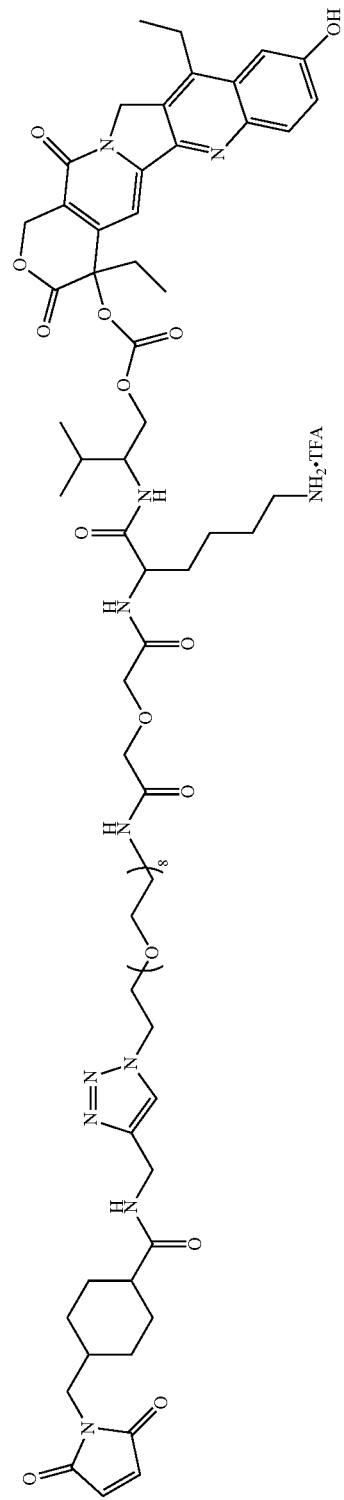
CL7-SN-38

Example 3: Preparation of CL6-SN-38-10-O—CO$_2$Et

The CL6-SN-38 of Example 1 (55.4 mg) was dissolved in dichloromethane (5 mL), and reacted with ethylchloroformate (13.1 mg; 11.5 μL) and diisopropylethylamine (52.5 mg; 71 μL), and stirred for 20 min under argon. The reaction mixture was diluted with 100 mL of dichloromethane, and washed with 100 mL each of 0.1 M HCl, half saturated sodium bicarbonate and brine, and dried. Flash chromatography, after solvent removal, furnished 59 mg of the title product. HPLC: $t_R$ 10.74 min; exact mass: calc. 1404.6457 (M+H) and 1426.6276 (M+Na); found: 1404.6464 (M+H) and 1426.6288 (M+Na).

Example 4: Preparation of CL7-SN-38-10—O—CO$_2$Et

The precursor of CL7-SN-38 of Example 2 (80 mg) was converted to the 10-O-chloroformate using the procedure and purification as described in Example 3. Yield: 60 mg. HPLC: $t_R$ 12.32 min; electrospray mass spectrum: M+H and M−H (negative ion mode) at m/z 1806 and 1804, respectively. Deprotection of this material using dichloroacetic acid and anisole in dichloromethane gave the title product. HPLC: $t_R$ 10.37 min; electrospray mass spectrum: M+H at m/z 1534.

Example 5: Preparations of CL6-SN-38-10-O—COR and CL7-SN-38-10-O—COR

This Example shows that the 10-OH group of SN-38 is protected as a carbonate or an ester, instead of as 'BOC', such that the final product is ready for conjugation to antibodies without need for deprotecting the 10-OH protecting group. This group is readily deprotected under physiological pH conditions after in vivo administration of the protein conjugate. In these conjugates, 'R' can be a substituted alkyl such as $(CH_2)_n$—$N(CH_3)_2$ where n is 2-10, or a simple alkyl such as $(CH_2)_n$—$CH_3$ where n is 0-10, or it can be an alkoxy moiety such as "$CH_3$—$(CH_2)_n$—O—" where n is 0-10, or a substituted alkoxy moiety such as such as O—$(CH_2)_n$—$N(CH_3)_2$ where n is 2-10 and wherein the terminal amino group is optionally in the form of a quaternary salt for enhanced aqueous solubility, or "$R_1O$—$(CH_2$—$CH_2$—$O)_n$—$CH_2$—$CH_2$—O—" where $R_1$ is ethyl or methyl and n is an integer with values of 0-10. In the simplest version of the latter category, R="—O—$(CH_2)_2$—$OCH_3$". These 10-hydroxy derivatives are readily prepared by treatment with the chloroformate of the chosen reagent, if the final derivative is to be a carbonate. Typically, the 10-hydroxy-containing camptothecin such as SN-38 is treated with a molar equivalent of the chloroformate in dimethylformamide using triethylamine as the base. Under these conditions, the 20-OH position is unaffected. For forming 10-O-esters, the acid chloride of the chosen reagent is used. Such derivatizations are conveniently accomplished using advanced intermediates as illustrated for simple ethyl carbonates of Examples 3 and 4.

Example 6: Preparation of CL6-Paclitaxel

Valinol is coupled to 'PEG-N3' of Scheme-1 according to the procedure described in Example 1. The product is reacted with 0.4 molar equivalent of triphosgene, 3.1 molar equivalent of DMAP, in dichloromethane. After 5 minutes, the chloroformate so formed is reacted with an equimolar amount of paclitaxel for 15 minutes at ambient temperature. The reactive 2'-hydroxyl group of paclitaxel (the side chain secondary hydroxyl group) reacts with the chloroformate of the cross-linker. The product is isolated by flash chromatography. This intermediate (0.1 mmol) is dissolved in DMSO (1.5 mL) and water (0.4 mL), and reacted with 60 mg of 4-(N-maleimidomethyl)-N-(2-propynyl)cyclohexane-1-carboxamide (prepared as described in Example 1) and 15 mg of cuprous bromide and stirred for 30 min at ambient temperature. Flash chromatography, after work up of the reaction mixture, furnishes the bifunctional paclitaxel, namely CL6-paclitaxel.

Example 7: Preparation of CL7-Paclitaxel

L-Valinol (40 mg) is reacted with commercially available Fmoc-Lys(MMT)-OH, and the product is then reacted with O-(2-azidoethyl)-O'—(N-diglycolyl-2-aminoethyl)heptaethyleneglycol (PEG-N$_3$'), as described in Example 2. The chloroformate of this derivative is formed by the method of Example-6, and reacted with an equimolar amount of paclitaxel. The reactive 2'-hydroxyl group of paclitaxel (the side chain secondary hydroxyl group) reacts with the chloroformate of the cross-linker. Click cycloaddition, using 4-(N-maleimidomethyl)-N-(2-propynyl)cyclohexane-1-carboxamide (prepared as described in Example 1) is then performed in a manner similar to that described in Example 6, and the product is finally treated with dichloroacetic acid and anisole to effect removal of the 'MMT' group under mild conditions. This process furnishes CL7-paclitaxel.

Example 8: Preparation of CL6-[Morpholino Doxorubicin]

Valinol is coupled to 'PEG-N3' of Scheme-1 according to the procedure described in Example 1. The product is reacted with 0.4 molar equivalent of triphosgene, 3.1 molar equivalent of DMAP, in dichloromethane. After 5 minutes, the chloroformate so formed is reacted with an equimolar amount of morpholino doxorubicin for 15 minutes at ambient temperature. The primary hydroxyl group of morpholino doxorubicin reacts with the chloroformate of the cross-linker. The product is isolated by flash chromatography. This intermediate (0.1 mmol) is dissolved in DMSO (1.5 mL) and water (0.4 mL), and reacted with 60 mg of 4-(N-maleimidomethyl)-N-(2-propynyl)cyclohexane-1-carboxamide (prepared as described in Example 1) and 15 mg of cuprous bromide and stirred for 30 min at ambient temperature. Flash chromatography, after work up of the reaction mixture, furnishes the bifunctional paclitaxel, namely CL6-[morpholino doxorubicin].

Example 9: Preparation of CL7-[Morpholino Doxorubicin]

L-Valinol (40 mg) is reacted with commercially available Fmoc-Lys(MMT)-OH, and the product is then reacted with O-(2-azidoethyl)-O'—(N-diglycolyl-2-aminoethyl)heptaethyleneglycol (PEG-N$_3$'), as described in Example 2. The chloroformate of this derivative is formed by the method of Example-6, and reacted with an equimolar amount of morpholino doxorubicin. The primary hydroxyl group of morpholino doxorubicin reacts with the chloroformate of the cross-linker. Click cycloaddition, using 4-(N-maleimidomethyl)-N-(2-propynyl)cyclohexane-1-carboxamide (prepared as described in Example 1) is then performed in a manner similar to that described in Example 6, and the product is finally treated with dichloroacetic acid and anisole to effect removal of the 'MMT' group under mild conditions. This process furnishes CL7-[morpholino doxorubicin].

Example 10: Preparation of CL2A-SN-38

To the mixture of commercially available Fmoc-Lys (MMT)-OH (0.943 g), p-aminobenzyl alcohol (0.190 g) in methylene choloride (10 mL) was added EEDQ (0.382 g) at room temperature and stirred for 4 h. Extractive work up followed by flash chromatograph yielded 1.051 g of material as white foam. All HPLC analyses were performed by Method B as stated in 'General' in section 0148. HPLC ret. time: 3.53 min., Electrospray mass spectrum showed peaks at m/e 745.8 (M+H) and m/e 780.3 (M+Cl−), consistent with structure. This intermediate (0.93 g) was dissolved in diethylamine (10 mL) and stirred for 2 h. After solvent removal, the residue was washed in hexane to obtain 0.6 g of the intermediate ((2) in Scheme-3) as colorless precipitate (91.6% pure by HPLC). HPLC ret. time: 2.06 min. Electrospray mass spectrum showed peaks at m/e 523.8 (M+H), m/e 546.2 (M+Na) and m/e 522.5 (M−H).

This crude intermediate (0.565 g) was coupled with commercially available O-(2-azidoethyl)-O'—(N-diglycolyl-2-aminoethyl)heptaethyleneglycol ('PEG-N3', 0.627 g) using EEDQ in methylene chloride (10 mL). Solvent removal and flash chromatography yielded 0.99 g of the product ((3) in Scheme-3; light yellow oil; 87% yield). HPLC ret. time: 2.45 min. Electrospray mass spectrum showed peaks at m/e 1061.3 (M+H), m/e 1082.7 (M+Na) and m/e 1058.8(M−H), consistent with structure. This intermediate (0.92 g) was reacted with 10-O-TBDMS-SN-38-20-O-chloroformate ((5) in Scheme-3) in methylene choloride (10 mL) for 10 min under argon. The mixture was purified by flash chromatography to obtain 0.944 g as light yellow oil ((6) in Scheme-3; yield=68%). HPLC ret. time: 4.18 min. To this intermediate (0.94 g) in methylene chloride (10 mL) was added the mixture of TBAF (1M in THF, 0.885 mL) and acetic acid (0.085 mL) in methylene chloride (3 mL), then stirred for 10 min. The mixture was diluted with methylene chloride (100 mL), washed with 0.25 M sodium citrate and brine. The solvent removal yielded 0.835 g of yellow oily product. HPLC ret. time: 2.80 min., (99% purity). Electrospray mass spectrum showed peaks at m/e 1478 (M+H), m/e 1500.6 (M+Na), m/e 1476.5 (M−H), m/e 1590.5 (M+TFA), consistent with structure.

This azido-derivatized SN-38 intermediate (0.803 g) was reacted with 4-(N-maleimidomethyl)-N-(2-propynyl)cyclohexane-1-carboxamide (0.233 g) in methylene chloride (10 mL) in presence of CuBr (0.0083 g), DIEA (0.01 mL) and triphenylphosphine (0.015 g), for 18 h. Extractive work up, including washing with and 0.1M EDTA (10 mL), and flash chromatography yielded 0.891 g as yellow foam. (yield=93%), HPLC ret. time: 2.60 min. Electrospray mass spectrum showed peaks at m/e 1753.3 (M+H), m/e 1751.6 (M−H), 1864.5 (M+TFA), consistent with structure. Finally, deprotection of the penultimate intermediate (0.22 g) with a mixture of dichloroacetic acid (0.3 mL) and anisole (0.03 mL) in methylene chloride (3 mL), followed by precipitation with ether yielded 0.18 g (97% yield) of CL2A-SN-38; (7) in Scheme-3) as light yellow powder. HPLC ret. time: 1.88 min. Electrospray mass spectrum showed peaks at m/e 1480.7 (M+H), 1478.5 (M−H), consistent with structure.

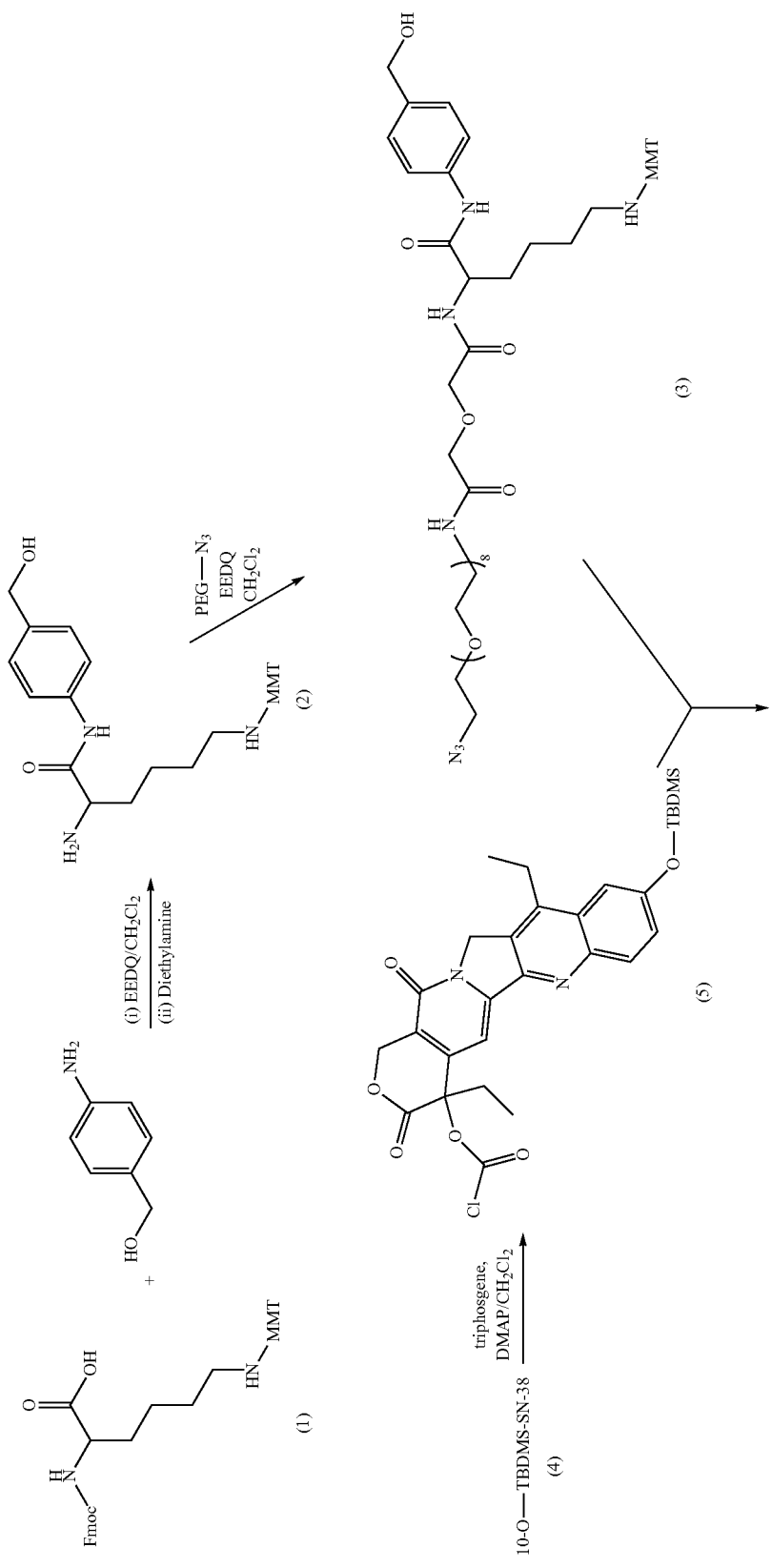

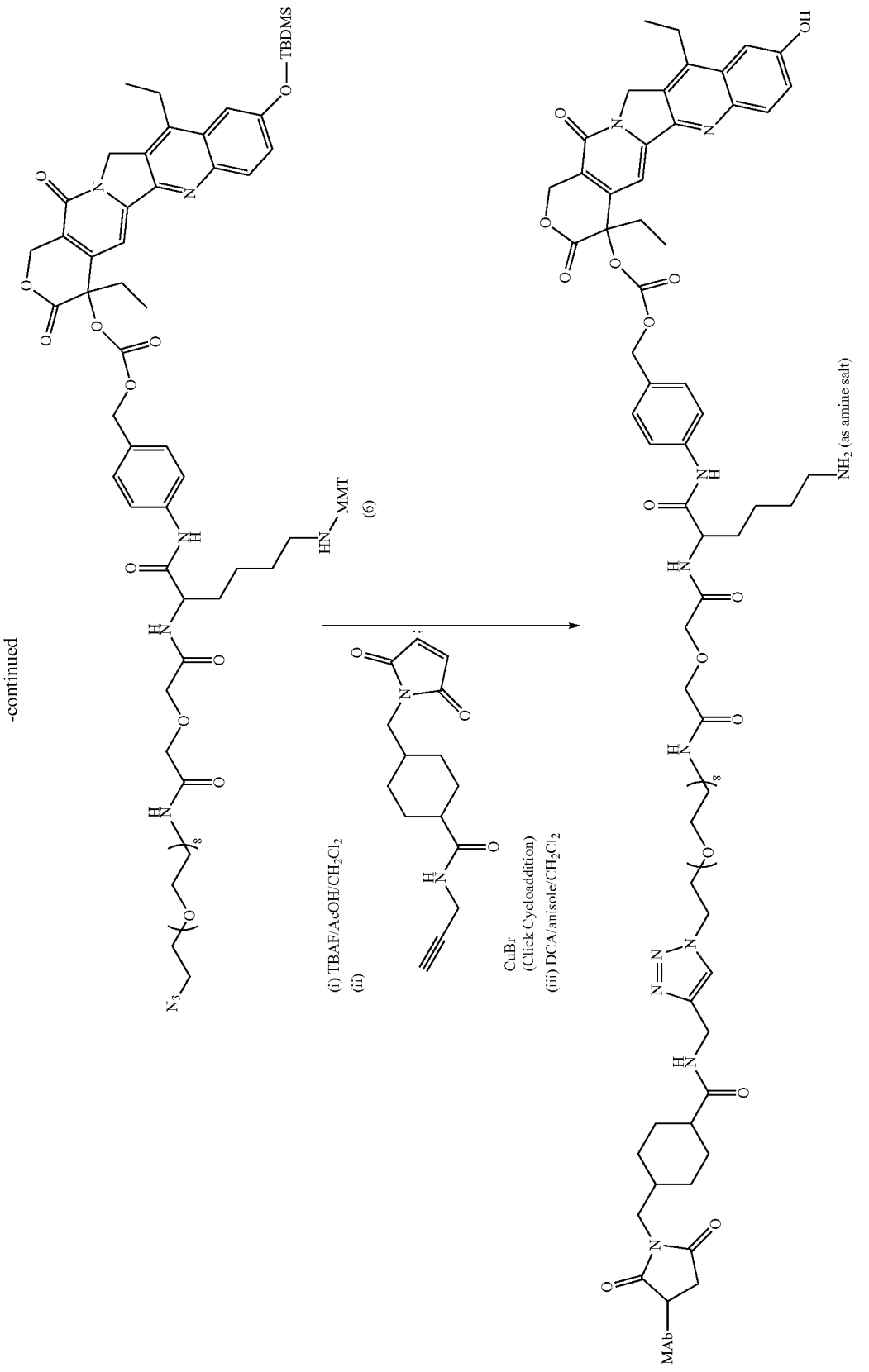

Example 11: Preparation of CL2E-SN-38

N,N'-dimethylethylenediamine (3 mL) in methylene chloride (50 mL) was reacted with monomethoxytrityl chloride (1.7 g). After 1 h of stirring, the solvent was removed under reduced pressure, and the crude product was recovered by extractive work up (yellow oil; 2.13 g). All HPLC analyses were performed by Method B as stated in 'General' in section 0148. HPLC ret. time: 2.28 min. This intermediate ((1) in Scheme-4; 0.93 g) was added in situ to activated SN-38, and the latter ((2) in Scheme-4) was prepared by reacting SN-38 (0.3 g) with p-nitrophenylchloroformate (0.185 g) and DIEA (0.293 mL) in DMF for 1 h. After removing solvent, the residue was purified on deactivated silica gel to obtain 0.442 g as white solid.

This intermediate (0.442 g) was deprotected with a mixture of trifluoroacetic acid (1 mL) and anisole (0.1 mL) in methylene chloride (5 mL), followed by precipitation with ether to obtain 0.197 g of the product ((3) in Scheme-4) as white solid. This intermediate ((3); 0.197 g) was coupled with activated azide-containingdipeptide incorporated-PEG-linker ((5) in Scheme-4), which activation was done by reacting PEG-linker ((4) in Scheme-4; 0.203 g) with bis(4-nitrophenyl) carbonate (0.153 g) and DIEA (0.044 mL) in methylene chloride (8 mL). Flash chromatography yielded 0.2 g of azide-derivatized SN-38 intermediate product ((6) in Scheme-4) as glassy solid. HPLC ret. time: 2.8 min. Electrospray mass spectrum showed peaks at m/e 1740.5 (M+H), m/e 1762.9 (M+Na), m/e 1774.9 (M+Cl$^-$), consistent with structure. This intermediate ((6) in Scheme-4; 0.2 g) was subjected to click cycloaddition with 4-(N-maleimidomethyl)-N-(2-propynyl)cyclohexane-1-carboxamide (0.067 g) in methylene chloride in presence of CuBr (0.007 g,), DIEA (0.008 mL) and triphenylphosphine (0.012 g) for 18 h. Work up of reaction mixture, which included treatment with 0.1M EDTA, followed by flash chromatography yielded 0.08 g of the penultimate intermediate as light yellow foam. HPLC: $t_R$=2.63 min. Electrospray mass spectrum showed peaks at m/e 2035.9 (M+Na$^+$), m/e 2047.9 (M+0), consistent with structure. Finally, deprotection of this intermediate (0.08 g) with a mixture of trifluoroacetic acid (0.2 mL), anisole (0.12 mL) and water (0.06 mL) in methylene chloride (2 mL), followed by precipitation with ether yielded 0.051 g of product, CL17-SN-38 (also referred to as CL2E-SN-38), as light yellow powder (yield=69%). HPLC ret. time: 1.95 min., ~99% purity. Electrospray mass spectrum showed peaks at m/e 1741.1 (M+H), 1775.5 (M+Cl$^-$), consistent with structure.

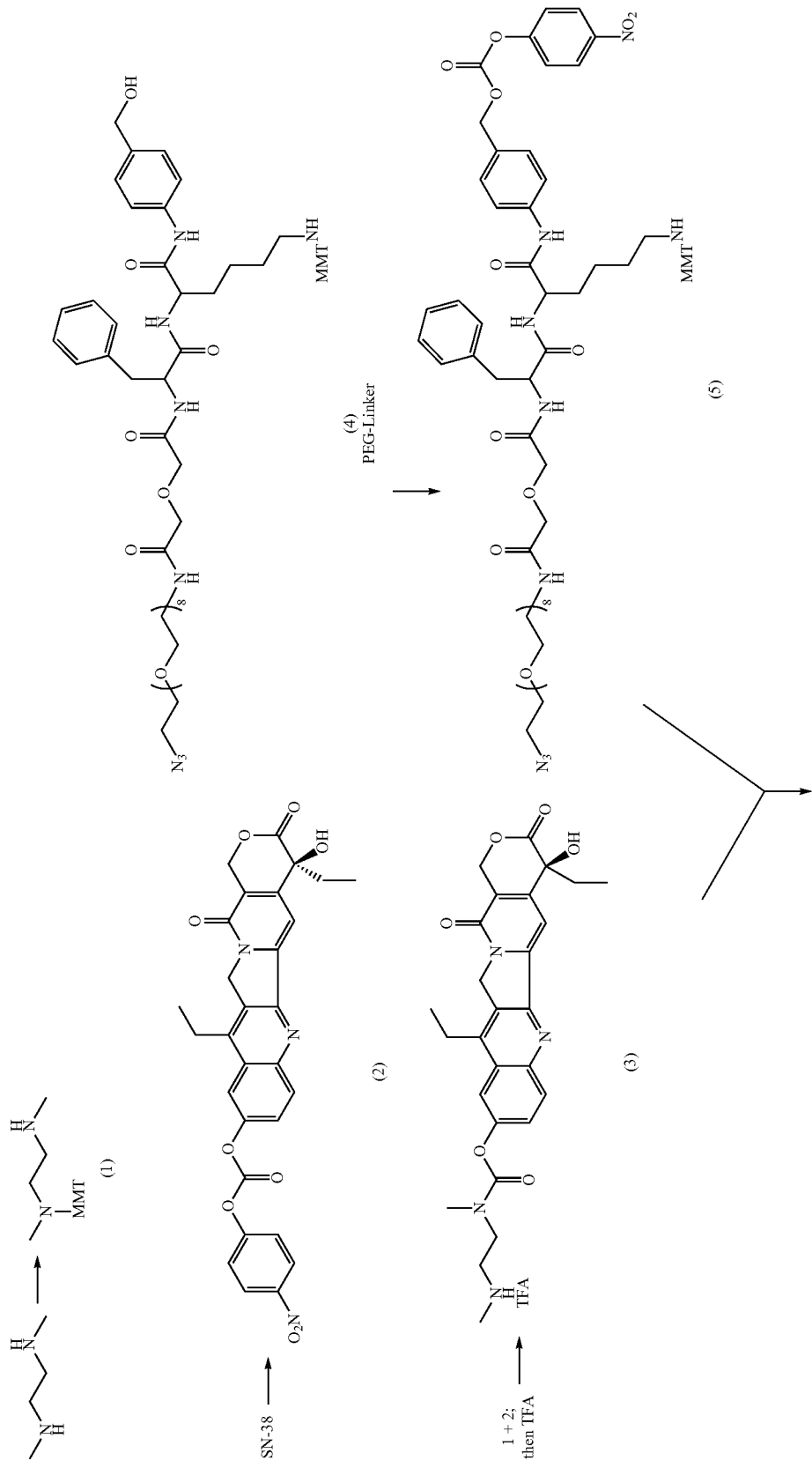
Scheme-4: Preparation of CL2E-SN-38

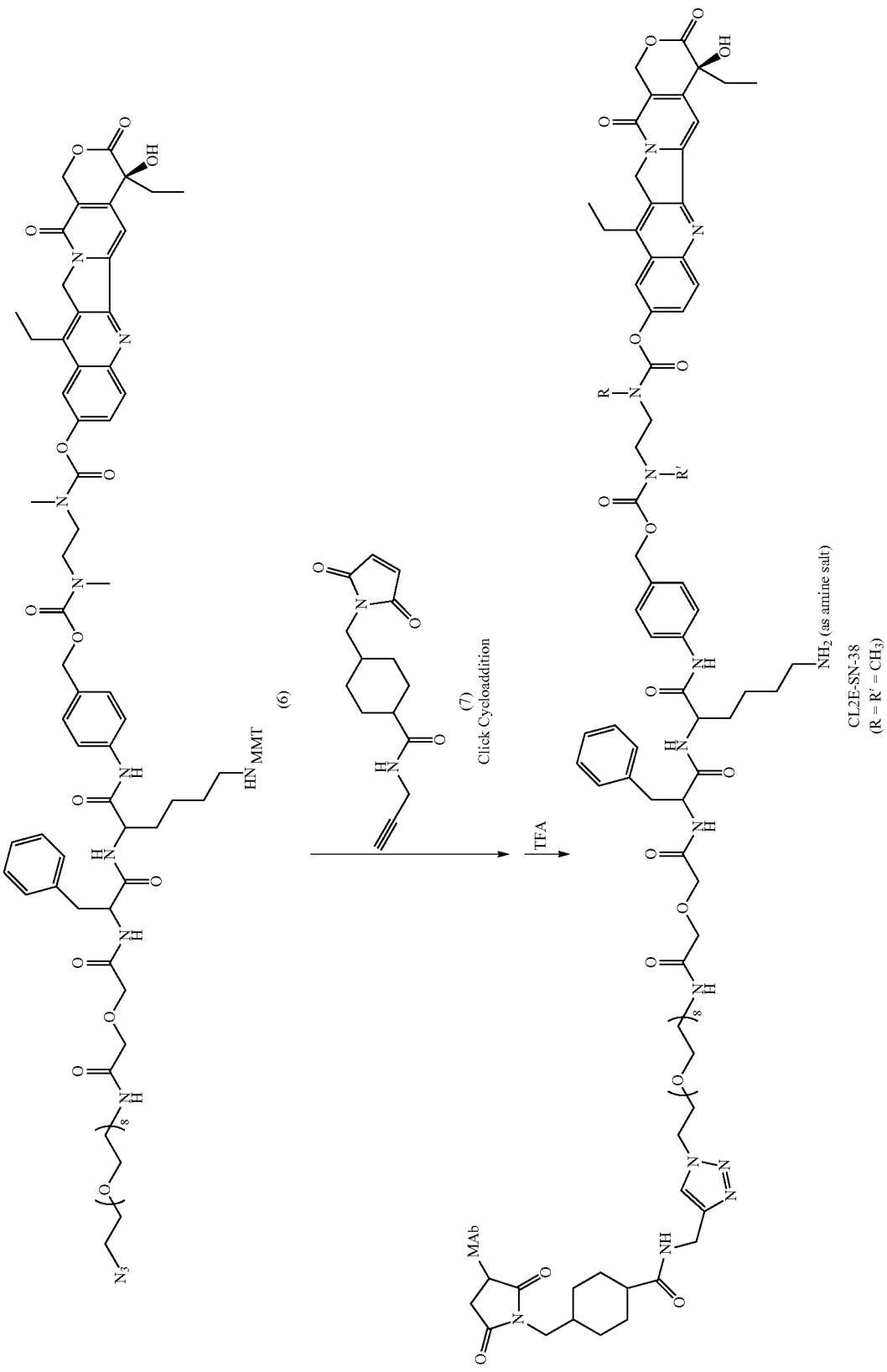

Example 12: Conjugation of Bifunctional SN-38 Products to Mildly Reduced Antibodies The anti-CEACAM5 humanized MAb, hMN-14, the anti-CD22 humanized MAb, hLL2, the anti-CD20 humanized MAb, hA20, the anti-EGP-1 humanized MAb, hRS7, and anti-mucin humanized MAb, hPAM4, were used in these studies. Each antibody was reduced with dithiothreitol (DTT), used in a 50-to-70-fold molar excess, in 40 mM PBS, pH 7.4, containing 5.4 mM EDTA, at 37° C. (bath) for 45 min. The reduced product was purified by size-exclusion chromatography and/or diafiltration, and was buffer-exchanged into a suitable buffer at pH 6.5. The thiol content was determined by Ellman's assay, and was in the 6.5-to-8.5 SH/IgG range. Alternatively, the antibodies were reduced with Tris (2-carboxyethyl) phosphine (TCEP) in phosphate buffer at pH in the range of 5-7, followed by in situ conjugation. The reduced MAb was reacted with ~10-to-15-fold molar excess of 'CL6-SN-38' of Example 1, or 'CL7-SN-38' of Example 2, or 'CL6-SN-38-10—O—$CO_2Et$' of Example 3, or 'CL7-SN-38-10—O—$CO_2Et$' of Example 4, CL2A-SN-38 of Example 10, or CL2E-SN-38 of Example 11 using DMSO at 7-15% v/v as co-solvent, and incubating for 20 min at ambient temperature. The conjugate was purified by centrifuged SEC, passage through a hydrophobic column, and finally by ultrafiltration-diafiltration. The product was assayed for SN-38 by absorbance at 366 nm and correlating with standard values, while the protein concentration was deduced from absorbance at 280 nm, corrected for spillover of SN-38 absorbance at this wavelength. This way, the SN-38/MAb substitution ratios were determined. The purified conjugates were stored as lyophilized formulations in glass vials, capped under vacuum and stored in a ~20° C. freezer. SN-38 molar substitution ratios (MSR) obtained for some of these conjugates, which were typically in the 5-to-7 range, are shown in Table 2.

TABLE 2

SN-38/MAb Molar substitution ratios (MSR) in some conjugates

| MAb | Conjugate | MSR |
|---|---|---|
| hMN-14 | hMN-14-[CL2A-SN-38], using drug-linker of Example 10 | 6.1 |
| | hMN-14-[CL6-SN-38], using drug-linker of Example 1 | 6.8 |
| | hMN-14-[CL7-SN-38], using drug-linker of Example 2 | 5.9 |
| | hMN-14-[CL7-SN-38-10-O[13 $CO_2Et$], using drug-linker of Example 4 | 5.8 |
| | hMN-14-[CL2E-SN-38], using drug-linker of Example 11 | 5.9 |
| hRS7 | hRS7-CL2A-SN-38 using drug-linker of Example 10 | 5.8 |
| | hRS7-CL7-SN-38 using drug-linker of Example 2 | 5.9 |
| | hRS7-CL7-SN-38 (Et) using drug-linker of Example 4 | 6.1 |
| hA20 | hA20-CL2A-SN-38 using drug-linker of Example 10 | 5.8 |
| hLL2 | hLL2-CL2A-SN-38 using drug-linker of Example 10 | 5.7 |
| hPAM4 | hPAM4-CL2A-SN-38 using drug-linker of Example 10 | 5.9 |

Figure 2:
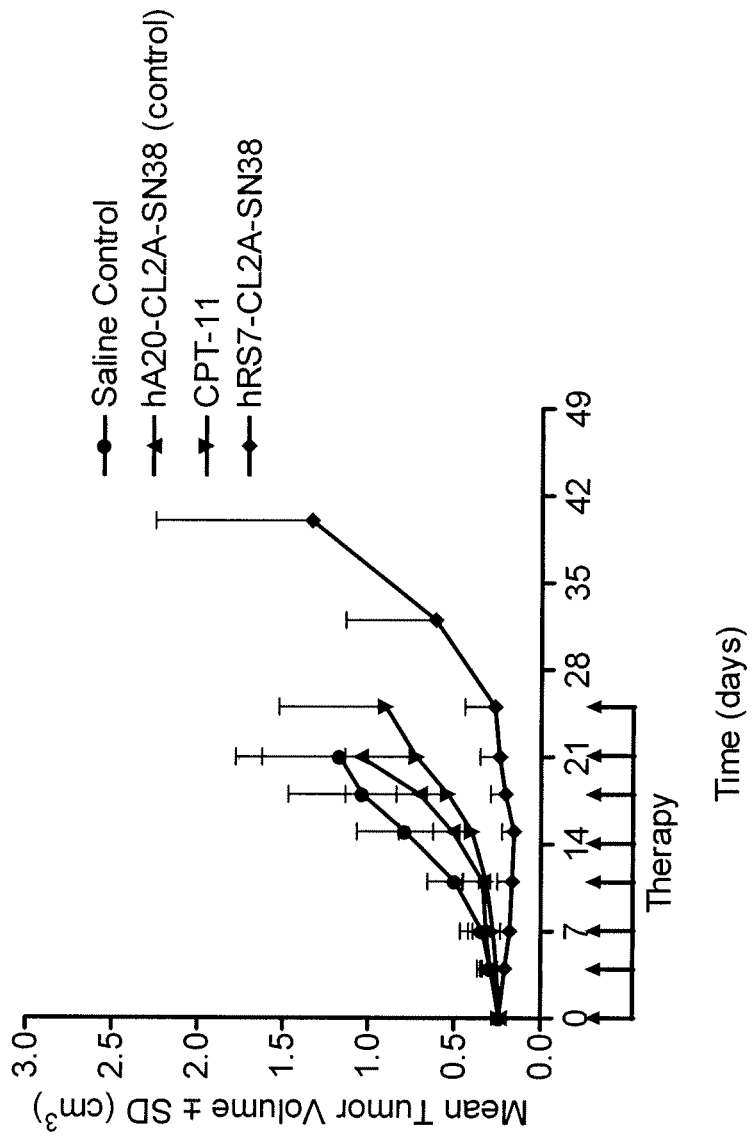
FIG. 2. Preclinical in vivo therapy of athymic nude mice, bearing BxPC3 human pancreatic carcinoma, with MAb-CL2A-SN-38 conjugates.
Figure 3:
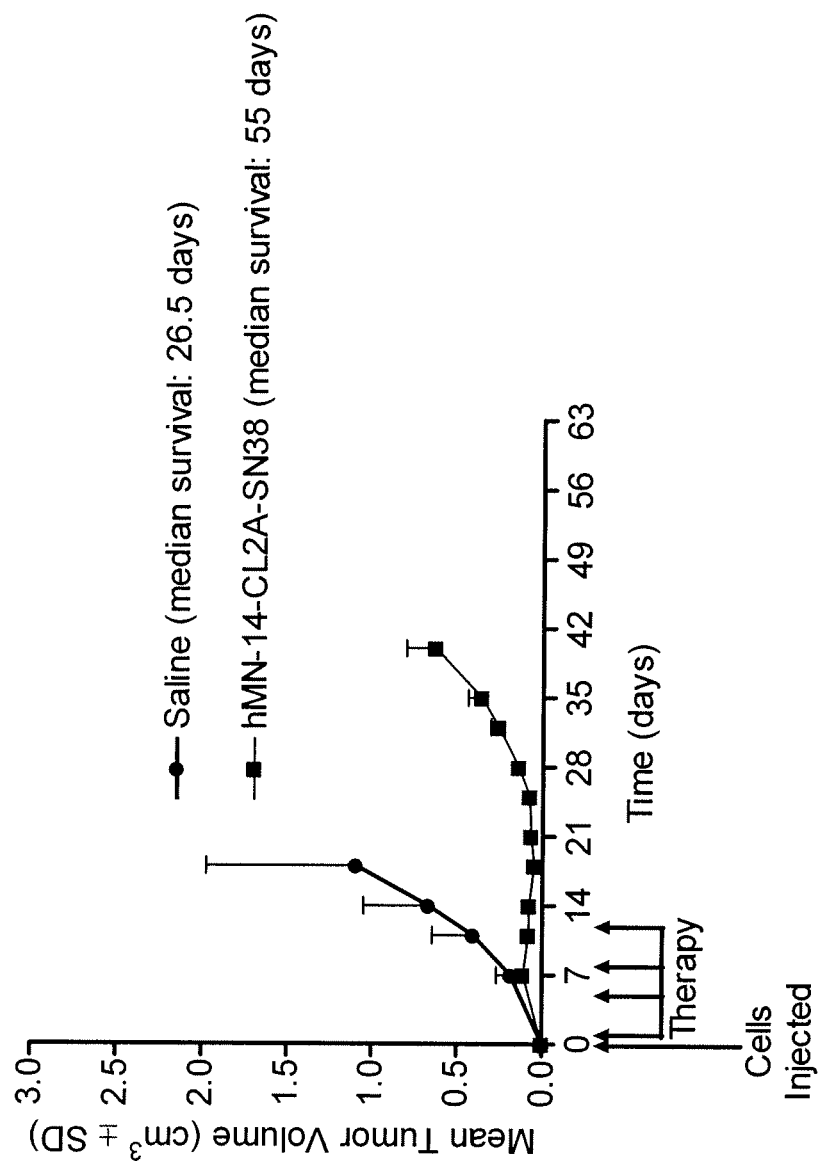
FIG. 3. Preclinical in vivo therapy of athymic nude mice, bearing LS174T huiman colon carcinoma, with hMN-14-CL2A-SN-38 conjugate.

Example 13: In Vivo Therapeutic Efficacies in Preclinical Models of Human Pancreatic or Colon Carcinoma Immune-compromised athymic nude mice (female), bearing subcutaneous human pancreatic or colon tumor xenografts were treated with either specific CL2A-SN-38 conjugate or control conjugate or were left untreated. The therapeutic efficacies of the specific conjugates were observed. FIG. 1 shows a Capan 1 pancreatic tumor model, wherein specific CL2A-SN-38 conjugates of hRS7 (anti-EGP-1), hPAM4 (anti-mucin), and hMN-14 (anti-CEACAM5) antibodies showed better efficacies than control hA20-CL2A-SN-38 conjugate (anti-CD20) and untreated control. Similarly in a BXPC3 model of human pancreatic cancer, the specific hRS7-CL2A-SN-38 showed better therapeutic efficacy than control treatments (FIG. 2). Likewise, in an aggressive LS174T model of human colon carcinoma, treatment with specific hMN-14-CL2A-SN-38 was more efficacious than non-treatment (FIG. 3).

Example 14: Elimination of HIV Infection by Treatment with an SN-38 Conjugate of an Anti-Gp120 MAb A MAb targeted to the HIV envelope protein gp120, anti-gp120 antibody such as P4/D10, is reduced using conditions described in Example 7, and the reduced MAb is reacted with a 20-fold molar excess of the drug linker CL7-SN-38, which is as described in Example 2. An anti-gp120-SN-38 conjugate with a substitution of ~8 drug molecules per antibody is obtained. An in vitro HIV-inhibition assay with said conjugate is performed by using various mixtures of uninfected Jurkat-T cells and fully HIV-infected Jurkat T-cells (in the ratios of 99.8:0.2 to 95:5), and treating with serial dilutions of the conjugate, non-specific hRS7-CL7-SN38 conjugate control, naked antibody, and HIV-negative serum from 100 to 0.00001 µg/mL. The cells so treated were incubated in RPMI 1640 culture medium at 37° C. for seven days, and then assayed for HIV inhibition by ELISA test. This experiment shows a strong and specific inhibition of intercellular spread of HIV by the specific drug conjugate. The in vivo efficacy is tested by administering to mice isologous HIV-infected cells together with specific and non-specific SN-38 conjugates. For this, primary murine splenocytes infected by HIV-1/MuLV pseudotype virus are intraperitoneally transferred to groups of mice simultaneously with immunoconjugate administration. Peritoneal cells are harvested 10 days later. While infectious HIV presence is demonstrated in control mice, no infectious HIV is detected in mice treated with 100 µg or less of anti-gp120-SN-38 conjugate. No protection is seen with mice treated with control conjugates.

From the foregoing description, one skilled in the art can easily ascertain the essential characteristics of this invention, and without departing from the spirit and scope thereof, can make various changes and modifications of the invention to adapt it to various usage and conditions without undue experimentation. All patents, patent applications and publications cited herein are incorporated by reference.

We claim:
1. A CL2A molecule, with a structure represented by:

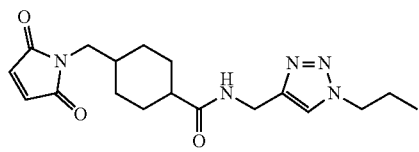

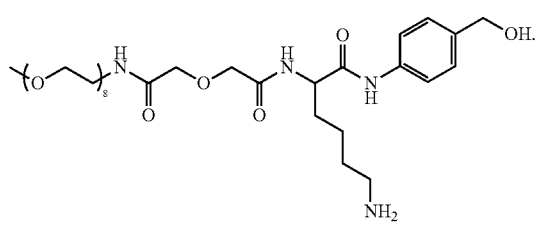

2. The CL2A molecule of claim 1, wherein the CL2A molecule comprises a lysine residue and the lysine epsilon amine group is present as the dichloroacetic acid salt.
3. The CL2A molecule of claim 1, wherein the hydroxyl residue of the para-aminobenzyl alcohol moiety is conjugated to a drug.
4. The CL2A molecule of claim 3, wherein the drug is a camptothecin or an anthracycline.
5. The CL2A molecule of claim 3, wherein the drug comprises a hydroxy moiety.
6. The CL2A molecule of claim 4, wherein the drug is SN-38.
7. The CL2A molecule of claim 3, wherein the maleimide moiety of the CL2A molecule is conjugated to a sulfhydryl group on a protein or peptide.
8. The CL2A molecule of claim 7, wherein the protein is an antibody or antibody fragment.
9. The CL2A molecule of claim 8, wherein the antibody fragment is selected from the group consisting of Fab, Fab', F(ab)$_2$, F(ab')$_2$, and scFv.
10. The CL2A molecule of claim 8, wherein the antibody is attached to between 6 and 8 copies of CL2A.
11. A CL2A-SN-38 molecule, with a structure represented by:

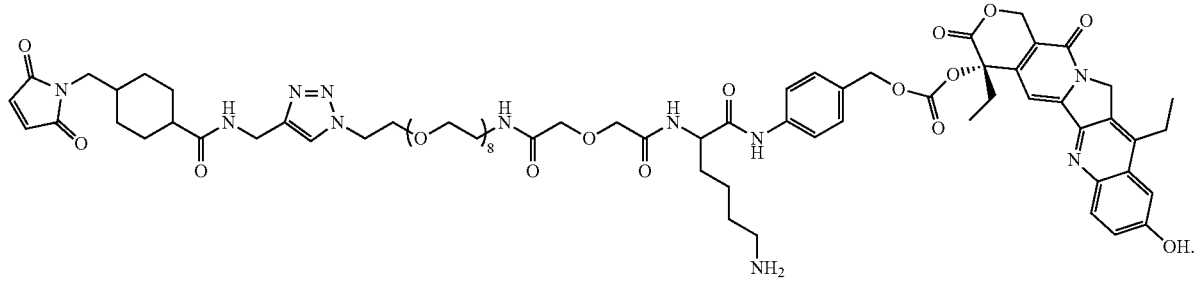

12. The CL2A-SN-38 molecule of claim 11, wherein the CL2A molecule comprises a lysine residue and the lysine epsilon amine group is present as the dichloroacetic acid salt.

13. The CL2A-SN-38 molecule of claim 11, wherein the maleimide moiety of the CL2A molecule is conjugated to a sulfhydryl group on a protein or peptide.

14. The CL2A-SN-38 molecule of claim 13, wherein the protein is an antibody or antibody fragment.

15. The CL2A-SN-38 molecule of claim 14, wherein the antibody fragment is selected from the group consisting of Fab, Fab', F(ab)$_2$, F(ab')$_2$, and scFv.

16. The CL2A molecule of claim 14, wherein the antibody is attached to between 6 and 8 copies of CL2A.

\* \* \* \* \*